United States Patent
Osaka et al.

(10) Patent No.: US 9,051,239 B2
(45) Date of Patent: Jun. 9, 2015

(54) FLUORENE DERIVATIVE, LIGHT-EMITTING ELEMENT, LIGHT-EMITTING DEVICE, ELECTRONIC DEVICE, AND LIGHTING DEVICE

(75) Inventors: Harue Osaka, Kanagawa (JP); Satoko Shitagaki, Kanagawa (JP); Tsunenori Suzuki, Kanagawa (JP); Nobuharu Ohsawa, Kanagawa (JP); Sachiko Kawakami, Kanagawa (JP); Satoshi Seo, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 616 days.

(21) Appl. No.: 12/786,997

(22) Filed: May 25, 2010

(65) Prior Publication Data
US 2010/0301744 A1 Dec. 2, 2010

(30) Foreign Application Priority Data
May 29, 2009 (JP) .................................. 2009-131504

(51) Int. Cl.
| H01L 51/54 | (2006.01) |
| C07C 211/54 | (2006.01) |
| H01L 51/00 | (2006.01) |
| H05B 33/14 | (2006.01) |
| H05B 33/20 | (2006.01) |
| C09B 57/00 | (2006.01) |

(52) U.S. Cl.
CPC .......... *C07C 211/54* (2013.01); *H01L 51/0059* (2013.01); *H01L 51/006* (2013.01); *C07C 2103/18* (2013.01); *C09K 2211/1014* (2013.01); *C09K 2211/1029* (2013.01); *H01L 51/0061* (2013.01); *H01L 51/0072* (2013.01); *H05B 33/14* (2013.01); *H05B 33/20* (2013.01); *C09B 57/00* (2013.01); *C09B 57/008* (2013.01)

(58) Field of Classification Search
CPC .. C07C 211/54; C07C 211/57; C07C 211/61; H01L 51/0059; H01L 51/006; C09K 11/06; C09K 2211/1014; H05B 33/14; H05B 33/20
See application file for complete search history.

(56) References Cited

U.S. PATENT DOCUMENTS

| 5,840,217 A | 11/1998 | Lupo et al. |
| 6,406,804 B1 | 6/2002 | Higashi et al. |
| 6,822,094 B2 | 11/2004 | Salbeck et al. |
| 6,887,392 B2 | 5/2005 | Ogino et al. |
| 7,189,877 B2 | 3/2007 | Nishiyama et al. |
| 7,208,869 B2 | 4/2007 | Ogino et al. |
| 7,303,937 B2 | 12/2007 | Chen et al. |
| 7,326,474 B2 | 2/2008 | Kim |
| 7,540,978 B2 | 6/2009 | Pfeiffer et al. |
| 7,547,562 B2 | 6/2009 | Ogino |
| 7,550,173 B2 | 6/2009 | Seo et al. |
| 7,816,668 B2 | 10/2010 | Kawakami et al. |
| 7,897,964 B2 | 3/2011 | Kawakami et al. |

(Continued)

FOREIGN PATENT DOCUMENTS

| CN | 1634864 A | 7/2005 |
| CN | 1769269 A | 5/2006 |

(Continued)

OTHER PUBLICATIONS

English machine translation of JP 2005-120030 A, 2005.*

(Continued)

*Primary Examiner* — Michael H Wilson
(74) *Attorney, Agent, or Firm* — Fish & Richardson P.C.

(57) ABSTRACT

An object is to provide a light-emitting element having high light-emission efficiency by provision of a novel fluorene derivative as represented by General Formula (G1) below.

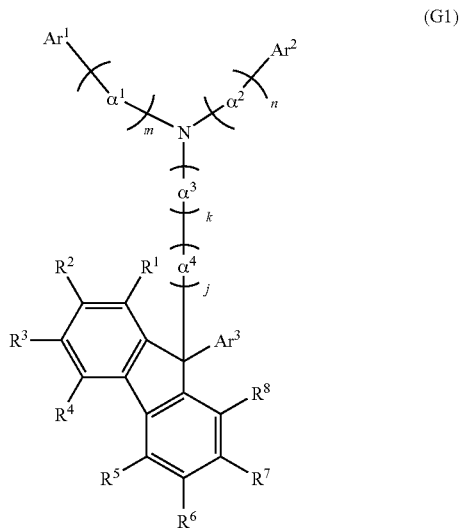

(G1)

In the formula, $R^1$ to $R^8$ independently represent any of a hydrogen atom, an alkyl group having 1 to 6 carbon atoms, a substituted or unsubstituted phenyl group, or a substituted or unsubstituted biphenyl group. Further, $\alpha^1$ to $\alpha^4$ independently represent any of a substituted or unsubstituted arylene group having 6 to 12 carbon atoms. Furthermore, $Ar^1$ and $Ar^2$ independently represent any of an aryl group having 6 to 13 carbon atoms in a ring and $Ar^3$ represents an alkyl group having 1 to 6 carbon atoms or a substituted or unsubstituted aryl group having 6 to 12 carbon atoms. J, k, m, and n each independently represent 0 or 1.

9 Claims, 41 Drawing Sheets

(56) References Cited

U.S. PATENT DOCUMENTS

| | | |
|---|---|---|
| 8,361,638 B2 | 1/2013 | Stoessel et al. |
| 2002/0093283 A1 | 7/2002 | Seo et al. |
| 2004/0110958 A1 | 6/2004 | Nishiyama et al. |
| 2005/0189543 A1 | 9/2005 | Yamazaki et al. |
| 2006/0040132 A1 | 2/2006 | Liao et al. |
| 2006/0063027 A1 | 3/2006 | Vestweber et al. |
| 2006/0180812 A1 | 8/2006 | Sakata et al. |
| 2007/0003785 A1 | 1/2007 | Slusarek et al. |
| 2007/0116984 A1 | 5/2007 | Park et al. |
| 2007/0149784 A1 | 6/2007 | Murata et al. |
| 2007/0215867 A1 | 9/2007 | Kawakami et al. |
| 2008/0122345 A1 | 5/2008 | Sakata et al. |
| 2008/0124572 A1 | 5/2008 | Mizuki et al. |
| 2008/0199726 A1 | 8/2008 | Schafer et al. |
| 2008/0206598 A1 | 8/2008 | Ohsawa et al. |
| 2009/0160323 A1 | 6/2009 | Nomura et al. |
| 2010/0301744 A1 | 12/2010 | Osaka et al. |
| 2011/0037027 A1 | 2/2011 | Stoessel et al. |
| 2011/0147728 A1 | 6/2011 | Kawakami et al. |
| 2011/0220881 A1 | 9/2011 | Yokoyama et al. |
| 2012/0161107 A1 | 6/2012 | Yokoyama et al. |

FOREIGN PATENT DOCUMENTS

| | | | |
|---|---|---|---|
| CN | 1950479 A | 4/2007 | |
| EP | 1400578 A1 | 3/2004 | |
| EP | 2225204 A | 6/2009 | |
| EP | 2757094 A | 7/2014 | |
| JP | 7301928 A | 11/1995 | |
| JP | 2003-261472 A | 9/2003 | |
| JP | 2004087395 A | 3/2004 | |
| JP | 2004315495 A | 11/2004 | |
| JP | 2005085509 A | 3/2005 | |
| JP | 2005/120030 A * | 5/2005 | ............ C07C 211/54 |
| JP | 2005-162660 A | 6/2005 | |
| JP | 2006-093284 A | 4/2006 | |
| JP | 2007-534722 | 11/2007 | |
| JP | 2009-298767 A | 12/2009 | |
| JP | 2011-521894 | 7/2011 | |
| KR | 2012014913 A | 2/2012 | |
| WO | 2005/105950 A1 | 11/2005 | |
| WO | WO2005121064 A1 | 12/2005 | |
| WO | WO2006062218 A1 | 6/2006 | |
| WO | 2008-062636 A1 | 5/2008 | |
| WO | 2009/072587 A1 | 6/2009 | |
| WO | 2009/124627 A1 | 10/2009 | |
| WO | 2009/151039 A1 | 12/2009 | |
| WO | 2010/052932 A1 | 5/2010 | |
| WO | WO2010137601 A1 | 12/2010 | |

OTHER PUBLICATIONS

Hou et al. "Stable hole-transporting molecular glasses based on complicated 9,9-diarylfluorenes (CDAFs)." Synthetic Metals, 2009. vol. 159, pp. 1055-1060.*

Goldsmith, C. et al., "C—H Bond Activation by a Ferric Methoxide Complex: Modeling the Rate-Determining Step in the Mechanism of Lipoxygenase," Journal of the American Chemical Society, 2002, vol. 124, No. 1, pp. 83-96.

International Search Report for Application No. PCTJP2010058854, dated Aug. 31, 2010, 2 pages.

International Written Opinion for Application No. PCTJP2010058854, dated Aug. 31, 2010, 3 pages.

Ohnishi et al., "A Method of Measuring an Energy Level," High Molecular EL Materials—Development of Light-Emitting High Molecular Compounds, Dec. 25, 2004, pp. 64-67, Kyoritsu Shuppan.

Shen, J. et al., "High TG Blue Emitting Materials for Electroluminescent Devices," Journal of Materials Chemistry, 2005, vol. 15, No. 25, pp. 2455-2463.

Shih, P. et al., "A Novel Fluorene-Triphenylamine Hybrid That is a Highly Efficient Host Material for Blue-,Green-, and Red-Light-Emitting Electrophosphorescent Devices," Advanced Functional Materials, 2007, vol. 17, pp. 3514-3520.

Thomas, K. et al., "Green and Yellow Electroluminescent Dipolar Carbazole Derivatives: Features and Benefits of Electron-Withdrawing Segments," Chemistry of Materials, 2002, vol. 14, No. 9, pp. 3852-3859.

Thomas, K. et al., "New Carbazole-Oxadiazole Dyads for Electroluminescent Devices: Influence of Acceptor Substituents on Luminescent and Thermal Properties," Chemistry of Materials, 2004, vol. 16, No. 25, pp. 5437-5444.

Van Slyke, S. et al., "Organic Electroluminescent Devices With Improved Stability," Applied Physics Letters, Oct. 7, 1996, vol. 69, No. 15, pp. 2160-2162.

Tsutsui, T. et al., "High Quantum Efficiency in Organic Light-Emitting Devices With Iridium-Complex As a Triplet Emissive Center", Jpn. J. Appl. Phys. (Japanese Journal of Applied Physics), Dec. 15, 1999, vol. 38, No. 12B, pp. L1502-L1504.

Adachi, C. et al., "High-Efficiency Red Electrophosphorescence Devices", Appl. Phys. Lett. (Applied Physics Letters), Mar. 12, 2001, vol. 78, No. 11, pp. 1622-1624.

Kafafi, Z., Organic Electroluminscence, 2005, pp. 152-161, Taylor & Francis.

European Search Report (EP Application No. 10780556.6) dated Oct. 16, 2012, 10 pages.

Chinese Office Action (CN Application No. 201080025006.4) dated Jun. 21, 2013 with English translation, 17 pages.

* cited by examiner

FLUORENE DERIVATIVE, LIGHT-EMITTING ELEMENT, LIGHT-EMITTING DEVICE, ELECTRONIC DEVICE, AND LIGHTING DEVICE

TECHNICAL FIELD

The present invention relates to a fluorene derivative, a light-emitting element, a light-emitting device, an electronic device, and a lighting device.

BACKGROUND ART

In recent years, research and development have been extensively conducted on light-emitting elements using electroluminescence. In a basic structure of such a light-emitting element, a layer containing a substance with a light-emitting property is interposed between a pair of electrodes. By voltage application to this element, light emission can be obtained from the substance having a light-emitting property.

Since such a light-emitting element is of self-light-emitting type, it is considered that the light-emitting element has advantages over a liquid crystal display in that visibility of pixels is high, backlight is not required, and so on and is therefore suitable as flat panel display elements. Besides, such a light-emitting element has advantages in that it can be formed to be thin and lightweight, and has quite fast response speed.

Furthermore, since such a light-emitting element can be formed in a film form, planar light emission can be easily obtained. Thus, a large-area element utilizing planar light emission can be formed. This is a feature which is difficult to be obtained by point light sources typified by an incandescent lamp and an LED or linear light sources typified by a fluorescent lamp. Accordingly, the light-emitting element is extremely effective for use as a surface light source applicable to lighting and the like.

Light-emitting elements utilizing electroluminescence are broadly classified according to whether they use an organic compound or an inorganic compound as a light-emitting substance. When an organic compound is used as a light-emitting substance, by voltage application to a light-emitting element, electrons and holes are injected into a layer including the light-emitting organic compound from a pair of electrodes, whereby current flows. Light is emitted when the carriers (electrons and holes) are recombined and the electrons and holes of the organic compound returns to the ground state from the excited state where both the electrons and the holes are generated in organic molecules with a light-emitting property.

Because of such a mechanism, the light-emitting element is called a current-excitation light-emitting element. It is to be noted that the excited state generated by an organic compound can be a singlet excited state or a triplet excited state, and luminescence from the singlet excited state is referred to as fluorescence, and luminescence from the triplet excited state is referred to as phosphorescence.

In addition to light emission by recombination of current excitation carriers, which is described above, there is a method in which excitation energy is transferred to another organic compound, whereby the organic compound is excited to provide light emission. This is an element structure in which a light-emitting material is diffused (doped) to the light-emitting layer in general organic EL. A host means a material into which a light-emitting material is diffused and a dopant means a material which is diffused into the host. This, in order to solve a problem in that organic molecules to provide light emission have low light emission efficiency because stacking interaction occurs when they are high concentration (concentration quenching), contributes to higher light emission efficiency by doping the organic molecules to the host and suppressing stack. At this time, the excitation energy by current excitation is transferred to the dopant from the host excited by current excitation, so that the dopant emits light.

This excitation energy transfer occurs only when transfer from high excitation energy to low excitation energy is performed. Therefore, a material having a high excitation state is preferably used for a host material.

An organic EL layer has a plurality of layers, and a carrier-transport layer is generally provided between a light-emitting layer and an electrode. As one of the reasons, a carrier-transport layer can prevent excitation energy in the light-emitting layer from quenching caused by energy transfer to the electrode. Further, a material (an exciton-blocking material) having higher excitation energy than a light-emitting layer is preferably used for a carrier-transport layer which is adjacent to the light-emitting layer so that excitation energy in the light-emitting layer is not transferred.

As another reason to provide a carrier-injection layer and a carrier-transport layer between a light-emitting layer and an electrode in an organic EL, it is to adjust a carrier injection partition between adjacent layers. Accordingly, recombination can be efficiently performed in the light-emitting layer.

In improving element characteristics of such a light-emitting element, there are a lot of problems which depend on a substance, and in order to solve the problems, improvement of an element structure, development of a substance, and the like have been carried out (for example, see Patent Document 1).

REFERENCE

Patent Document

[Patent Document 1]: PCT International Publication No. 08/062,636

DISCLOSURE OF INVENTION

An object of an embodiment of the present invention is to provide a novel fluorene derivative as a substance having a high hole-transport property. Another object is to provide a light-emitting element having high light emission efficiency by application of the novel fluorene derivative for a light-emitting element. Another object of an embodiment of the present invention is to provide a light-emitting device, an electronic device, and a lighting device each with low power consumption and low driving voltage.

An embodiment of the present invention is a fluorene derivative represented by General Formula (G1) below.

[Chemical Formula 1]

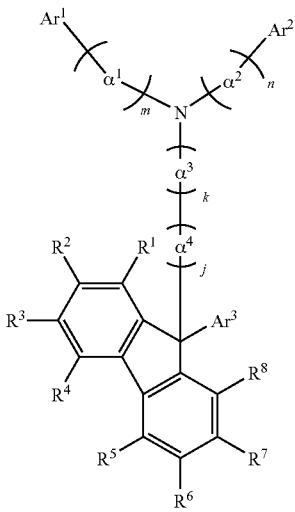

(G1)

In the formula, $R^1$ to $R^8$ independently represent any of a hydrogen atom, an alkyl group having 1 to 6 carbon atoms, a substituted or unsubstituted phenyl group, or0 a substituted or unsubstituted biphenyl group. Further, $\alpha^1$ to $\alpha^4$ independently represent any of a substituted or unsubstituted arylene group having 6 to 12 carbon atoms. Furthermore, $Ar^1$ and $Ar^2$ independently represent any of an aryl group having 6 to 13 carbon atoms in a ring and $Ar^3$ represents an alkyl group having 1 to 6 carbon atoms or a substituted or unsubstituted aryl group having 6 to 12 carbon atoms. J, k, m, and n independently represent 0 or 1. Note that at least one of J and k is 1.

In the above structure, $R^1$ to $R^8$ in General Formula (G1) are independently represented by any of Structural Formula (R-1) to Structural Formula (R-9).

[Chemical Formula 2]

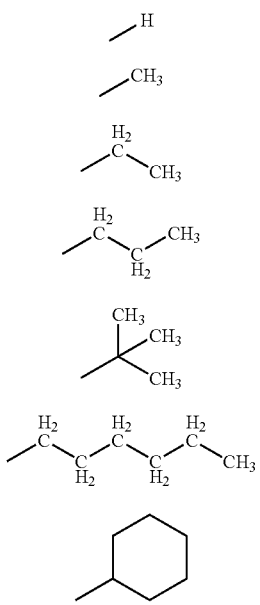

(R-1)
(R-2)
(R-3)
(R-4)
(R-5)
(R-6)
(R-7)

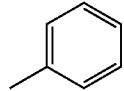

(R-8)

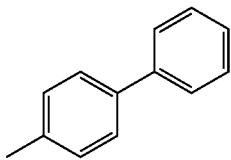

(R-9)

In the above structure, $\alpha^1$ to $\alpha^4$ in General Formula (G1) are independently represented by any of Structural Formula ($\alpha$-1) to Structural Formula ($\alpha$-3).

[Chemical Formula 3]

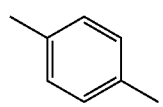

($\alpha$-1)

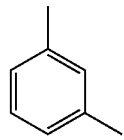

($\alpha$-2)

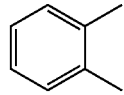

($\alpha$-3)

In the above structure, $Ar^1$ and $Ar^2$ in General Formula (G1) are independently represented by any of Structural Formula (Ar-1) to Structural Formula (Ar-6), and $Ar^3$ is represented by any of Structural Formula (Ar3-1) to Structural Formula (Ar3-8).

[Chemical Formula 4]

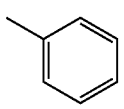

(Ar-1)

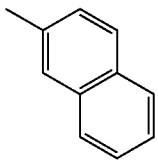

(Ar-2)

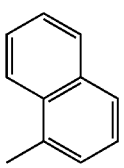

(Ar-3)

(Ar-4)
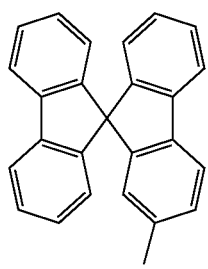
(Ar-5)
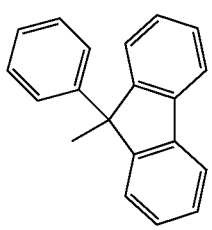
(Ar-6)
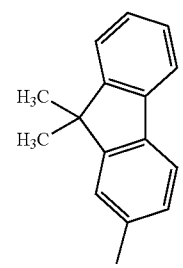
[Chemical Formula 5]
(Ar3-1) 
(Ar3-2) 
(Ar3-3) 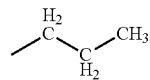
(Ar3-4) 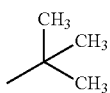
(Ar3-5) 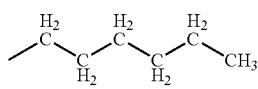
(Ar3-6) 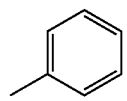
(Ar3-7) 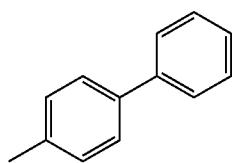
(Ar3-8)
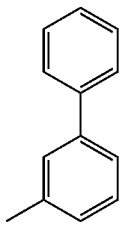
Another embodiment of the present invention is represented by Structural Formula (101), Structural Formula (151), or Structural Formula (118) below.
[Chemical Formula 6]
(101)
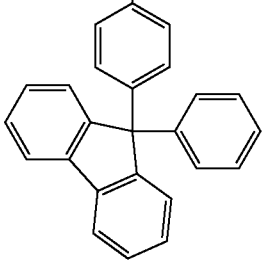
[Chemical Formula 7]
(151)
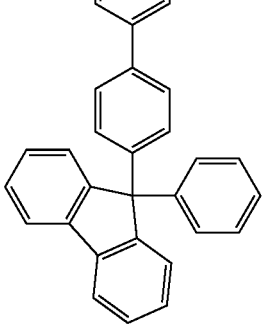

[Chemical Formula 8]

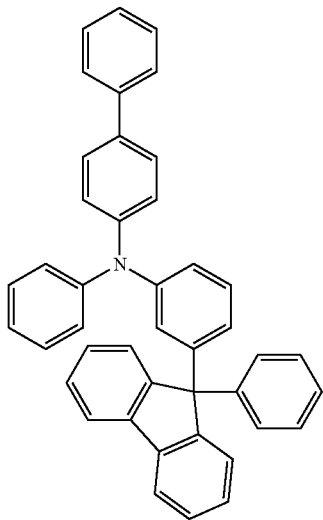

(118)

Further, another embodiment of the present invention is a light-emitting element including an EL layer between a pair of electrodes. The EL layer includes at least a light-emitting layer and a hole-transport layer and the hole-transport layer includes one or a plurality of the fluorene derivatives described above.

Furthermore, another embodiment of the present invention is a light-emitting device formed using the above-described light-emitting element. Another embodiment of the present invention is an electronic device formed using the above-described light-emitting device. Another embodiment of the present invention is a lighting device formed using the above-described light-emitting device The light-emitting device of an embodiment of the present invention is a light-emitting device including the aforementioned light-emitting element and a control means which controls the light emission from the light-emitting element. Note that the light-emitting device in this specification includes image display devices, light-emitting devices, or light sources (including lighting device). In addition, the light-emitting device includes any of the following modules in its category: a module in which a connector such as an flexible printed circuit (FPC), a tape automated bonding (TAB) tape, or a tape carrier package (TCP) is attached to a panel; a module having a TAB tape or a TCP provided with a printed wiring board at the end thereof; and a module having an integrated circuit (IC) directly mounted on a light-emitting element by a chip on glass (COG) method.

Further, an electronic device of an embodiment of the light-emitting device of the present invention is used for a display portion is also included in the category of the present invention. Consequently, an embodiment of an electronic device of the present invention includes a display portion, in which the display portion is provided with the above light-emitting device.

Furthermore, a lighting device using an embodiment of the light-emitting device of the present invention is also included in the category of the present invention. Therefore, an embodiment of the lighting device of the present invention is provided with the above light-emitting device.

Since the fluorene derivative of the present invention has a high hole-transport property, it can be mainly used for a hole-transport layer which is included in an EL layer of a light-emitting element. In addition, the fluorene derivative of the present invention is used for the hole-transport layer to form a light-emitting element, whereby a light-emitting element having high luminous efficiency can be formed.

Also, by use of such a light-emitting element, a light-emitting device, an electronic device, and a lighting device with low power consumption and low drive voltage can be obtained.

BEST MODE FOR CARRYING OUT THE INVENTION

Figure 1A:
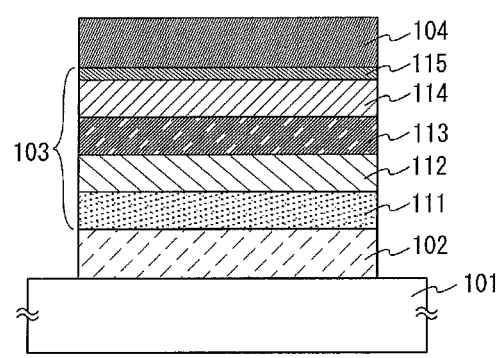
FIGS. 1A and 1B are views each illustrating a light-emitting element.

Hereinafter, Embodiments of the present invention are described with reference to the drawings. Note that the invention is not limited to the following description, and it will be easily understood by those skilled in the art that various changes and modifications can be made without departing from the spirit and scope of the invention. Therefore, the invention should not be construed as being limited to the description in the following embodiments.

(Embodiment 1)

In Embodiment 1, a fluorene derivative of an embodiment of the present invention is described.

The fluorene derivative of an embodiment of the present invention is a fluorene derivative represented by General Formula (G1).

[Chemical Formula 9]

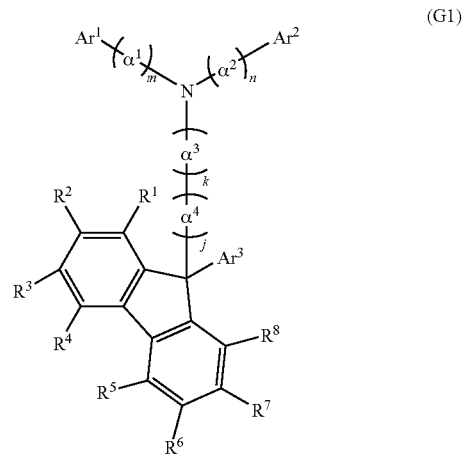

(G1)

In the formula, $R^1$ to $R^8$ independently represent any of a hydrogen atom, an alkyl group having 1 to 6 carbon atoms, a substituted or unsubstituted phenyl group, or a substituted or unsubstituted biphenyl group. Further, $\alpha^1$ to $\alpha^4$ independently represent any of a substituted or unsubstituted arylene group having 6 to 12 carbon atoms. Furthermore, $Ar^1$ and $Ar^2$ independently represent any of an aryl group having 6 to 13 carbon atoms in a ring and $Ar^3$ represents an alkyl group having 1 to 6 carbon atoms or a substituted or unsubstituted aryl group having 6 to 12 carbon atoms. J, k, m, and n are independently represent 0 or 1. Note that at least one of J and k is 1.

In the case where $R^1$ to $R^8$, $\alpha^1$ to $\alpha^4$, $Ar^1$, $Ar^2$, $Ar^3$ have substituents, an alkyl group such as a methyl group, an ethyl group, a propyl group, a pentyl group or a hexyl group, or an aryl group such as a phenyl group or a biphenyl group can be given as an example of the substituent. Alternatively, the substituents may be connected to each other to form a ring (for example, a biphenyl group forms a ring with a fluorenyl group of $Ar^1$ or $Ar^2$ to be a 9,9'-spirofluorenyl group or a hexyl group forms a ring to be a cyclohexyl group).

It is considered that when an alkyl group is used in General Formula (G1), the solubility in an organic solvent is improved; therefore, in a case where an element is formed using this material by a wet method, a use of a material having an alkyl group makes manufacturing an element easy, which is preferable.

As $R^1$ to $R^8$ in General Formula (G1), a hydrogen atom, an alkyl group such as a methyl group, an ethyl group, a propyl group, a pentyl group or a hexyl group, a substituted or unsubstituted phenyl group, or a substituted or unsubstituted aryl group such as a biphenyl group can be given. Structural Formulae (R-1) to (R-9) are specifically given.

[Chemical Formula 10]

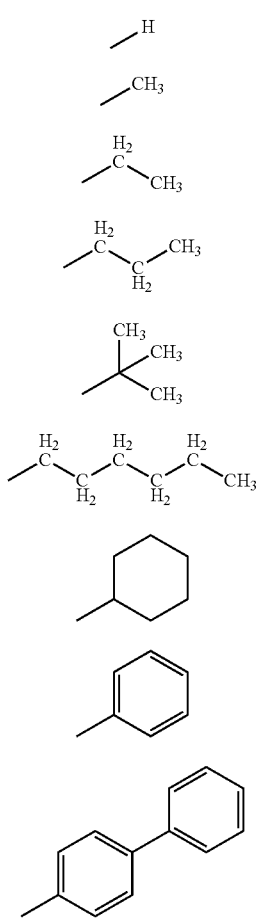

(R-1)
(R-2)
(R-3)
(R-4)
(R-5)
(R-6)
(R-7)
(R-8)
(R-9)

As $\alpha^1$ to $\alpha^4$ in General Formula (G1), a substituted or unsubstituted phenylene group can be given. Structural Formulae ($\alpha$-1) to ($\alpha$-3) are specifically given.

[Chemical Formula 11]

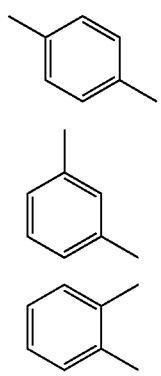

($\alpha$-1)
($\alpha$-2)
($\alpha$-3)

As $Ar^1$ and $Ar^2$ in General Formula (G1), a substituted or unsubstituted phenyl group, a substituted or unsubstituted biphenyl group, a substituted or unsubstituted naphthyl group, a substituted or unsubstituted fluorenyl group, or a substituted or unsubstituted aryl group such as spirofluorenyl group can be given. Structural Formulae (Ar-1) to (Ar-6) are specifically given. (Ar-4) below is one in which a biphenyl group forms a ring with a fluorenyl group of $Ar^1$ or $Ar^2$ to be a 9,9'-spirofluorenyl group.

In this case, when a condensed ring group is used as in (Ar-2) or (Ar-3), a carrier-transport property is improved, which is preferable. Also in this case, when $\alpha^1$ or $\alpha^2$ which is between a condensed ring group and a nitrogen atom is 1, a band gap (Bg) of a molecule can be kept wider, which is preferable. Further, as in (Ar-5), a structure using a bond binding by a sigma bond hardly makes conjugation from a nitrogen atom extend, and Bg and T1 level are high. Therefore, it is thought that this material can be used, in a light-emitting element with a shorter wavelength, as a material of a layer adjacent to the light-emitting layer or a dopant material to the light-emitting layer, which is preferable. Further, when a condensed ring group having large and rigid molecular weight, such as (Ar-2), (Ar-3), or (Ar-4), is used, thermophysical properties such as the glass transition point ($T_g$) are improved, which is preferable.

[Chemical Formula 12]

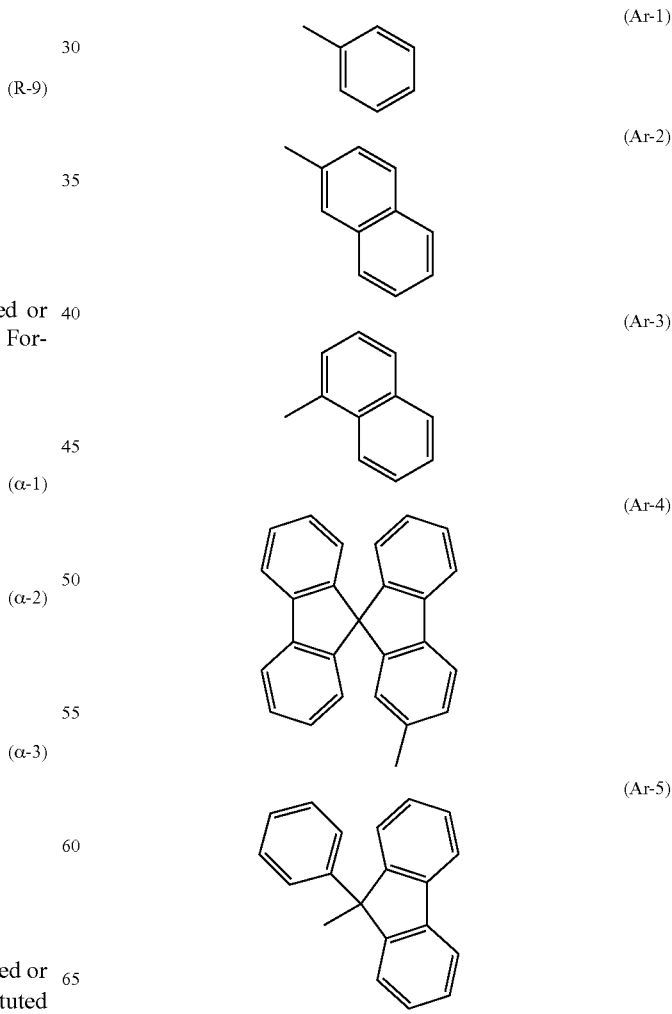

(Ar-1)
(Ar-2)
(Ar-3)
(Ar-4)
(Ar-5)

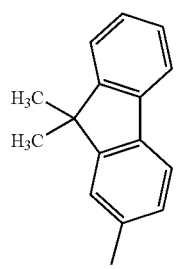
(Ar-6)

As $Ar^3$ in General Formula (G1), an alkyl group such as a methyl group, an ethyl group, a propyl group, a pentyl group or a hexyl group, a substituted or unsubstituted phenyl group, or a substituted or unsubstituted aryl group such as a biphenyl group can be given. Structural Formulae (Ar3-1) to (Ar3-8) are specifically given.

[Chemical Formula 13]

(Ar3-1)

(Ar3-2)

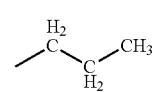
(Ar3-3)

(Ar3-4)

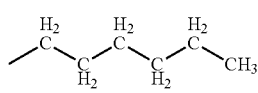
(Ar3-5)

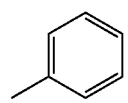
(Ar3-6)

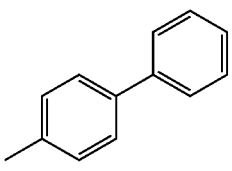
(Ar3-7)

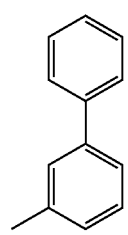
(Ar3-8)

As specific examples of a fluorene derivative represented by General Formula (G1), fluoren derivatives represented by Structural Formulae (100) to (123) or Structural Formulae (150) to (173) can be given. However, an embodiment of the present invention is not limited to these.

[Chemical Formula 14]

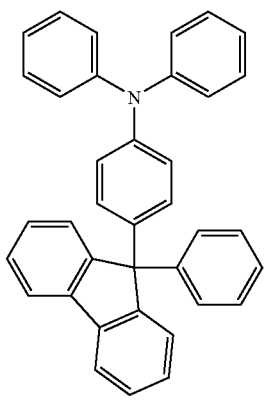
(100)

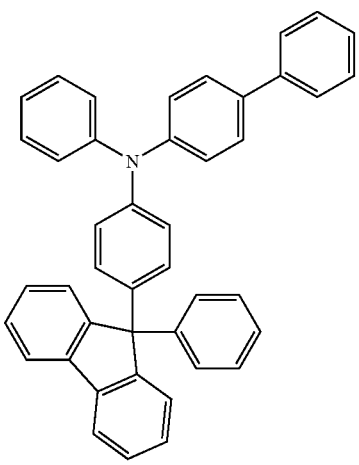
(101)

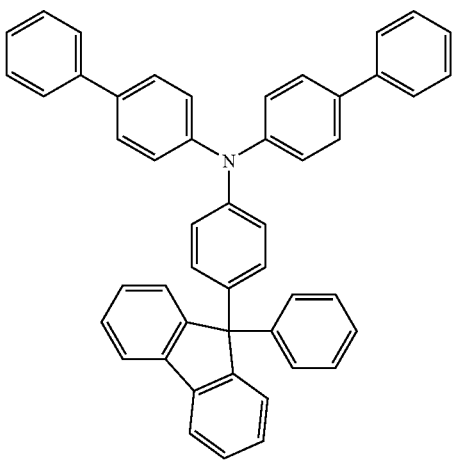
(102)

[Chemical Formula 15]
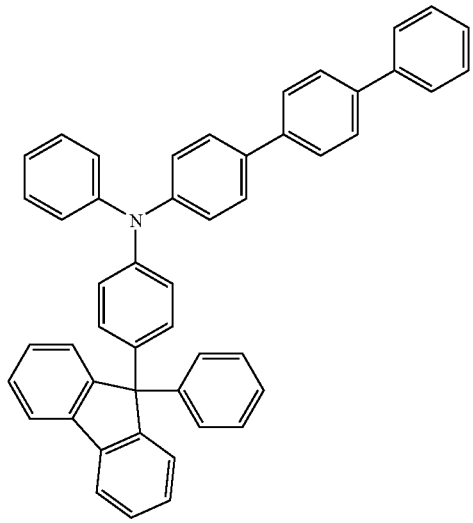
(103)
(104)
(105)
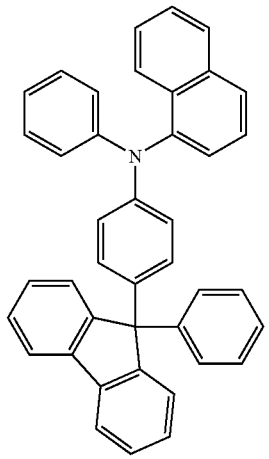
(106)
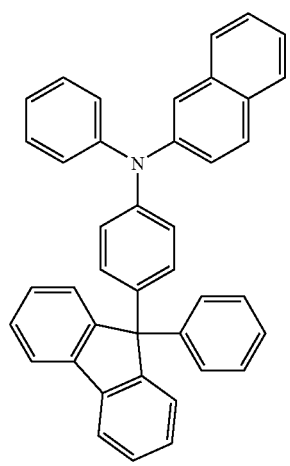
(107)
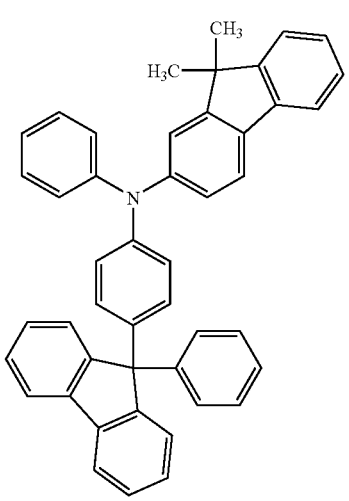
(108)

(109)
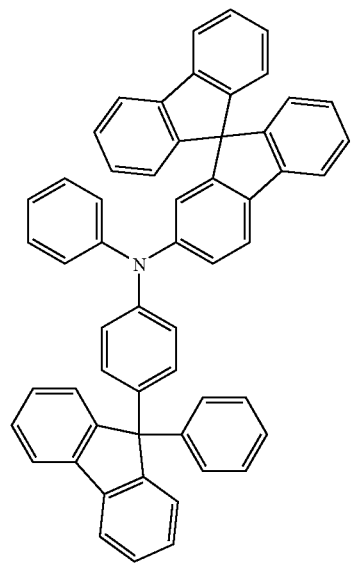
[Chemical Formula 16]
(112)
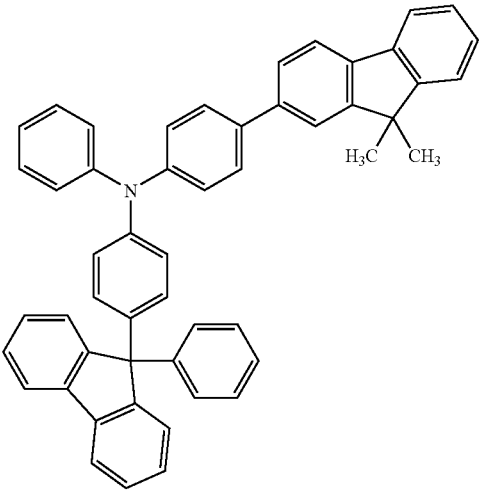
(110)
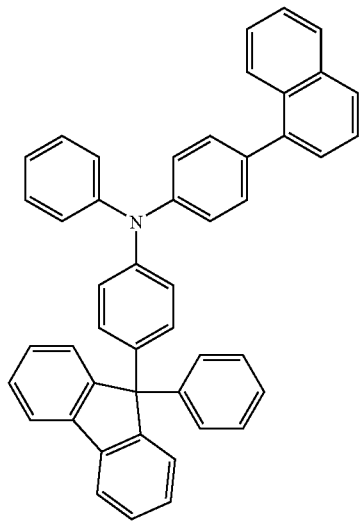
(113)
(111)
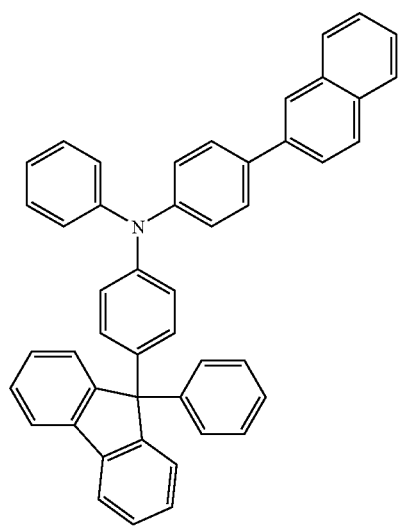
(114)
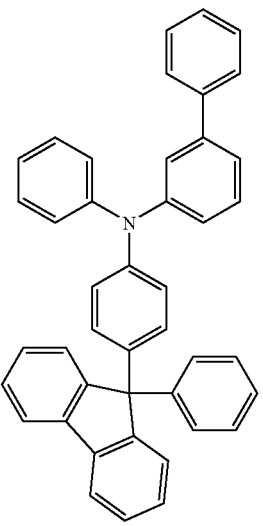

[Chemical Formula 17]
(115) 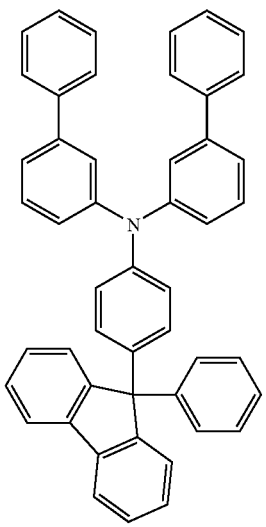
(116) 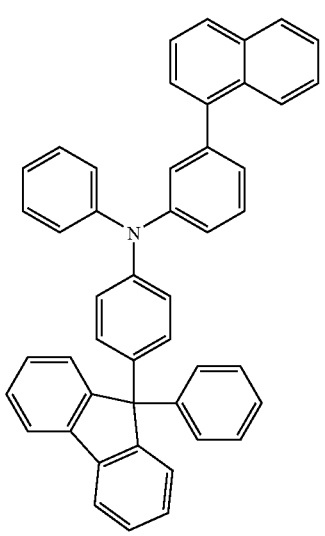
(117) 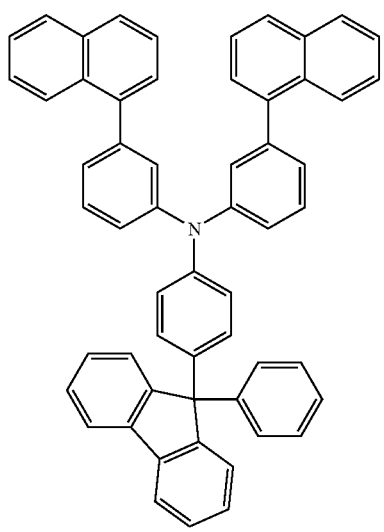
(118) 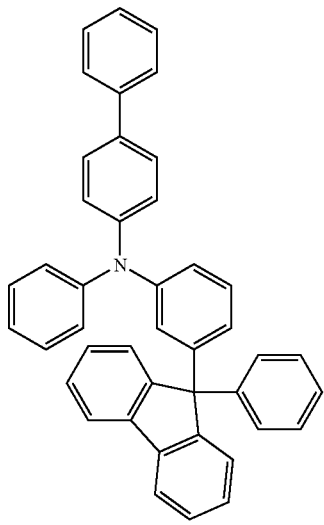
(119) 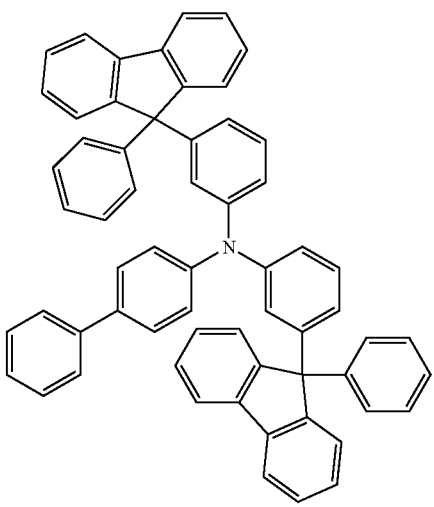
(120) 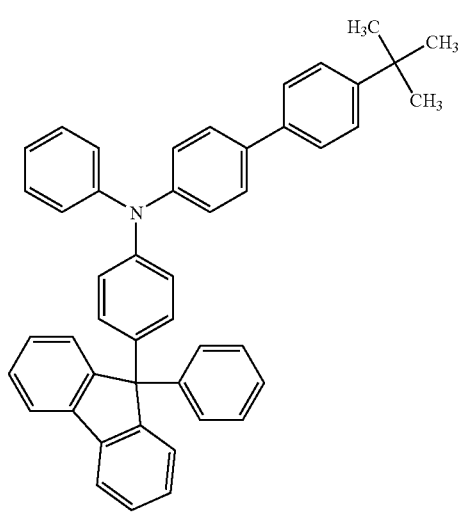

(121)
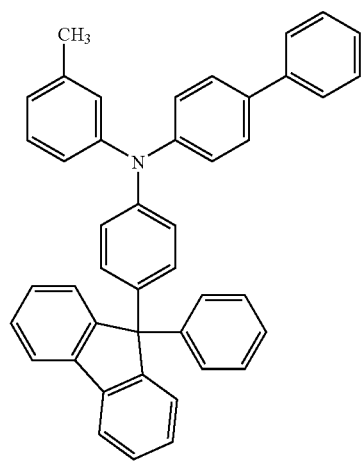
(122)
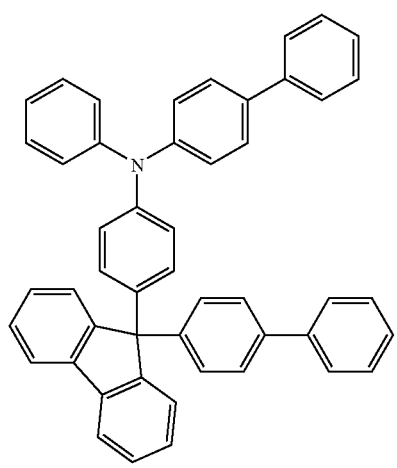
(123)
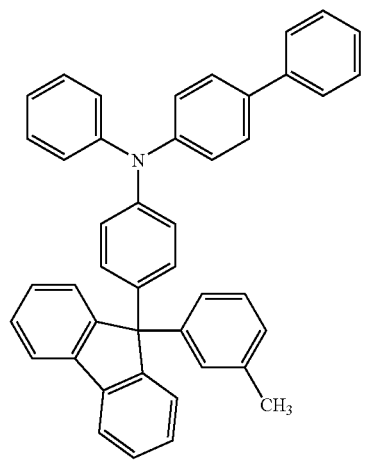
[Chemical Formula 18]
(150)
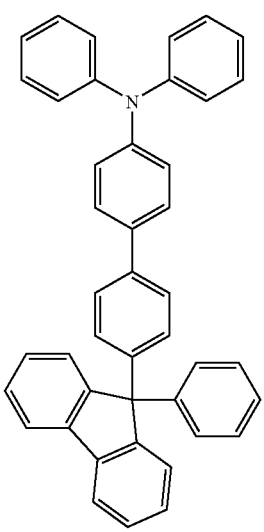
(151)
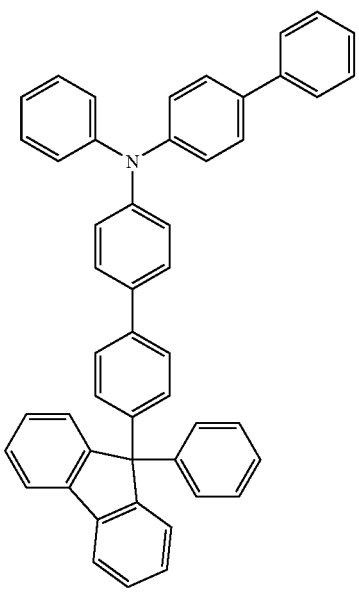

(152)
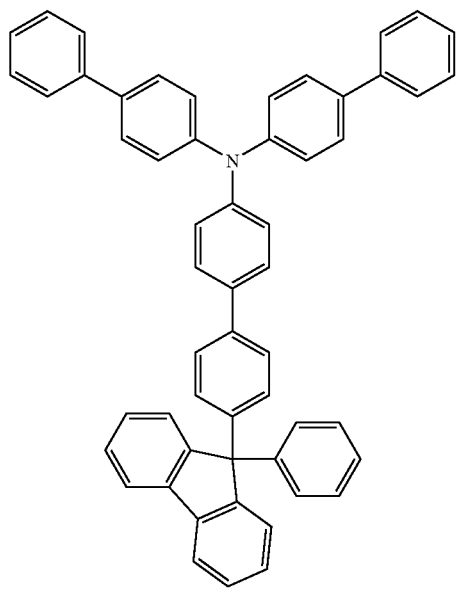
(154)
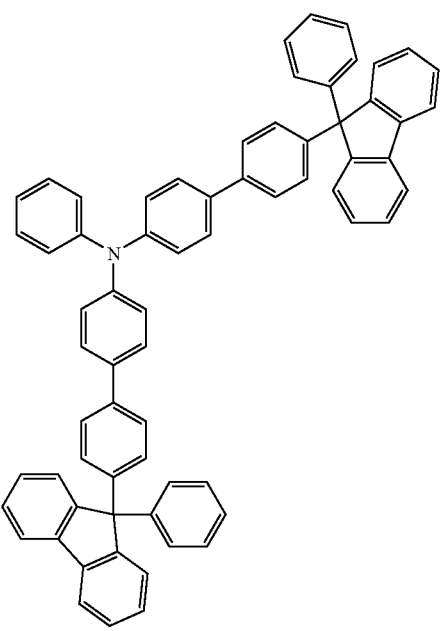
(153)
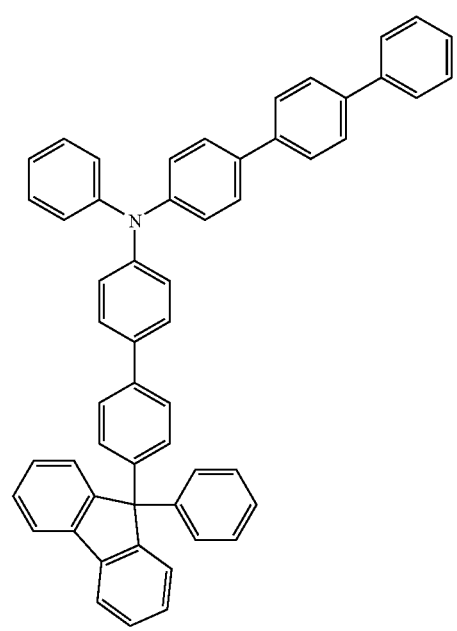
(155)
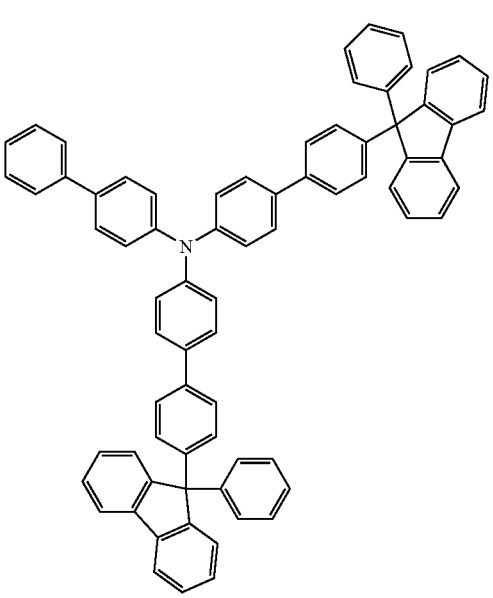

(156)
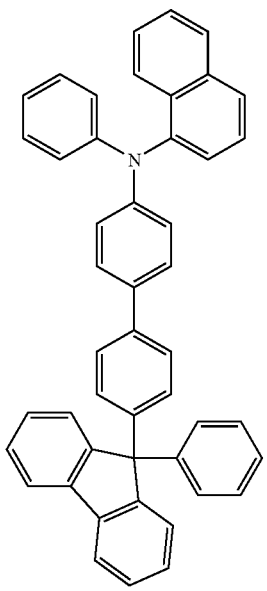
(158)
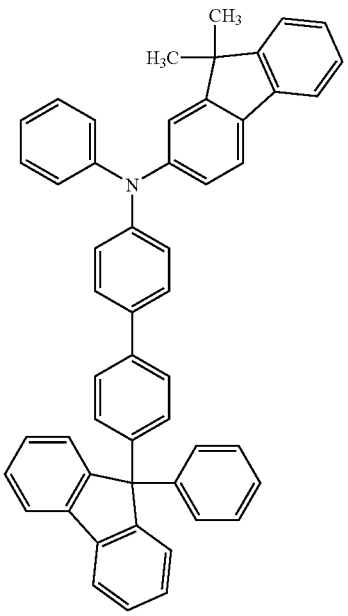
(157)
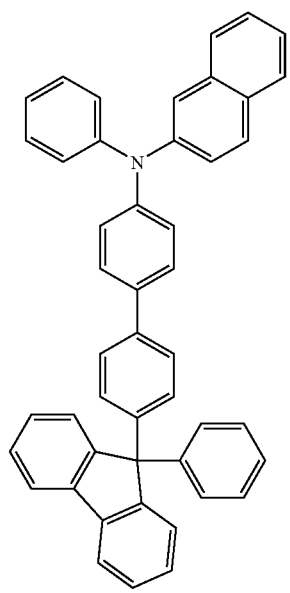
(159)
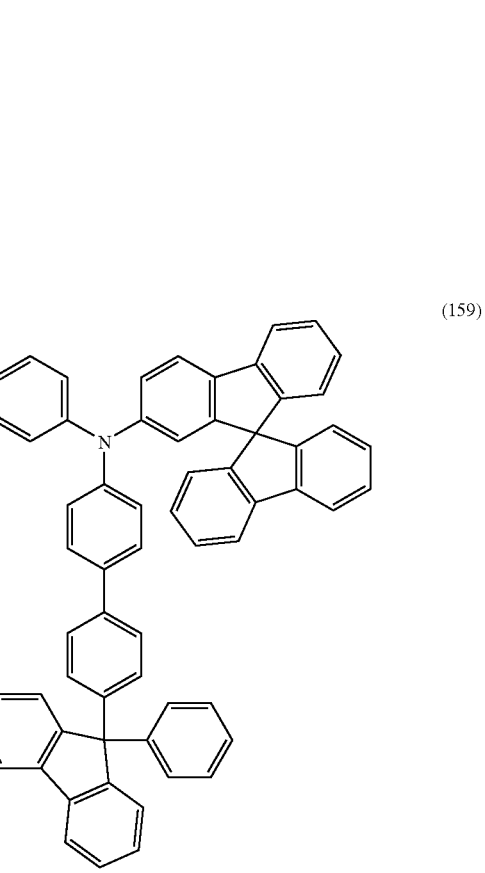

(160)
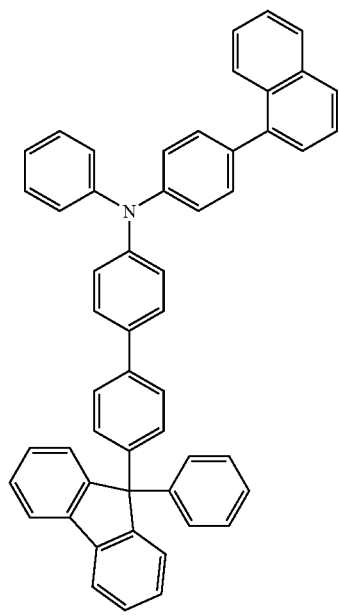
[Chemical Formula 20]
(162)
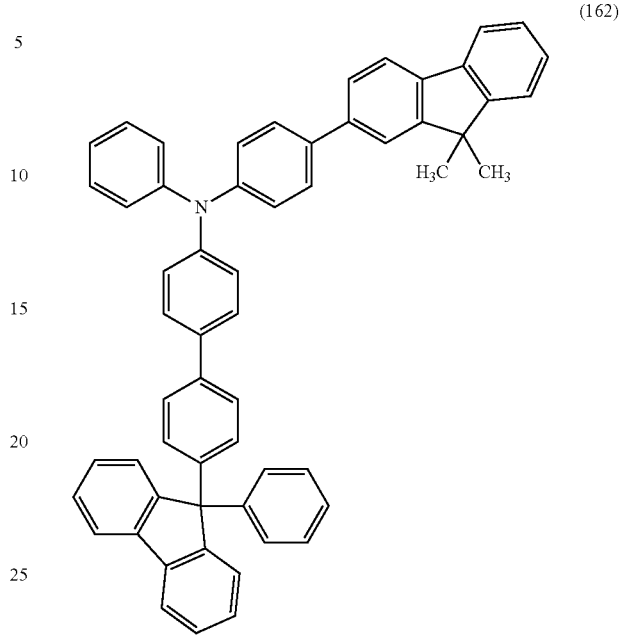
(161)
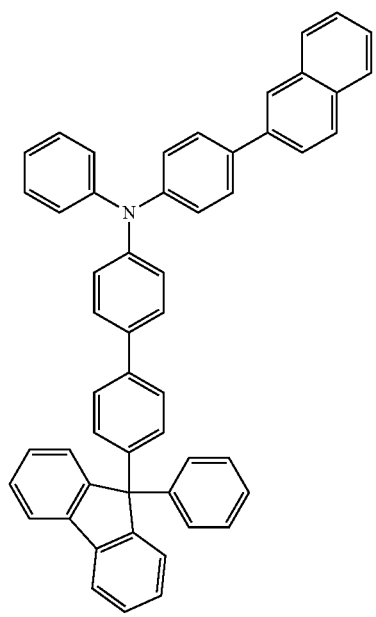
(163)
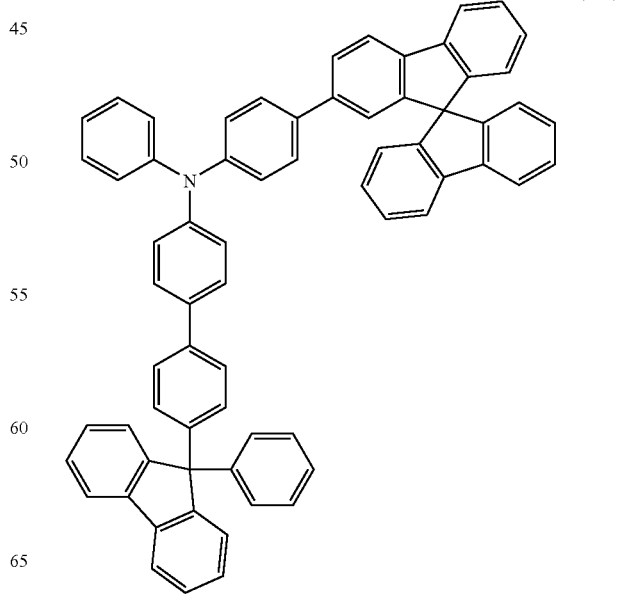

(164)
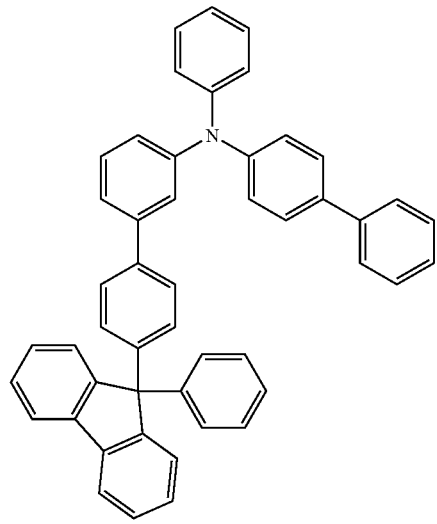
(165)
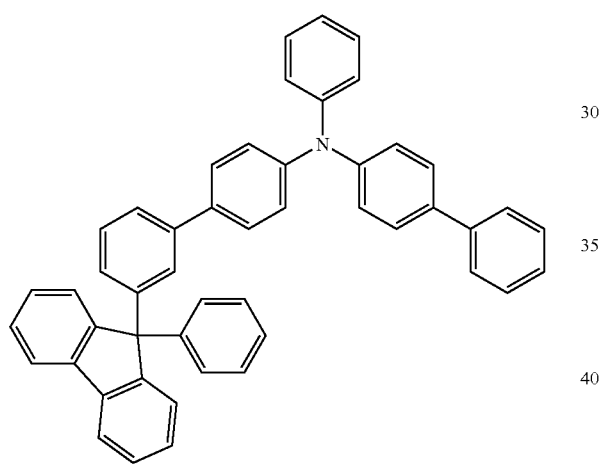
(166)
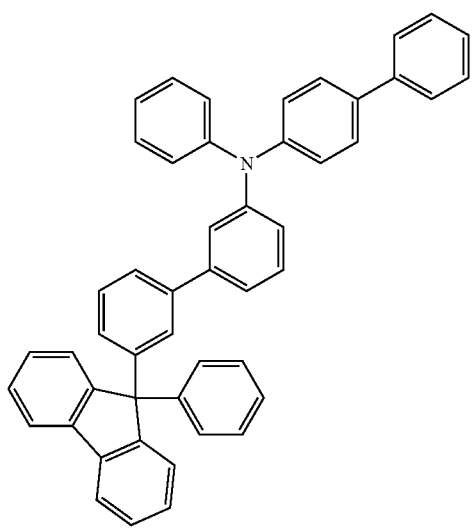
(167)
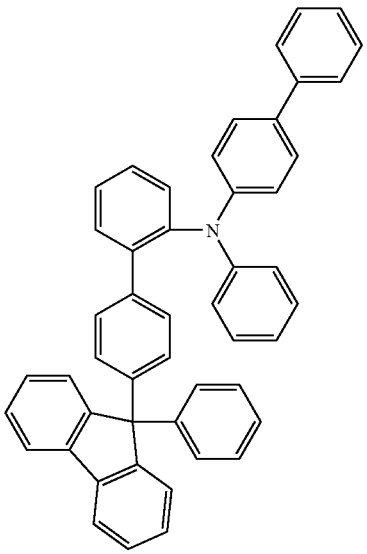
[Chemical Formula 21]
(168)
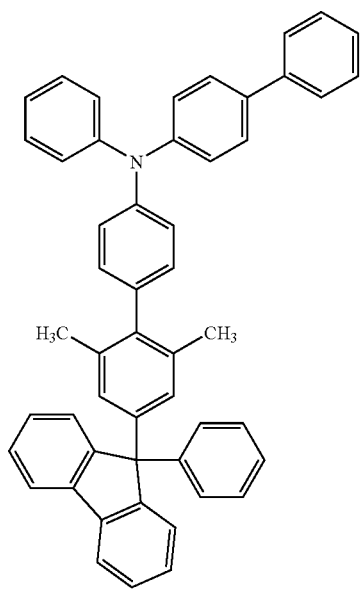

(169)
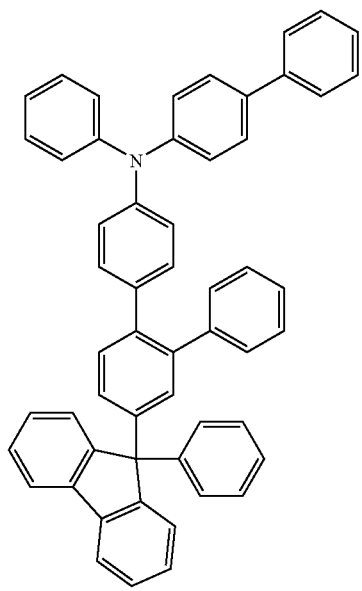
(170)
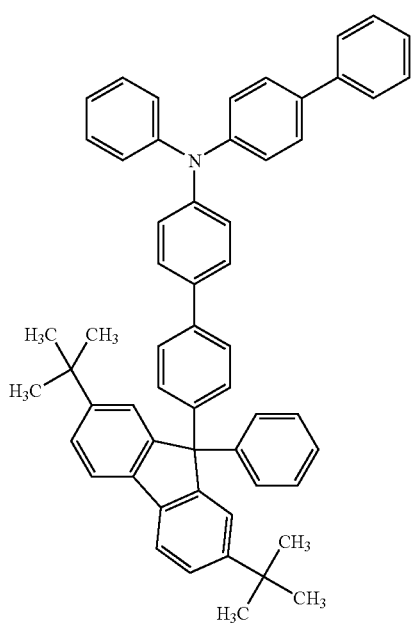
(171)
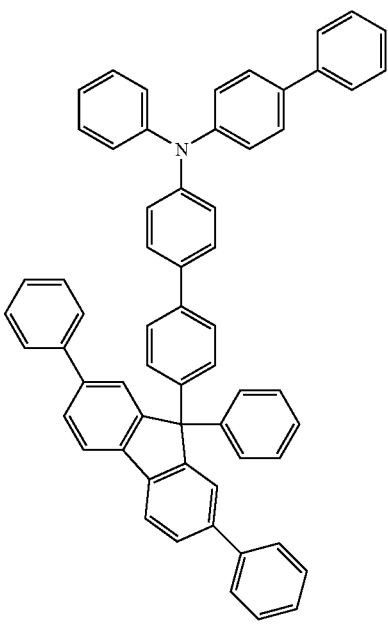
(172)
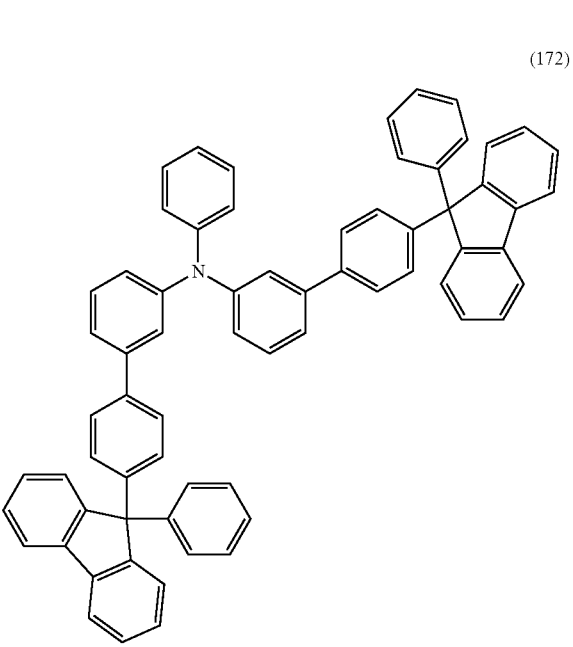

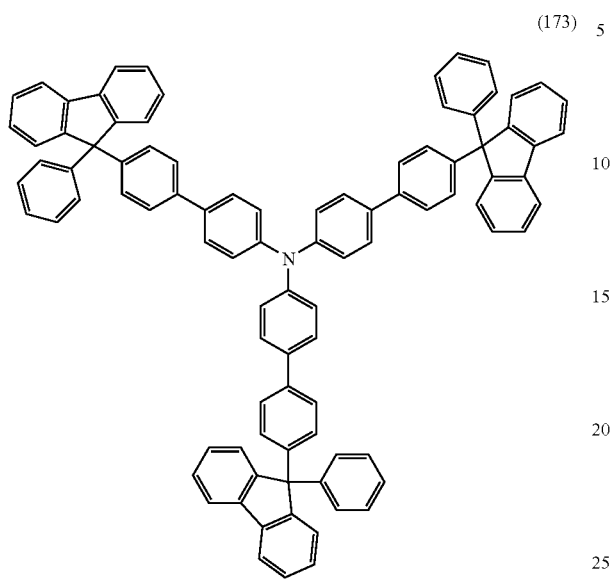

(173)

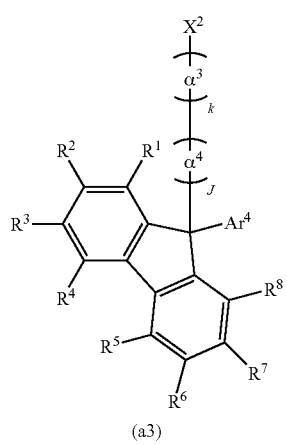

(a3)

An aryl compound including a halogen group in the scheme (A-1) is activated, is reacted with a benzoyl derivative to be a phenol derivative, and is dehydroxilated by addition of acid, whereby a fluorene derivative can be obtained.

As an example of the activation, a reaction using alkyl lithium reagent to perform lithiation or a reaction using activated magnesium to obtain a Grignard reagent can be used. As alkyl lithium, n-butyllithium, tert-butyllithium, methyllithium, and the like can be given. As acid, hydrochloric acid or the like can be used. As a dehydrating solvent, an ether such as diethyl ether or tetrahydrofuran (THF) can be used.

As shown in a scheme (A-2), a halogenated arene derivative (a4) and an arylamine derivative (a5) are coupled, whereby a diarylamine derivative (a6) can be obtained.

A variety of reactions can be applied to a synthesis method of a fluorene derivative of an embodiment of the present invention. For example, the fluorene derivative represented by General Formula (G1) of an embodiment of the present invention can be synthesized by synthesis reactions described below. Note that the synthesis method of the fluorene derivative of an embodiment of the present invention is not limited to the following synthesis methods.

<Synthesis Method 1 of the Fluorene Derivative Represented by General Formula (G1)>

As shown in a scheme (A-1), a 1-halogenated biphenyl derivative (a1) is lithiated or made into a Grignard reagent and is reacted with a benzoyl derivative (a2) to be dehydroxilated, so that a haloarylfluorene derivative (a3) can be obtained.

[Chemical Formula 22]

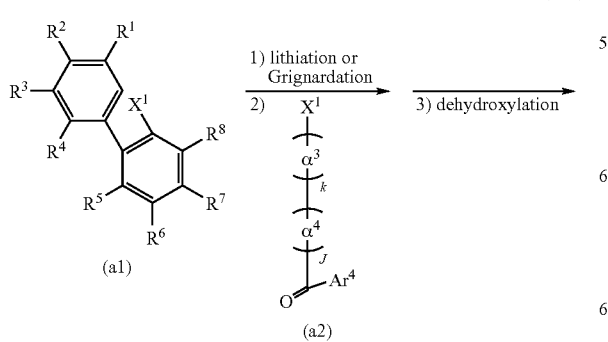

[Chemical Formula 23]

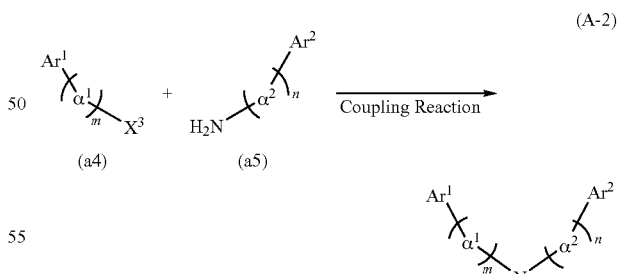

As shown in a scheme (A-3), a haloarylfluorene derivative (a3) and a diarylamine derivative (a6) are coupled, whereby the fluorene derivative represented by the above General Formula (G1) can be obtained.

[Chemical Formula 24]

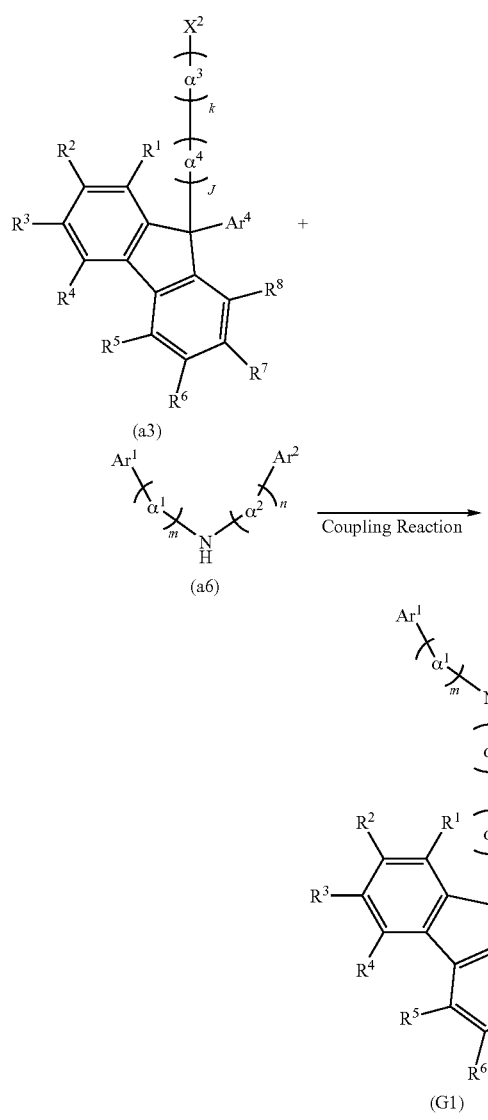

Note that $X^1$, $X^2$, or $X^3$ in the above schemes (A-1) to (A-3) represents halogen and preferably represents bromine or iodine, more preferably represents iodine because of high reaction.

In the schemes (A-2) and (A-3), a coupling reaction of an aryl compound including a halogen group and an aryl compound including amine (a primary arylamine compound or a secondary arylamine compound) has a variety of reaction conditions. As an example, a synthesis method using a metal catalyst in the presence of a base can be employed.

The case where a Buchwald-Hartwig reaction is performed in the schemes (A-2) and (A-3) is shown. A palladium catalyst can be used for the metal catalyst and a mixture of a palladium complex and a ligand thereof can be used for the palladium catalyst. As examples of the palladium catalyst, bis(dibenzylideneacetone)palladium(0), palladium(II) acetate, and the like can be given. As the ligand, tri(tert-butyl)phosphine, tri(n-hexyl)phosphine, tricyclohexylphosphine, 1,1-bis(diphenylphosphino)ferrocene (abbreviation: DPPF), and the like can be given. As a substance which can be used as the base, an organic base such as sodium tert-butoxide, an inorganic base such as potassium carbonate, and the like can be given. In addition, the above reaction is preferably performed in a solution, and toluene, xylene, benzene, and the like can be given as a solvent that can be used in the above reaction. However, the catalyst, ligand, base, and solvent which can be used are not limited thereto. In addition, the reaction is preferably performed under an inert atmosphere of nitrogen, argon, or the like.

The case where an Ullmann reaction is performed in the schemes (A-2) and (A-3) is shown. A copper catalyst can be used as the metal catalyst, and copper iodide (I) and copper acetate (II) can be given as the copper catalyst. As an example of a substance that can be used as the base, an inorganic base such as potassium carbonate can be given. The above reaction is preferably performed in a solution, and 1,3-dimethyl-3,4,5,6-tetrahydro-2(1H)-pyrimidinone (abbreviation: DMPU), toluene, xylene, benzene, and the like can be given as a solvent that can be used in the above reaction. However, the catalyst, ligand, base, and solvent which can be used are not limited thereto. In addition, the reaction is preferably performed under an inert atmosphere of nitrogen, argon, or the like.

Note that a solvent having a high boiling point such as DMPU or xylene is preferably used because, by an Ullmann reaction, an object can be obtained in a shorter time and at a higher yield when the reaction temperature is higher than or equal to 100° C. In particular, DMPU is more preferable because the reaction temperature is more preferably higher than or equal to 150° C.

<Synthesis Method 2 of the Fluorene Derivative Represented by General Formula (G1)>

For example, as shown in a scheme (B-1), the haloarylfluorene derivative (a3) and the arylamine derivative (a5) are coupled, whereby a diarylamine derivative having a fluorenyl group (b1) can be obtained.

[Chemical Formula 25]

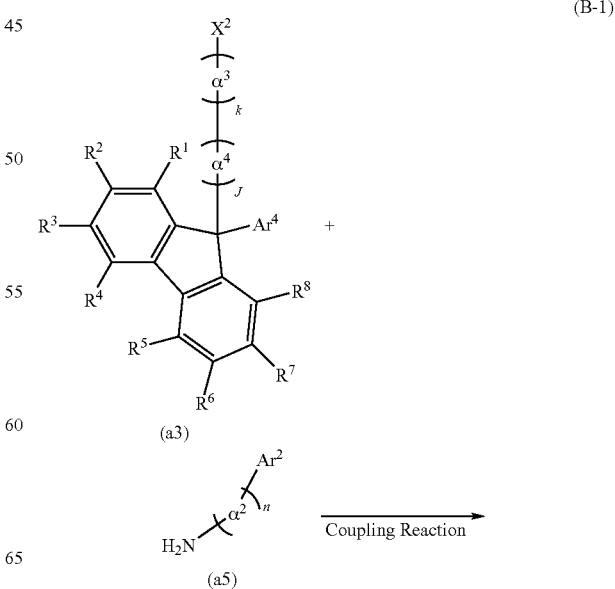

-continued

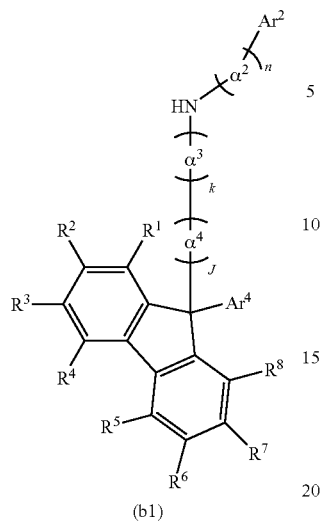

(b1)

-continued

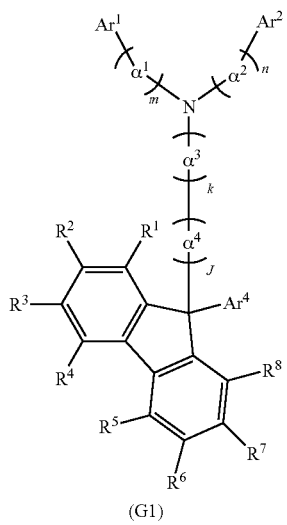

(G1)

As shown in a scheme (B-2), the diarylamine derivative having a fluorenyl group (b1) and the halogenated arene derivative (a-4) are coupled, whereby the fluorene derivative represented by the above General Formula (G1) can be obtained.

[Chemical Formula 26]

(B-2)

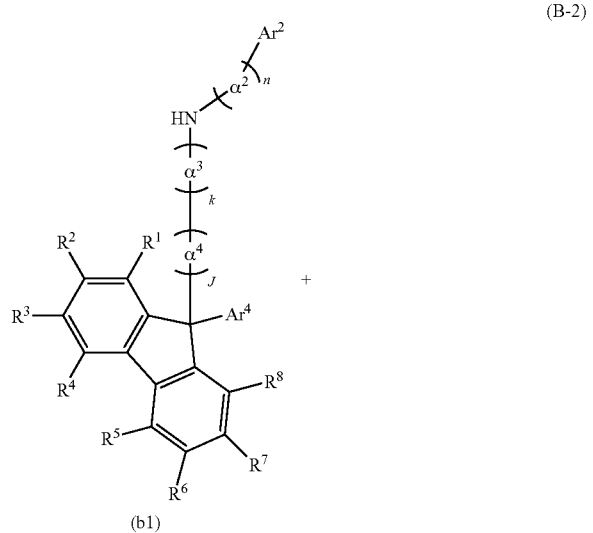

(b1)

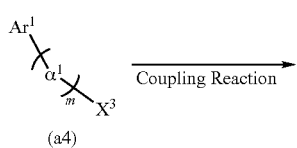

(a4)

Coupling Reaction →

Note that $X^2$ and $X^3$ in the above schemes (B-1) and (B-2) represent halogen and preferably represent bromine or iodine, more preferably represent iodine because of high reaction.

In the schemes (B-1) and (B-2), a coupling reaction of an aryl compound including a halogen group and an aryl compound including amine (a primary arylamine compound or a secondary arylamine compound) has a variety of reaction conditions. As an example, a synthesis method using a metal catalyst in the presence of a base can be employed.

The Buchwald-Hartwig reaction or the Ullmann reaction can be employed in the schemes (B-1) and (B-2) in a manner similar to the schemes (A-2) and (A-3).

<Synthesis Method 3 of the Fluorene Derivative Represented by General Formula (G1)>

For example, as shown in a scheme (C-1), a halogenated arylfluorene derivative (c1) is lithiated or made into a Grignard reagent and is reacted with an organoboronic acid, whereby an arylboronic acid derivative having a fluorenyl group (c2) can be obtained (Note that J represents 1.).

[Chemical Formula 27]

(C-1)

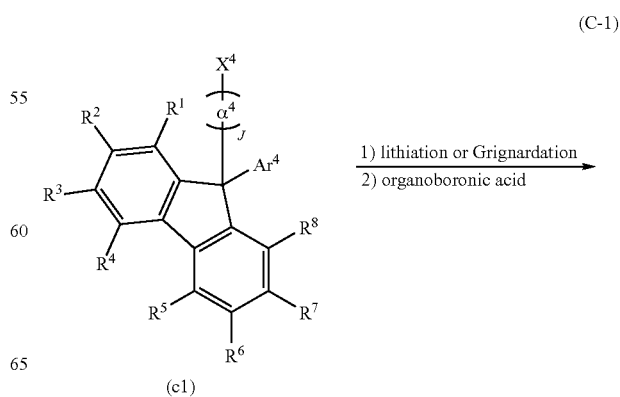

(c1)

1) lithiation or Grignardation
2) organoboronic acid →

-continued

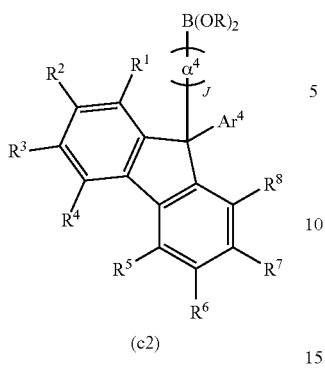

(c2)

As shown in a scheme (C-2), a triarylamine derivative (c3) is halogenated, whereby a halogenated triarylamine derivative (c4) can be obtained.

[Chemical Formula 28]

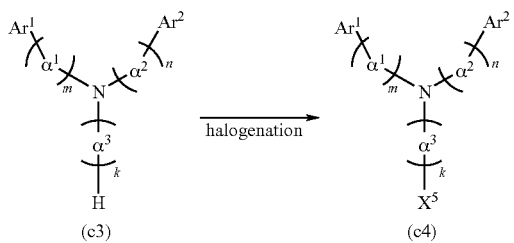

(C-2)

As shown in a scheme (C-3), the arylboronic acid derivative having a fluorenyl group (c2) and the halogenated triarylamine derivative (c4) are coupled, whereby the fluorene derivative represented by the above General Formula (G1) can be obtained.

[Chemical Formula 29]

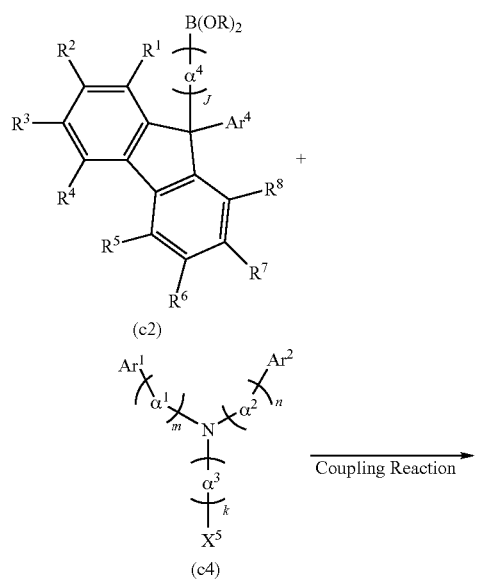

(C-3)

-continued (G1)

Note that k in the schemes (C-2) and (C-3) represents 1.

$X^4$ and $X^5$ in the above schemes (C-1) to (C-3) represent halogen and preferably represent bromine or iodine, more preferably represent iodine because of high reaction.

A reaction in the scheme (C-1) in which an aryl compound including a halogen group is used to obtain an aryl compound including a boronic acid group (or an organoboron group) has a variety of reaction conditions. $R^1$ to $R^8$ in the scheme represent hydrogen or an alkyl group.

As an example of the reaction, after an aryl compound including a halogen group is lithiated using an alkyllithium reagent, boron oxidation or organoboration of the aryl compound including a halogen group is performed adding a boron reagent. As the alkyllithium reagent, n-butyllithium, methyllithium, or the like can be used. As the boron reagent, Trimethyl borate, isopropyl borate, or the like can be used. As a dehydrating solvent, an ether such as diethyl ether or tetrahydrofuran (THF) can be used. Alternatively, a Grignard reagent with activated magnesium can be used instead of a lithiated reagent.

A halogenated reaction in the scheme (C-2) has a variety of reaction conditions. For example, a reaction in which a halogenating agent can used in the presence of a polar solvent can be used. As the halogenating agent, N-Bromosuccinimide (abbreviation: NBS), N-Iodosuccinimide (abbreviation: NIS), bromine, iodine, potassium iodide, or the like can be used. As the halogenating agent, the use of a bromide is preferable because synthesis can be performed at low cost. It is preferable to use an iodide as a halogenating agent because the reaction proceeds more easily in the case where a reaction using the generated object as a source is performed next (a portion which is replaced by iodine has a higher activation). Note that k in the scheme (C-2) represents 1 and halogenation peculiarly occurs at a para position with respect to amine.

A coupling reaction of an aryl compound including a halogen group and an aryl compound including a boronic acid (arylboronic acid) in the scheme (C-3) has a variety of reaction conditions. As an example thereof, a synthesis method using a metal catalyst in the presence of a base can be employed.

In the scheme (C-3), the case of using a Suzuki-Miyaura reaction is described. As the metal catalyst, a palladium catalyst such as a mixture of a palladium complex and the ligand thereof can be used. As the palladium catalyst, palladium(II) acetate, tetrakis(triphenylphosphine)palladium(0), bis(triphenylphosphine)palladium(II)dichloride, and the like can be given. As the ligand, tri(ortho-tolyl)phosphine, triphenylphosphine, tricyclohexylphosphine, and the like can be given. In addition, as the base, an organic base such as sodium tert-butoxide, an inorganic base such as potassium carbonate, and the like can be given. The reaction is preferably performed in a solution, and as the solvent which can be used, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of ethers such as ethyleneglycoldimethylether and water; and the like can be given. However, the catalyst, ligand, base, and solvent which can be used are not limited thereto. Alternatively, in the scheme, an organoboron compound of an aryl derivative, aryl aluminum, aryl zirconium, aryl zinc, aryl tin compound, or the like may be used instead of an arylboronic acid. In addition, the reaction is preferably performed under an inert atmosphere of nitrogen, argon, or the like.

(Embodiment 2)

In Embodiment 2, a light-emitting element which is formed using, for a hole-transport layer, the fluorene derivative of an embodiment of the present invention described in Embodiment 1 is described.

The light-emitting element in Embodiment 2 includes a first electrode which functions as an anode, a second electrode which functions as a cathode, and an EL layer interposed between the first electrode and the second electrode. Note that the light-emitting element in Embodiment 2 can exhibit light emission when voltage is applied to each electrode so that the potential of the first electrode is higher than that of the second electrode.

In addition, the EL layer of the light-emitting element in Embodiment 2 includes a first layer (hole-injection layer), a second layer (hole-transport layer), a third layer (light-emitting layer), a fourth layer (electron-transport layer), and a fifth layer (electron-injection layer), from the first electrode side.

Figure 1B:
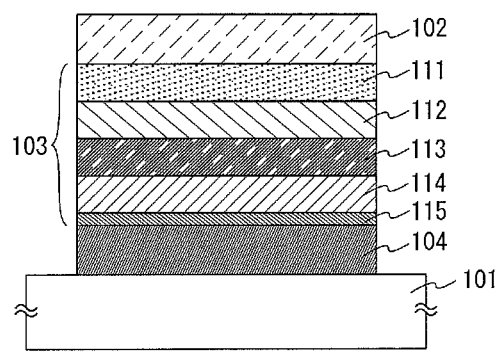

A structure of the light-emitting element in Embodiment 2 is described using FIGS. 1A and 1B. A substrate 101 is used as a support of the light-emitting element. For the substrate 101, glass, quartz, plastics, or the like can be used, for example.

Note that although the above substrate 101 may remain in a light-emitting device or an electronic device which is a product utilizing the light-emitting element of an embodiment of the present invention, the substrate 101 may only have a function as the support of the light-emitting element in the manufacturing process of the light-emitting element, without remaining in an end product.

For the first electrode 102 formed over the substrate 101, a metal, an alloy, an electrically conductive compound, a mixture thereof, or the like which has a high work function (specifically, a work function of 4.0 eV or more) is preferably used. Specific examples are given below: indium tin oxide (ITO), indium tin oxide containing silicon or silicon oxide, indium zinc oxide (IZO), and indium oxide containing tungsten oxide and zinc oxide. Besides, gold (Au), platinum (Pt), nickel (Ni), tungsten (W), chromium (Cr), molybdenum (Mo), iron (Fe), cobalt (Co), copper (Cu), palladium (Pd), titanium (Ti), nitride of metal materials (for example, titanium nitride), and the like can be given. Note that in the present invention, since the first layer 111 in the EL layer 103 which is formed in contact with the first electrode 102 includes a composite material which facilitates hole injection regardless of the work function of the first electrode 102, any known material can be used as long as the material can be used as an electrode material (e.g., a metal, an alloy, an electrically conductive compound, a mixture thereof, and an element belonging to Group 1 or Group 2 of the periodic table).

These materials are usually formed by a sputtering method. For example, a film of indium oxide-zinc oxide (IZO) can be formed by a sputtering method using a target in which 1 to 20 wt % zinc oxide is added to indium oxide; and a film of indium oxide containing tungsten oxide and zinc oxide can be formed by a sputtering method using a target in which 0.5 to 5 wt % tungsten oxide and 0.1 to 1 wt % zinc oxide are added to indium oxide. Alternatively, a vacuum evaporation method, a coating method, an inkjet method, a spin coating method, or the like may be used.

Further, in the EL layer 103 formed over the first electrode 102, when a composite material described later is used as a material for the first layer 111 formed in contact with the first electrode 102, any of a variety of metals, alloys, electrically conductive compounds, and a mixture thereof can be used as a substance used for the first electrode 102 regardless of whether the work function is high or low. For example, aluminum (Al), silver (Ag), an alloy containing aluminum (AlSi), or the like can also be used.

Alternatively, it is possible to use any of elements belonging to Group 1 and 2 of the periodic table, that is, alkali metals such as lithium (Li) and cesium (Cs), alkaline earth metals such as magnesium (Mg), calcium (Ca), and strontium (Sr), alloys containing them (e.g., MgAg and AlLi), rare earth metals such as europium (Eu) and ytterbium (Yb), alloys containing them, and the like which are materials with a low work function.

Note that in the case where the first electrode 102 is formed using an alkali metal, an alkaline earth metal, or an alloy thereof, a vacuum evaporation method or a sputtering method can be used. Further alternatively, in the case where a silver paste or the like is used, a coating method, an inkjet method, or the like can be used.

The EL layer 103 formed over the first electrode 102 can be formed using a known material, and either a low molecular compound or a high molecular compound can be used. Note that the substance forming the EL layer 103 is not limited to an organic compound and may partially include an inorganic compound.

The EL layer 103 is formed by stacking an appropriate combination of a hole-injection layer that includes a substance having a high hole-injection property, a hole-transport layer that includes a substance having a high hole-transport property, a light-emitting layer that includes a light-emitting substance, an electron-transport layer that includes a substance having a high electron-transport property, an electron-injection layer that includes a substance having a high electron-injection property, and the like.

Note that the EL layer 103 illustrated in FIG. 1A includes the first layer (hole-injection layer) 111, the second layer (hole-transport layer) 112, the third layer (light-emitting layer) 113, the fourth layer (electron-transport layer) 114, and the fifth layer (electron-injection layer) 115 which are in that order stacked from the first electrode 102 side.

The first layer 111 which is a hole-injection layer is a hole-injection layer that includes a substance having a high hole-injection property. As the substance having a high hole-injection property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, or the like can be used. Alternatively, as a low molecular organic compound, a phthalocyanine-based compound such as phthalocyanine (abbreviation: H₂Pc), copper(II) phthalocyanine (abbreviation: CuPc), or vanadyl phthalocyanine (abbreviation: VOPc) can be used. Note that the fluorene derivative of an embodiment of the present invention which is described in Embodiment 1 can also be used in a similar manner.

Further, as examples of low molecular organic compounds, there are aromatic amine compounds such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like. Note that the fluorene derivative of an embodiment of the present invention which is described in Embodiment 1 can also be used in a similar manner.

Further alternatively, any of high molecular compounds (e.g., oligomers, dendrimers, or polymers) can be used. For example, there are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD). Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

Moreover, for the first layer 111, the composite material in which an acceptor substance is mixed into a substance having a high hole-transport property can be used. By using such a substance with a high hole-transport property containing an acceptor substance, a material used to form an electrode may be selected regardless of its work function. In other words, besides a material with a high work function, a material with a low work function may also be used as the first electrode 102. Such a composite material can be formed by co-depositing a substance having a high hole-transport property and a substance having an acceptor property. Note that in this specification, the word "composite" means not only a state in which two materials are simply mixed but also a state in which a plurality of materials are mixed and charges are transferred between the materials.

As the organic compound for the composite material, a variety of compounds such as an aromatic amine compound, a carbazole derivative, aromatic hydrocarbon, and a high molecular compound (such as oligomer, dendrimer, or polymer) can be used. The organic compound used for the composite material is preferably an organic compound having a high hole-transport property. Specifically, a substance having a hole mobility of $10^{-6}$ cm²/Vs or higher is preferably used. However, any substance other than the above substances may also be used as long as it is a substance in which the hole-transport property is higher than the electron-transport property. The organic compounds which can be used for the composite material are specifically shown below.

For example, as the organic compounds that can be used for the composite material, there are aromatic amine compounds such as MTDATA, TDATA, DPAB, DNTPD, DPA3B, PCz-PCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl-2,3,5,6-tetraphenylbenzene. Note that the fluorene derivative of an embodiment of the present invention which is described in Embodiment 1 can also be used in a similar manner.

Further, there are aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Furthermore, there are aromatic hydrocarbon compounds such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

As a substance having an acceptor property, organic compounds such as 7,7,8,8-tetracyano-2,3,5,6-tetrafluoroquinodimethane (abbreviation: F₄-TCNQ) and chloranil, and a transition metal oxide can be given. In addition, oxides of metals belonging to Groups 4 to 8 in the periodic table can be also given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air and its hygroscopic property is low and is easily treated.

Note that for the first layer 111, a composite material formed using any of the above-mentioned high molecular compounds such as PVK, PVTPA, PTPDMA, or Poly-TPD and any of the above-mentioned acceptor substances may be used. Note that a composite material, which is formed combining the fluorene derivative of an embodiment of the present invention which is described in Embodiment 1 with the above substance having an acceptor property, can also be used for the first layer 111.

The second layer 112 which is a hole-transport layer includes a substance having a high hole-transport property. Note that the fluorene derivative of an embodiment of the present invention which is described in Embodiment 1 is used for the second layer 112 in Embodiment 2. Since the above fluorene derivative of an embodiment of the present invention has a wide band gap, the second layer 112 formed using the fluorene derivative hardly absorbs exciton energy generated in the third layer (light-emitting layer) 113 which is an adjacent to the second layer 112 and excitons can be efficiently confined in the light-emitting layer. Thus, a light-emitting element with high efficiency can be obtained.

Further, the fluorene derivative of an embodiment of the present invention which is described in Embodiment 1 can be used for both the first layer 111 and the second layer 112. In this case, an element can be easily formed and the use efficiency of the material can be improved. Moreover, since energy diagrams of the first layer 111 and the second layer 112 are the same or similar, carriers can be transported easily between the first layer 111 and the second layer 112.

The third layer 113 is a layer including a substance having a high light-emitting property. Low molecular organic compounds described below can be used for the third layer 113. Note that since the fluorene derivative of an embodiment of the present invention which is described in Embodiment 1 has a light-emitting property, the fluorene derivative can also be used as a light-emitting material.

As a light-emitting substance, for example, a fluorescent compound which emits fluorescence or a phosphorescent compound which emits phosphorescence can be used.

As a fluorescent compound which can be used for the light-emitting layer 113, for example, as a light-emitting substance for blue emission, there are N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like.

As a light-emitting substance for green emission, there are N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like.

As a light-emitting substance for yellow emission, there are rubrene, 5,12-bis(1,1'-biphenyl-4-yl)-6,11-diphenyltetracene (abbreviation: BPT), and the like. Furthermore, as a light-emitting substance for red emission, there are N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-α]fluoranthene-3,10-diamine (abbreviation: p-mPhAFD), and the like.

As a phosphorescent compound which can be used as the light-emitting layer 113, for example, as a substance for blue light emission, bis[2-(4',6'-difluorophenyl)pyridinato-N,$C^{2'}$] iridium(III) tetrakis(1-pyrazolyl)borate (abbreviation: FIr6), bis[2-(4',6'-difluorophenyl)pyridinato-N,$C^{2'}$]iridium(III)picolinate (abbreviation: FIrpic), bis{2-[3',5'-bis(trifluoromethyl)phenyl]pyridinato-N,$C^{2'}$}iridium(III)picolinate (abbreviation: Ir(CF$_3$ppy)$_2$(pic)); bis[2-(4',6'-difluorophenyl)pyridinato-N,$C^{2'}$]iridium(III) acetylacetonate (abbreviation: FIr(acac)), or the like can be given. As a substance for green light emission, tris(2-phenylpyridinato-N,$C^{2'}$)iridium(III) (abbreviation: Ir(ppy)$_3$), bis[2-phenylpyridinato-N,$C^{2'}$]iridium(III) acetylacetonate (abbreviation: Ir(ppy)$_2$(acac)), bis (1,2-diphenyl-1H-benzimidazolato)iridium(III)acetylacetonate (abbreviation: Ir(pbi)$_2$(acac)), bis(benzo[h]quinolinato)iridium(III)acetylacetonate (abbreviation: Ir(bzq)$_2$(acac)), or the like can be given. As a substance for yellow light emission, bis(2,4-diphenyl-1,3-oxazolato-N,$C^{2'}$)iridium(III) acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,$C^{2'}$)iridium(III)acetylacetonate (abbreviation: Ir(bt)$_2$(acac)), or the like can be given. As a substance for orange light emission, tris(2-phenylquinolinato-N,$C^{2'}$)iridium(III) (abbreviation: Ir(pq)$_3$, bis(2-phenylquinolinato-N,$C^{2'}$)iridium(III)acetylacetonate (abbreviation: Ir(pq)$_2$(acac)), or the like can be given. As a substance for red light emission, an organometallic complex such as bis[2-(2'-benzo[4,5-a]thienyl)pyridinato-N,$C^{3'}$]iridium(III)acetylacetonate (abbreviation: Ir(btp)$_2$(acac)), bis(1-phenylisoquinolinato-N,$C^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), 2,3,7,8,12,13,17,18-octaethyl-21H,23H-porphyrinatoplatinum(II) (abbreviation: PtOEP), or the like can be given. In addition, a rare earth metal complex such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), or tris[1-(2-thenoyl)-3,3,3-trifluoroacetonato](monophenanthroline)europium(III) (abbreviation: Eu(TTA)$_3$(Phen)) exhibits light emission from a rare earth metal ion (electron transition between different multiplicities); therefore, such a rare earth metal complex can be used as a phosphorescent compound.

The third layer 113 may have a structure in which the above-described substance having a high light-emitting property is dispersed in another substance. Note that in the case of the dispersing, the concentration of the substance to be dispersed (a dopant) is preferably 20% or less of the total in mass ratio. Further, as a substance in which the substance having a light-emitting property is dispersed (a host), a known substance can be used. It is preferable to use a substance having a lowest unoccupied molecular orbital level (LUMO level) shallower (the absolute value is smaller) than that of the substance having a light-emitting property and having a highest occupied molecular orbital level (HOMO level) deeper (the absolute value is larger) than that of the substance having a light-emitting property (the dopant). Further, it is preferable that the band gap (Bg: a difference between a HOMO level and a LUMO level) of the host be larger than the Bg of the dopant having a light-emitting property. Furthermore, when the light emitted from the dopant is fluorescent, in the Si level, the dopant is preferably higher than the host, and when the light emitted from the dopant is phosphorescent, in the T1 level, the dopant is preferably higher than the host.

Specifically, a metal complex such as tris(8-quinolinolato) aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq2), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ) can be used.

In addition, a heterocyclic compound such as 2-(biphenyl-4-yl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(biphenyl-4-yl)-4-phenyl-5-(4-tert-butylphenyl)-1,2,4-triazole(abbreviation: TAZ), 2,2',2"-(1,3,5-benzenetriyl)tris(1-phenyl-1H-benzimidazole) (abbreviation: TPBI), bathophenanthroline (abbreviation: BPhen), or bathocuproine (BCP) can be used.

Alternatively, a condensed aromatic compound such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)

diphenanthrene (abbreviation: DPNS), 9,9'-(stilbene-4,4'-diyl)diphenanthrene (abbreviation: DPNS2), or 3,3',3''-(benzene-1,3,5-triyl)tripyrene (abbreviation: TPB3) can also be used.

As a substance in which the substance having a light-emitting property is dispersed, a plurality of kinds of substances can be used. For example, in order to suppress crystallization, a substance such as rubrene which suppresses crystallization, may be further added. In addition, NPB, Alq, or the like can be further added in order to efficiently transfer energy to the substance having a light-emitting property. Note that the fluorene derivative of an embodiment of the present invention which is described in Embodiment 1 can be used. With a structure in which a substance having a high light-emitting property is thus dispersed in another substance, crystallization of the third layer 113 can be suppressed. Further, concentration quenching which results from the high concentration of the substance having a high light-emitting property can also be suppressed.

Further, in particular, among the above-described substances, a substance having an electron-transport property is preferably used so that a substance having a light-emitting property is dispersed therein to form the third layer 113. Specifically, it is also possible to use any of the above metal complexes and heterocyclic compounds; CzPA, DNA, and t-BuDNA among the above condensed aromatic compounds; and further macromolecular compounds which will be given later as a substance that can be used for the fourth layer 114.

Alternatively, for the third layer 113, high molecular compounds given below can also be used.

As a light-emitting substance for blue emission, there are poly(9,9-dioctylfluorene-2,7-diyl) (abbreviation: PFO), poly[(9,9-dioctylfluorene-2,7-diyl-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like.

As a light-emitting substance for green emission, there are poly(p-phenylenevinylene) (abbreviation: PPV), poly[(9,9-dihexylfluorene-2,7-diyl)-alt-co-(benzo[2,1,3]thiadiazol-4,7-diyl)] (abbreviation: PFBT), poly[(9,9-dioctyl-2,7-divinylenefluorenylene)-alt-co-(2-methoxy-5-(2-ethylhexyloxy)-1, 4-phenylene)], and the like.

As a light-emitting substance for orange to red emission, there are poly[2-methoxy-5-(2'-ethylhexoxy)-1,4-phenylenevinylene] (abbreviation: MEH-PPV), poly(3-butylthiophene-2,5-diyl) (abbreviation: $R^4$-PAT), poly{[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like.

The light-emitting layer 113 may be a stack of two or more layers. For example, in the case where the light-emitting layer 113 is formed by stacking a first light-emitting layer and a second light-emitting layer in that order from the hole transport layer side, the first light-emitting layer can be formed using a substance having a hole transport property as the host material and the second light-emitting layer can be formed using a substance having an electron transport property as the host material. It is more preferable that a material in which the hole-transport property is higher than the electron-transport property be used for the host material of the first light-emitting layer and a material in which the electron-transport property is higher than the hole-transport property be used for the host material of the second light-emitting layer. With the above structure, a light emission site is formed between the first light-emitting layer and the second light-emitting layer, whereby an element having higher efficiency can be obtained.

When the light-emitting layer having the structure described above is formed using a plurality of materials, the light-emitting layer can be formed using co-evaporation by a vacuum evaporation method; or an ink-jet method, a spin coating method, a dip coating method, or the like as a method for mixing a solution.

The fourth layer 114 is an electron-transport layer that includes a substance having a high electron-transport property. For the fourth layer 114, for example, as a low molecular organic compound, a metal complex such as Alq, Almq$_3$, BeBq2, BAlq, Znq, ZnPBO, or ZnBTZ can be used. Alternatively, instead of the metal complex, a heterocyclic compound such as PBD, OXD-7, TAZ, TPBI, BPhen, or BCP can be used. The substances mentioned here are mainly ones that have an electron mobility of $10^{-6}$ cm$^2$/Vs or higher. Note that any substance other than the above substances may be used for the electron-transport layer as long as it is a substance in which the electron-transport property is higher than the hole-transport property. Furthermore, the electron transport layer is not limited to a single layer, and two or more layers made of the aforementioned substances may be stacked.

For the fourth layer 114, a high molecular compound can also be used. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridin-6,6'-diyl)] (abbreviation: PF-BPy), or the like can be used.

The fifth layer 115 is an electron-inject layer that includes a substance having a high electron-inject property. For the fifth layer 115, an alkali metal, an alkaline earth metal, or a compound thereof, such as lithium fluoride (LiF), cesium fluoride (CsF), or calcium fluoride (CaF$_2$), can be used. Alternatively, a layer of an electron-transport substance which contains an alkali metal, an alkaline earth metal, or a compound thereof, specifically, a layer of Alq which contains magnesium (Mg), or the like may be used. Note that in this case, electrons can be more efficiently injected from the second electrode 104.

For the second electrode 104, a metal, an alloy, an electrically conductive compound, a mixture thereof, or the like which has a low work function (specifically, a work function of 3.8 eV or less) can be used. As a specific example of such a cathode material, an element that belongs to Group 1 or 2 of the periodic table, that is, alkali metals such as lithium (Li) and cesium (Cs), alkaline earth metals such as magnesium (Mg), calcium (Ca), and strontium (Sr), alloys containing these (e.g., MgAg and AlLi), rare earth metals such as europium (Eu) and ytterbium (Yb), alloys containing these, and the like can be given.

Note that in the case where the second electrode 104 is formed using an alkali metal, an alkaline earth metal, or an alloy thereof, a vacuum evaporation method or a sputtering method can be used. In the case of using a silver paste or the like, a coating method, an inkjet method, or the like can be used Note that by provision of the fifth layer 115, the second electrode 104 can be formed using any of a variety of conductive materials such as Al, Ag, ITO, and indium oxide-tin oxide containing silicon or silicon oxide regardless of the work functions. A film of such a conductive material can be formed by a sputtering method, an inkjet method, a spin coating method, or the like.

Further, as a formation method of the EL layer 103 in which the first layer (hole-injection layer) 111, the second layer (hole-transport layer) 112, the third layer (light-emitting layer) 113, the fourth layer (electron-transport layer)

114, and the fifth layer (electron-injection layer) 115 are in that order stacked, any of a variety of methods can be employed regardless of whether the method is a dry process or a wet process. For example, a vacuum evaporation method, an inkjet method, a spin coating method, or the like can be used. Note that a different formation method may be employed for each layer.

The second electrode 104 can also be formed by a wet process such as a sol-gel method using a paste of a metal material instead of a dry process such as a sputtering method or a vacuum evaporation method.

Since holes mainly flow between the first electrode 102 and the first layer (hole-injection layer) 111, between the first layer (hole-injection layer) 111 and the second layer (hole-transport layer) 112, and between the second layer (hole-transport layer) 112 and the third layer (light-emitting layer) 113, the HOMO levels (work function in a case of metal) thereof are preferably the same or almost the same to reduce the carrier injection barrier between the adjacent layers. Similarly, electrons mainly flow between the third layer (light-emitting layer) 113 and the fourth layer (electron-transport layer) 114, between the fourth layer (electron-transport layer) 114 and the fifth layer (electron-injection layer) 115, and between the fifth layer (electron-injection layer) 115 and the second electrode 104, the LUMO levels (work function in a case of metal) thereof are preferably the same or almost the same to reduce the carrier injection barrier between the adjacent layers. The difference is preferably less than or equal to 0.2 eV, more preferably less than or equal to 0.1 eV.

It is preferable that a difference in the HOMO level between the second layer (hole-transport layer) 112 and the third layer (light-emitting layer) 113 and a difference in the LUMO level between the third layer (light-emitting layer) 113 and the fourth layer (electron-transport layer) 114 be increased to confine carriers in the light-emitting layer, so that a light-emitting element with higher efficiency can be obtained. Note that in this case, when a barrier is too high, a driving voltage is high, which becomes a burden on the element. Therefore, each the difference is preferably less than or equal to 0.4 eV, more preferably less than or equal to 0.2 eV.

In the above-described light-emitting element of an embodiment of the present invention, a current flows because of a potential difference generated between the first electrode 102 and the second electrode 104 and holes and electrons recombine in the EL layer 103, so that light is emitted. Then, this emitted light is extracted out through one or both of the first electrode 102 and the second electrode 104. Accordingly, one of or both the first electrode 102 and the second electrode 104 is/are an electrode having a light-transmitting property.

Figure 2A:
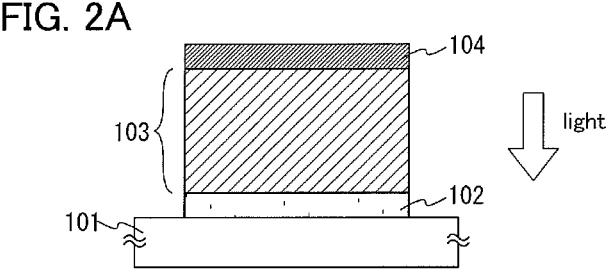
FIGS. 2A to 2C are views each illustrating a light-emitting element.
Figure 2B:
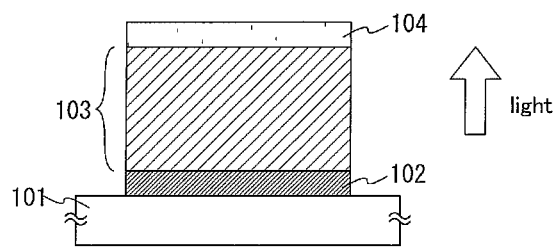
Figure 2C:
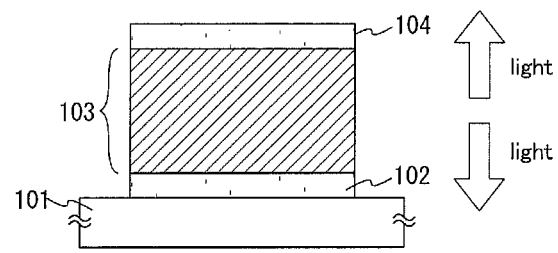

As illustrated in FIG. 2A, when only the first electrode 102 has a light-transmitting property, the emitted light is extracted from a substrate side through the first electrode 102. Alternatively, as illustrated in FIG. 2B, when only the second electrode 104 has a light-transmitting property, the emitted light is extracted from the side opposite to the substrate 101 through the second electrode 104. As illustrated in FIG. 2C, when each of the first electrode 102 and the second electrode 104 has a light-transmitting property, the emitted light is extracted from both the substrate 101 side and the side opposite to the substrate 101 side through the first electrode 102 and the second electrode 104.

The structure of the layers provided between the first electrode 102 and the second electrode 104 is not limited to the aforementioned one. Structures other than the above may be employed as long as at least the second layer 112 which is a hole-transport layer and the third layer 113 which is a light-emitting layer are included.

Alternatively, as illustrated in FIG. 1B, a structure may be employed in which the second electrode 104 functioning as a cathode, the EL layer 103, and the first electrode 102 functioning as an anode are stacked in that order over the substrate 101. Note that the EL layer 103 in this case has a structure in which the fifth layer 115, the fourth layer 114, the third layer 113, the second layer 112, the first layer 111, and the first electrode 102 are stacked in that order over the second electrode 104.

Note that by use of the light-emitting element of the present invention, a passive matrix light-emitting device or an active matrix light-emitting device in which drive of the light-emitting element is controlled by a thin film transistor (TFT) can be fabricated.

Note that there is no particular limitation on the structure of the TFT in the case of fabricating an active matrix light-emitting device. For example, a staggered TFT or an inverted staggered TFT can be used as appropriate. Further, a driver circuit formed over a TFT substrate may be formed using both of an n-type TFT and a p-type TFT or only either an n-type TFT or a p-type TFT. Furthermore, there is no particular limitation on the crystallinity of a semiconductor film used for the TFT. An amorphous semiconductor film may be used, or a crystalline semiconductor film may be used.

Since the second layer (hole-transport layer) 112 is formed using the fluorene derivative of an embodiment of the present invention, in the light-emitting element which is described in Embodiment 2, not only improvement in element efficiency but also suppression of power consumption can be realized.

(Embodiment 3)

In Embodiment 3, a mode of a light-emitting element having a structure in which a plurality of light-emitting units (also referred to as EL layers) is stacked (hereinafter, referred to as a stacked-type element) is described with reference to FIGS. 3A and 3B. The light-emitting element is a stacked-type light-emitting element including a plurality of light-emitting units between a first electrode and a second electrode. Each structure of the light-emitting units can be similar to that described in Embodiment 2. In other words, the light-emitting element described in Embodiment 2 is a light-emitting element having one light-emitting unit. In Embodiment 3, a light-emitting element having a plurality of light-emitting units is described.

Figure 3A:
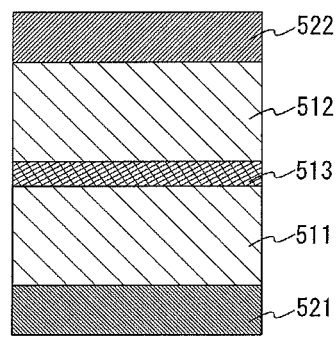
FIGS. 3A and 3B are views each illustrating a light-emitting element.

In FIG. 3A, a first light-emitting unit 511 and a second light-emitting unit 512 are stacked between a first electrode 521 and a second electrode 522. The first electrode 521 and the second electrode 522 can be similar to those in Embodiment 2. The first light-emitting unit 511 and the second light-emitting unit 512 may have the same structure or different structures, and a structure similar to those described in Embodiment 2 can be employed.

A charge-generation layer 513 is a layer which injects electrons into the light-emitting unit on one side and injects holes into the light-emitting unit on the other side when voltage is applied to the first electrode 521 and the second electrode 522, and may have either a single layer structure or a stacked structure of plural layers. As a stacked structure of plural layers, a structure in which a layer that injects holes and a layer that injects electrons are stacked is preferable.

As the layer that injects holes, a semiconductor or an insulator, such as molybdenum oxide, vanadium oxide, rhenium oxide, or ruthenium oxide, can be used. Alternatively, the layer that injects holes may have a structure in which an acceptor substance is added to a substance having a high hole-transport property. The layer including a substance having a high hole-transport property and an acceptor substance includes, as an acceptor substance, 7,7,8,8-tetracyano-2,3,5, 6-tetrafluoroquinodimethane (abbreviation: $F_4$-TCNQ) or metal oxide such as vanadium oxide, molybdenum oxide, or tungsten oxide. As the substance having a high hole-transport property, a variety of compounds such as an aromatic amine compound, a carbazole derivative, aromatic hydrocarbon, a high-molecular compound, oligomer, dendrimer, polymer, and the like can be used. Note that the fluorene derivative of an embodiment of the present invention which is described in Embodiment 1 can also be used in a similar manner. Note that a substance having a hole mobility of $10^{-6}$ $cm^2$/Vs or higher is preferably employed as the substance having a high hole-transport property. However, any substance other than the above substances may also be used as long as it is a substance in which the hole-transport property is higher than the electron-transport property. Since the composite material of the substance having a high hole-transport property and the acceptor substance has an excellent carrier-injection property and an excellent carrier-transport property, low-voltage driving and low-current driving can be realized.

As the layer that injects electrons, a semiconductor or an insulator, such as lithium oxide, lithium fluoride, or cesium carbonate, can be used. Alternatively, the hole-injection layer may have a structure in which a donor substance is added to a substance having a high hole-transport property. As the donor substance, an alkali metal, an alkaline earth metal, a rare-earth metal, a metal that belongs to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance. As the substance having a high electron-transport property, the materials described in Embodiment 1 can be used. Note that a substance having a hole mobility of $10^{-6}$ $cm^2$/Vs or higher is preferably employed as the substance having a high hole-transport property. However, any substance other than the above substances may also be used as long as it is a substance in which the electron-transport property is higher than the hole-transport property. Since the composite material of the substance having a high hole-transport property and the donor substance has an excellent carrier-injection property and an excellent carrier-transport property, low-voltage driving and low-current driving can be realized.

Further, the electrode materials described in Embodiment 2 can be used for the charge-generation layer 513. For example, the charge-generation layer 513 may be formed with a combination of a layer including a substance having a high hole-transport property and metal oxide and a transparent conductive film. It is preferable that the charge-generation layer 513 be a highly light-transmitting layer in terms of light extraction efficiency.

In any case, the charge-generation layer 513, which is interposed between the first light-emitting unit 511 and the second light-emitting unit 512, is acceptable as long as a layer which injects electrons into the light-emitting unit on one side and injects holes into the light-emitting unit on the other side when voltage is applied to the first electrode 521 and the second electrode 522. For example, any structure is acceptable for the charge-generation layer 513 as long as the charge-generation layer 513 injects electrons and holes into the first light-emitting unit 511 and the second light-emitting unit 512, respectively, when voltage is applied so that the potential of the first electrode is higher than the potential of the second electrode.

Figure 3B:
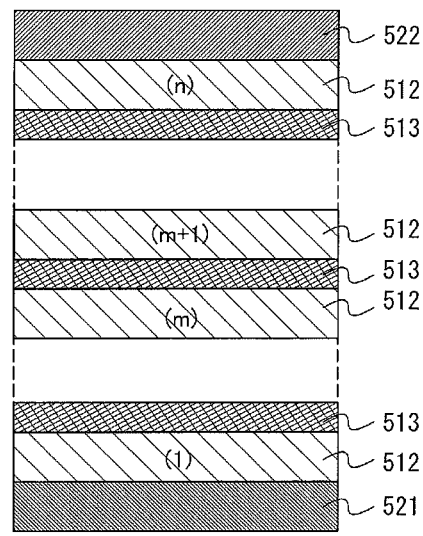

In Embodiment 3, the light-emitting element having two light-emitting units is described; however, an embodiment of the present invention can be similarly applied to a light-emitting element in which three or more light-emitting units are stacked as illustrated in FIG. 3B. By arrangement of a plurality of light-emitting units, which are partitioned by the charge-generation layer 513 between a pair of electrodes, as in the light-emitting element of Embodiment 3, light emission in a high luminance region can be achieved with current density kept low, thus light-emitting having long lifetime can be realized. When the light-emitting element is applied for a lighting device as an application example, voltage drop due to resistance of an electrode material can be reduced, thereby achieving homogeneous light emission in a large area. Moreover, a light-emitting device with low power consumption, which can be driven at low voltage, can be achieved.

The light-emitting units emit light having different colors from each other, thereby obtaining light emission of a desired color as the whole light-emitting element. For example, in a light-emitting element having two light-emitting units, the emission colors of the first light-emitting unit and the second light-emitting unit are made complementary, so that the light-emitting element which emits white light as the whole light-emitting element can be obtained. Note that the word "complementary" means color relationship in which an achromatic color is obtained when colors are mixed. That is, white light emission can be obtained by mixture of light obtained from substances emitting the lights of complementary colors. The same can be applied to a light-emitting element which has three light-emitting units. For example, the light-emitting element as a whole can provide white light emission when the emission color of the first light-emitting unit is red, the emission color of the second light-emitting unit is green, and the emission color of the third light-emitting unit is blue.

Note that Embodiment 3 can be combined with any other embodiment as appropriate.

(Embodiment 4)

Figure 4A:
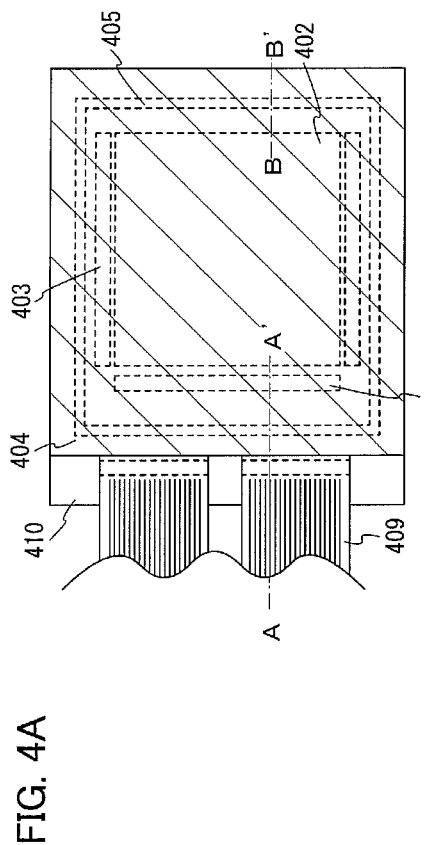
FIGS. 4A and 4B are views illustrating a light-emitting device.
Figure 4B:
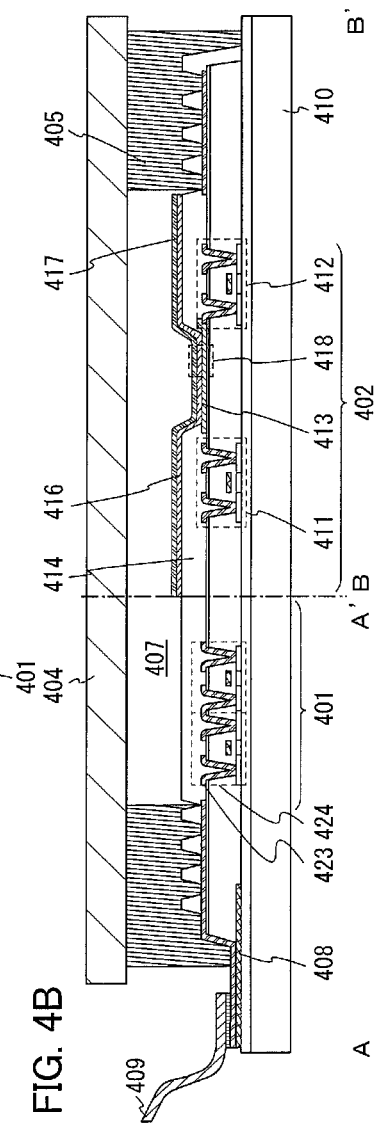

In Embodiment 4, a light-emitting device having a light-emitting element of the present invention in a pixel portion is described with reference to FIGS. 4A and 4B. FIG. 4A is a top view illustrating a light-emitting device while FIG. 4B is a cross-sectional view taken along lines A-A' and B-B' of FIG. 4A.

In FIG. 4A, reference numeral 401 denotes a driver circuit portion (a source side driver circuit), reference numeral 402 denotes a pixel portion, and reference numeral 403 denotes a driver circuit portion (a gate side driver circuit), which are shown by a dotted line. Reference numeral 404 denotes a sealing substrate, reference numeral 405 denotes a sealant, and a portion enclosed by the sealant 405 is a space 407.

Note that a lead wiring 408 is a wiring for transmitting signals that are to be inputted to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure is described with reference to FIG. 4B. The driver circuit portion and the pixel portion are formed over an element substrate 410. In this case, one pixel in the pixel portion 402 and the source side driver circuit 401 which is the driver circuit portion are illustrated. A CMOS circuit, which is a combination of an n-channel TFT 423 with a p-channel TFT 424, is formed as the source side driver circuit 401. Such a driver circuit may be formed using a variety of circuits such as a CMOS circuit, a PMOS circuit, or an NMOS circuit. Although a driver-integrated type in which a driver circuit is formed over the substrate is described in Embodiment 4, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413.

In order to improve the coverage, the insulator 414 is preferably provided such that either an upper end portion or a lower end portion of the insulator 414 has a curved surface with a curvature. For example, when positive photosensitive acrylic is used as a material for the insulator 414, only an upper end portion of the insulator 414 can have a curved surface with a radius of curvature (0.2 μm to 3 μm). Alternatively, the insulator 414 can be formed using either a negative type photosensitive material that becomes insoluble in an etchant by light irradiation or a positive type photosensitive material that becomes soluble in an etchant by light irradiation.

Over the first electrode 413, an EL layer 416 and a second electrode 417 are formed. In this case, the first electrode 413 can be formed using any of a variety of materials such as metals, alloys, and electrically conductive compounds or a mixture thereof. Note that as specific materials, the materials described in Embodiment 2 as a material that can be used for the first electrode can be used.

The EL layer 416 is formed by any of a variety of methods such as an evaporation method using an evaporation mask, an inkjet method, and a spin coating method. The EL layer 416 has any of the structures described in Embodiment 2. Further, as another material included in the EL layer 416, low molecular compounds or high molecular compounds (including oligomers and dendrimers) may be used. As the material for the EL layer, not only an organic compound but also an inorganic compound may be used.

The second electrode 417 can be formed using any of a variety of metals, alloys, and electrically conductive compounds, or a mixture thereof. Among such materials, a metal, an alloy, an electrically conductive compound, a mixture thereof, or the like having a low work function (a work function of 3.8 eV or less) is preferably used when the second electrode 417 is used as a cathode. As an example, an element belonging to Group 1 or Group 2 in the periodic table, i.e., an alkali metal such as lithium (Li) or cesium (Cs), an alkaline earth metal such as magnesium (Mg), calcium (Ca), or strontium (Sr), an alloy containing any of these (e.g., MgAg and AlLi) and the like can be given.

Note that when light generated in the EL layer 416 is transmitted through the second electrode 417, the second electrode 417 can be formed using a stack of a thin metal film with a small thickness and a transparent conductive film (indium oxide-tin oxide (ITO), indium oxide-tin oxide containing silicon or silicon oxide, indium oxide-zinc oxide (IZO), indium oxide containing tungsten oxide and zinc oxide, or the like).

The sealing substrate 404 is attached to the element substrate 410 with the sealant 405; thus, a light-emitting element 418 is provided in the space 407 enclosed by the element substrate 410, the sealing substrate 404, and the sealant 405. It is to be noted that the space 407 is filled with a filler such as an inert gas (e.g., nitrogen or argon) or the sealant 405.

Note that as the sealant 405, an epoxy-based resin is preferably used. A material used for these is desirably a material which does not transmit moisture or oxygen as possible. As a material for the sealing substrate 404, a glass substrate, a quartz substrate, or a plastic substrate including fiberglass-reinforced plastics (FRP), polyvinyl fluoride (PVF), polyester, acrylic, or the like can be used.

As described above, the active matrix light-emitting device having the light-emitting element of the present invention can be obtained.

Figure 5A:
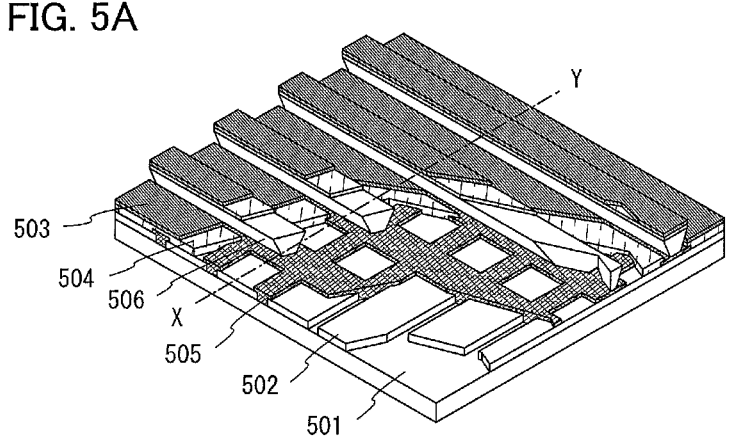
FIGS. 5A and 5B are views illustrating a light-emitting device.
Figure 5B:
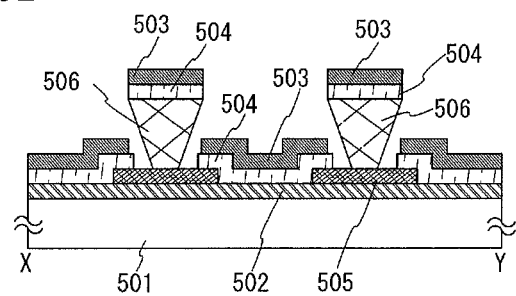

Further, the light-emitting element of the present invention can be used for a passive matrix light-emitting device instead of the above active matrix light-emitting device. FIGS. 5A and 5B illustrate a perspective view and a cross-sectional view of a passive matrix light-emitting device using the light-emitting element of the present invention. FIG. 5A is a perspective view of the light-emitting device, and FIG. 5B is a cross-sectional view taken along line X-Y of FIG. 5A.

In FIGS. 5A and 5B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 are a slope so that a distance between both sidewalls is gradually narrowed toward the surface of the substrate. In other words, a cross section taken along the direction of the short side of the partition layer 506 is trapezoidal, and the lower side (a side in contact with the insulating layer 505 which is one of a pair of parallel sides of the trapezoidal cross section) is shorter than the upper side (a side not in contact with the insulating layer 505 which is the other of the pair of parallel sides). By provision of the partition layer 506 in such a manner, a defect of the light-emitting element due to static electricity or the like can be prevented.

Accordingly, the passive matrix light-emitting device having the light-emitting element of the present invention can be obtained.

Note that any of the light-emitting devices described in Embodiment 4 (the active matrix light-emitting device and the passive matrix light-emitting device) are formed using the light-emitting element of the present invention, which has high luminous efficiency, and accordingly a light-emitting device with low power consumption can be obtained.

Note that in Embodiment 4, an appropriate combination of the structures described in Embodiments 1 to 3 can be used.

(Embodiment 5)

In Embodiment 5, electronic devices including the light-emitting device of the present invention which is described in Embodiment 4 are described. Examples of the electronic devices include cameras such as video cameras and digital cameras, goggle type displays, navigation systems, audio reproducing devices (e.g., car audio systems and audio systems), computers, game machines, portable information terminals (e.g., mobile computers, cellular phones, portable game machines, and electronic book readers), image reproducing devices in which a recording medium is provided (specifically, devices that are capable of reproducing recording media such as digital versatile discs (DVDs) and provided with a display device that can display an image), and the like. Specific examples of these electronic devices are shown in FIGS. 6A to 6D.

Figure 6A:
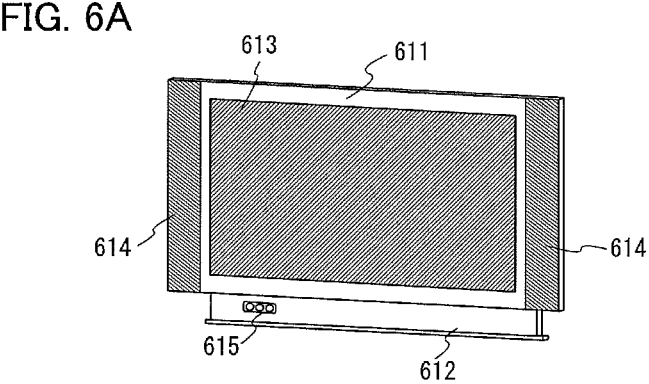
FIGS. 6A to 6D are views illustrating electronic devices.

FIG. 6A illustrates a television set according to an embodiment of the present invention, which includes a housing 611, a supporting base 612, a display portion 613, speaker portions 614, video input terminals 615, and the like. In this television set, the light-emitting device of the present invention can be applied to the display portion 613. Since the light-emitting device of the present invention has a feature of high luminous efficiency, a television set with low power consumption can be obtained by application of the light-emitting device of the present invention.

Figure 6B:
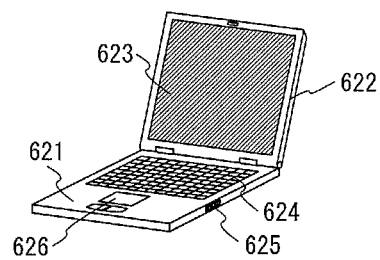

FIG. 6B illustrates a computer according to an embodiment of the present invention, which includes a main body 621, a housing 622, a display portion 623, a keyboard 624, an external connection port 625, a pointing device 626, and the like. In this computer, the light-emitting device of the present invention can be applied to the display portion 623. Since the light-emitting device of the present invention has a feature of high luminous efficiency, a computer with low power consumption can be obtained by application of the light-emitting device of the present invention.

Figure 6C:
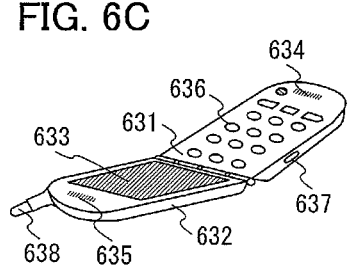

FIG. 6C shows a cellular phone according to an embodiment of the present invention, which includes a main body 631, a housing 632, a display portion 633, an audio input portion 634, an audio output portion 635, operation keys 636, an external connection port 637, an antenna 638, and the like. In this cellular phone, the light-emitting device of the present invention can be applied to the display portion 633. Since the light-emitting device of the present invention has a feature of high luminous efficiency, a cellular phone having reduced power consumption can be obtained by application of the light-emitting device of the present invention.

Figure 6D:
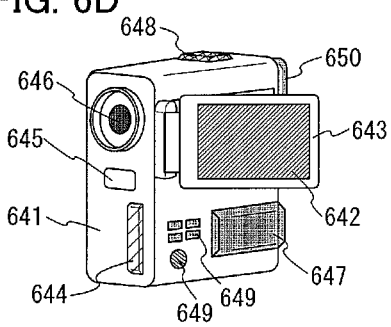

FIG. 6D shows a camera according to an embodiment of the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, the light-emitting device of the present invention can be applied to the display portion 642. Since the light-emitting device of the present invention has a feature of high luminous efficiency, a camera having reduced power consumption can be obtained by application of the light-emitting device of the present invention.

As thus described, application range of the light-emitting device of the present invention is quite wide, and this light-emitting device can be applied to electronic devices of a variety of fields. With use of the light-emitting device of the present invention, an electronic device having reduced power consumption can be obtained.

Figure 7:
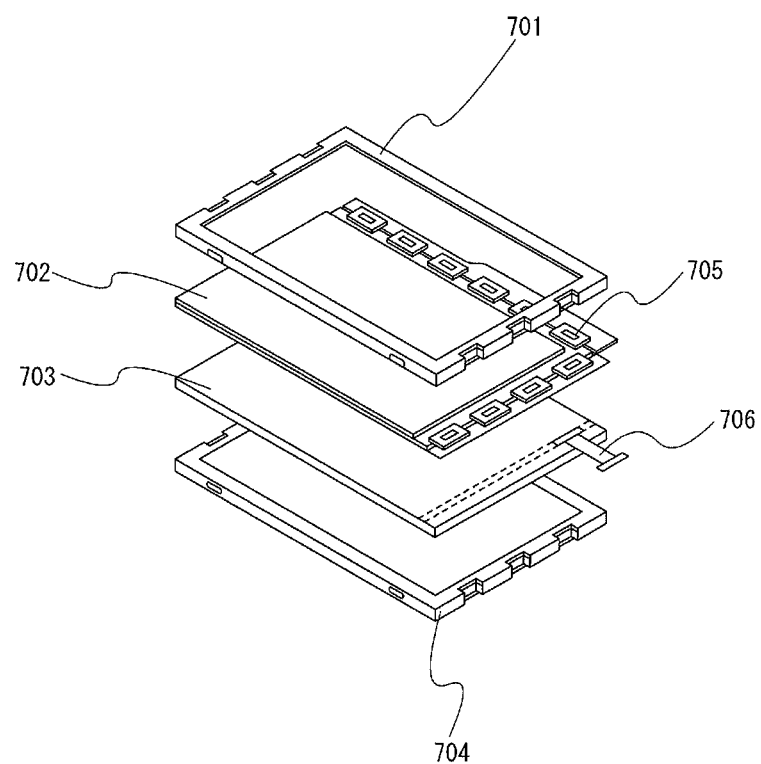
FIG. 7 is a view illustrating an electronic device.

Moreover, the light-emitting device of the present invention can be used as a lighting device. FIG. 7 shows an example of a liquid crystal display device in which the light-emitting device of the present invention is used as a backlight. The liquid crystal display device illustrated in FIG. 7 includes a housing 701, a liquid crystal layer 702, a backlight 703, and a housing 704. The liquid crystal layer 702 is connected to a driver IC 705. The light-emitting device of the present invention is used for the backlight 703, and current is supplied through a terminal 706.

By using the light-emitting device of the present invention as a backlight of a liquid crystal display device as described above, a backlight with low power consumption can be obtained. Further, since the light-emitting device of the present invention is a surface emitting lighting device and can be formed to have a large area, a larger-area backlight can also be obtained. Accordingly, a larger-area liquid crystal display device with low power consumption can be obtained.

Figure 8:
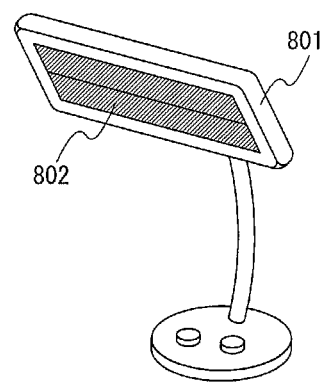
FIG. 8 is a view illustrating a lighting device.

FIG. 8 illustrates an example in which the light-emitting device of the present invention is used as a desk lamp, which is a lighting device. The desk lamp illustrated in FIG. 8 has a housing 801 and a light source 802, and the light-emitting device of the present invention is used as the light source 802. The light-emitting device of the present invention has the light-emitting element having high luminous efficiency and therefore can be used as a desk lamp with low power consumption.

Figure 9:
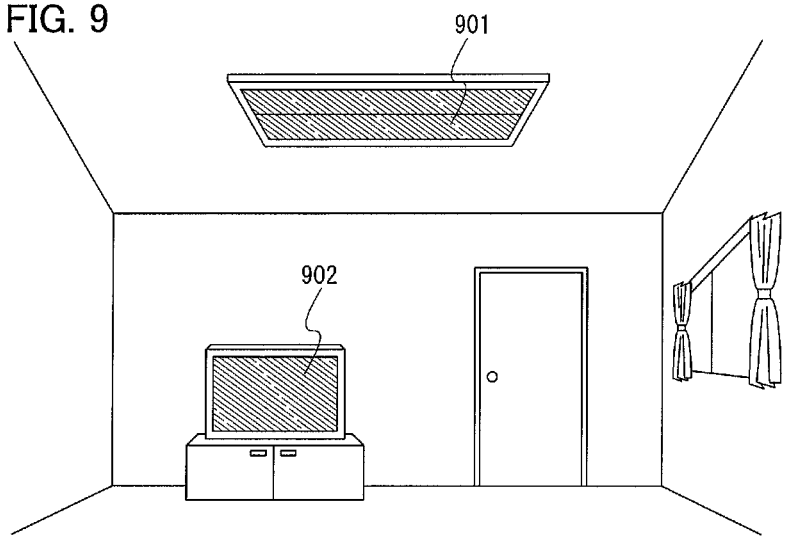
FIG. 9 is a view illustrating a lighting device.

FIG. 9 illustrates an example in which a light-emitting device to which the present invention is applied is used as an interior lighting device 901. Since the light-emitting device of the present invention can be enlarged, the light-emitting device can be used as a large-area lighting device. Further, the light-emitting device of the present invention has the light-emitting element having high luminous efficiency and therefore can be used as a lighting device with low power consumption. In a room where a light-emitting device to which the present invention is applied is thus used as the interior lighting device 901, a television set 902 according to the present invention as described with reference to FIG. 6A may be placed, so that public broadcasting or movies can be watched there.

Note that in Embodiment 5, an appropriate combination of the structures described in Embodiments 1 to 4 can be used.

Example 1

Synthesis Example 1

In Example 1, a synthesis example of the fluorene derivative which is represented as General Formula (G1) in Embodiment 1 and an embodiment of the present invention is described. Specifically, a synthesis method of 4-phenyl-4'-(9-phenylfluoren-9-yl)triphenylamine (abbreviation: BPAFLP), which is represented by Structural Formula (101) in Embodiment 1, is described. A structure of BPAFLP is shown below.

[Chemical Formula 30]

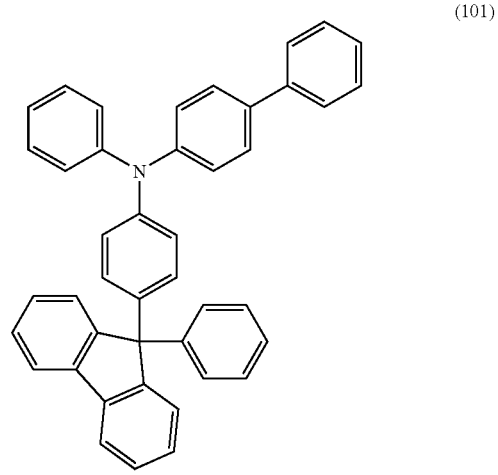 [SMILES: c1ccc(-c2ccc(N(c3ccccc3)c3ccc(C4(c5ccccc5)c5ccccc5-c5ccccc54)cc3)cc2)cc1]

(101)

Step 1: synthesis method of
9-(4-bromophenyl)-9-phenylfluorene

In a 100-mL three-neck flask, 1.2 g (50 mmol) of magnesium was heated and stirred under reduced pressure for 30 minutes to be activated. After the flask was cooled to room temperature and was made to have a nitrogen atmosphere, several drops of dibromoethane were added, so that foam formation and heat generation were confirmed. After 12 g (50 mmol) of 2-bromobiphenyl dissolved in 10 mL of diethyl ether was slowly dropped into this mixture, the mixture was stirred and heated under reflux for 2.5 hours and made into a Grignard reagent.

In a 500-mL three-neck flask, 10 g (40 mmol) of 4-bromobenzophenone and 100 mL of diethyl ether were put. After the Grignard reagent which was synthesized in advance was slowly dropped into this mixture, the mixture was heated and stirred under reflux for 9 hours After the reaction, this mixture was filtrated to obtain a residue. The obtained residue was dissolved in 150 mL of ethyl acetate, a 1N-hydrochloric acid solution was added thereto until the mixed solution became acid, and the mixture was stirred for 2 hours. An organic layer of this solution was washed with water. Then, magnesium sulfate was added to remove moisture. This suspension was filtrated and the obtained filtrate was concentrated to obtain a candy-like substance.

Then, in a 500-mL recovery flask, this candy-like substance, 50 mL of glacial acetic acid, and 1.0 mL of hydrochloric acid were put, and the mixture was heated and stirred under a nitrogen atmosphere at 130° C. for 1.5 hours to be reacted.

After the reaction, this reaction mixture solution was filtrated to obtain a residue. The obtained residue was washed with water, a sodium hydroxide aqueous solution, water, and methanol in this order, and then dried, so that 11 g of an objective white powder was obtained at a yield of 69%. A reaction scheme of the above synthesis method is shown in the following (J-1).

[Chemical Formula 31]

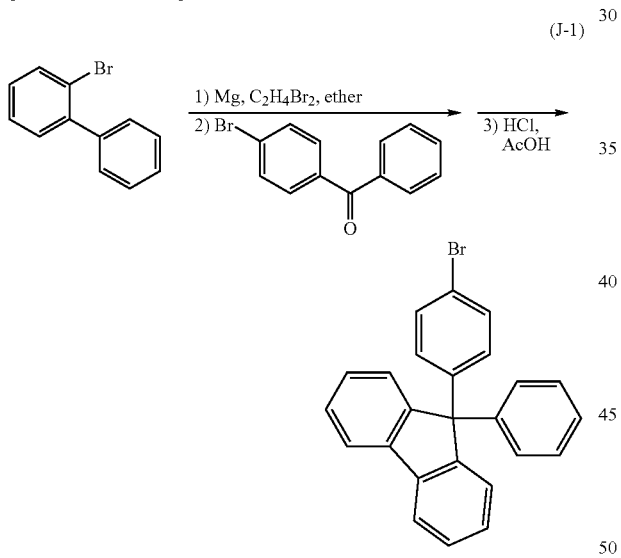

Step 2: synthesis method of 4-phenyl-4'-(9-phenylfluoren-9-yl)triphenylamine (abbreviation: BPAFLP)

3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0) were added to a 100-mL three-neck flask, and the atmosphere in the flask was substituted by nitrogen. Then, 20 mL of dehydrated xylene was added to this mixture. After the mixture was deaerated while being stirred under reduced pressure, 0.2 mL (0.1 mmol) of tri(tert-butyl)phosphine (10 wt % hexane solution) was added thereto. This mixture was heated and stirred under a nitrogen atmosphere at 110° C. for 2 hours to be reacted.

After the reaction, 200 ml of toluene was added to the reaction mixture solution, and the resulting suspension was filtrated through Florisil (produced by Wako Pure Chemical Industries, Ltd., Catalog No. 540-00135) and Celite (Wako Pure Chemical Industries, Ltd., Catalog No. 531-16855). The obtained filtrate was concentrated and purified by silica gel column chromatography (developing solvent, toluene: hexane=1:4). The obtained fraction was concentrated, and acetone and methanol were added thereto. The mixture was irradiated with ultrasonic wave and then recrystallized to obtain 4.1 g of an objective white powder at a yield of 92%. A reaction scheme of the above synthesis method is shown in the following (J-2).

[Chemical Formula 32]

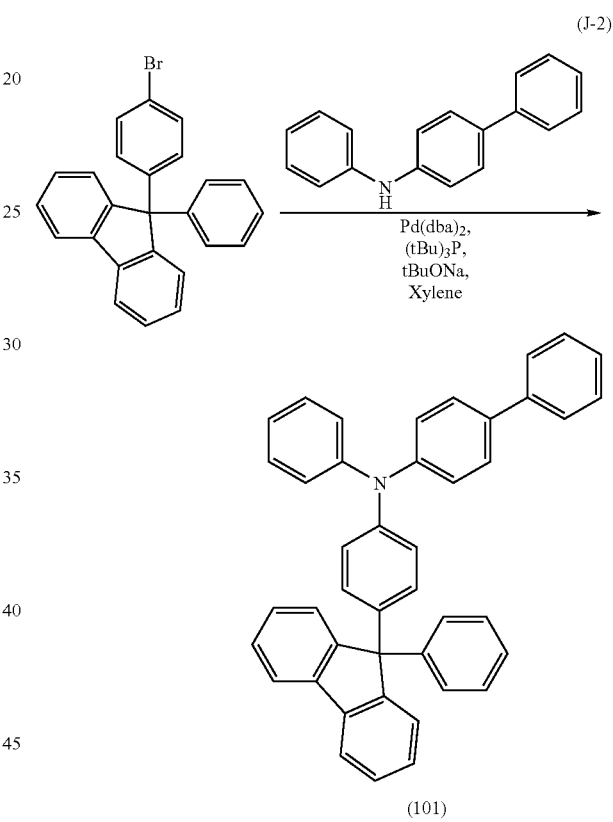

An Rf value of the object by a silica gel thin layer chromatography (TLC) (developing solvent, ethyl acetate:hexane=1:10) was 0.41, that of 9-(4-bromophenyl)-9-phenylfluorene was 0.51, and that of 4-phenyl-diphenylamine was 0.27.

Figure 10A:
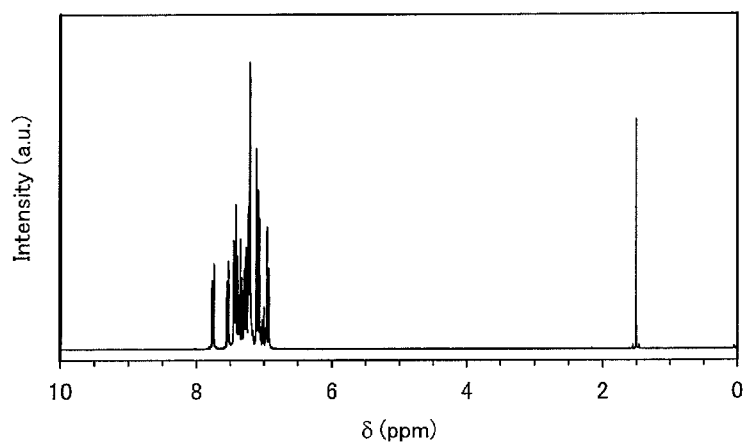
FIGS. 10A and 10B are $^1$H-NMR charts of 4-phenyl-4'-(9-phenylfluoren-9-yl)triphenylamine.
Figure 10B:
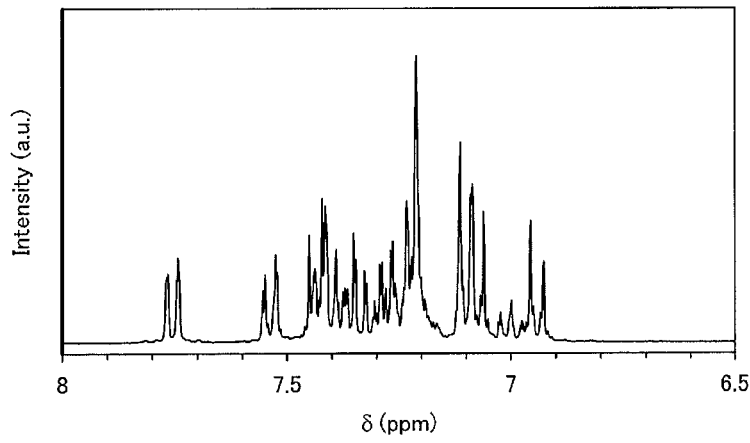

A compound that was obtained through the above Step 2 was subjected to a nuclear magnetic resonance ($^1$H-NMR) measurement. The measurement data are shown below. The $^1$H-NMR chart is shown in FIGS. 10A and 10B. The measurement results show that the fluorene derivative BPAFLP (abbreviation) of the present invention, represented by Structural Formula (101) was obtained.

$^1$H-NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), and 7.75 (d, J=6.9, 2H).

A variety of physical properties of BPAFLP (abbreviation) of the obtained object were measured as described below.

Figure 11:
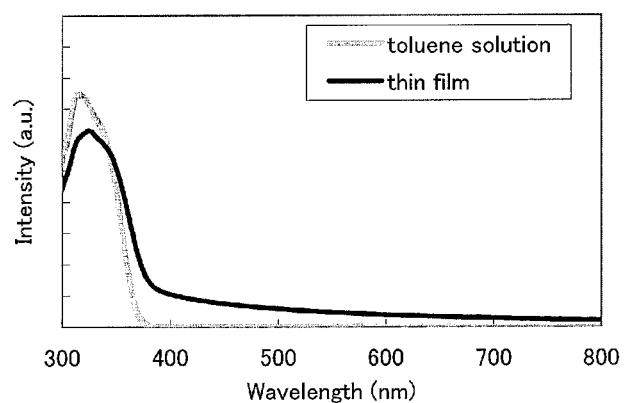
FIG. 11 is a graph showing absorption spectra of 4-phenyl-4'-(9-phenylfluoren-9-yl)triphenylamine.

The absorption spectrum (measurement range: 200 nm to 800 nm) was measured using an ultraviolet-visible spectrophotometer (V-550, manufactured by JASCO Corporation). FIG. 11 shows absorption spectra of a toluene solution and a thin film. The horizontal axis indicates the wavelength (nm) and the vertical axis indicates the absorption intensity (arbitrary unit). The toluene solution put into a quartz cell was measured, and the spectrum in which the absorption spectra of the quartz and toluene were subtracted from the absorption spectrum of the sample is shown. As the thin film, a sample evaporated on a quartz substrate was measured, and the spectrum in which the absorption spectrum of the quartz was subtracted from the absorption spectrum of the sample is shown. From these spectra, in the case of the toluene solution, an absorption peak on a long wavelength side was observed at around 314 nm, and in the case of the thin film, an absorption peak on a long wavelength side was observed at around 324 nm.

Figure 12:
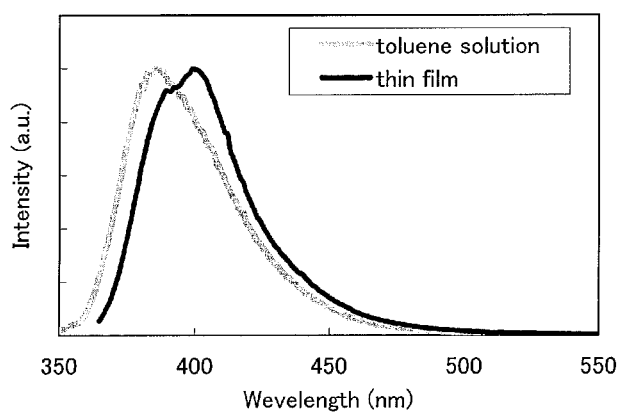
FIG. 12 is a graph showing emission spectra of 4-phenyl-4'-(9-phenylfluoren-9-yl)triphenylamine.

The emission spectrum was measured using a fluorescence spectrophotometer (FS920, manufactured by Hamamatsu Photonics Corporation). FIG. 12 shows emission spectra of a toluene solution and a thin film. The horizontal axis indicates the wavelength (nm) and the vertical axis indicates the absorption intensity (arbitrary unit). The toluene put into a quartz cell was measured, and as the thin film, a sample evaporated on a quartz substrate was measured. From these spectra, in the case of the toluene solution, the maximum emission wavelength was observed at 386 nm (excitation wavelength: 330 nm), and in the case of the thin film, the maximum emission wavelength was observed at 400 nm (excitation wavelength: 349 nm).

The result of measuring the thin film using a photoelectron spectrometer (AC-2, manufactured by Riken Keiki Co., Ltd.) under the atmosphere indicated that the HOMO level of the thin film was −5.63 eV. The Tauc plot of the absorption spectrum of the thin film revealed that the absorption edge was 3.34 eV. Thus, the energy gap in the solid state was estimated to be 3.34 eV, which means that the LUMO level of the thin film was −2.29 eV. This indicates that BPAFLP (abbreviation) has a relatively deep HOMO level and a wide band gap (Bg).

The characteristics of oxidation-reduction reaction of BPAFLP (abbreviation) were examined by a cyclic voltammetry (CV) measurement. Note that an electrochemical analyzer (ALS model 600A or 600C, manufactured by BAS Inc.) was used for the measurement.

Note that for the measurement of the oxidation characteristic, the potential of the working electrode with respect to the reference electrode was scanned from −0.10 V to 1.50 V and then from 1.50 V to −0.10 V. As a result, the HOMO level was found to be −5.51 [eV]. In addition, the oxidation peak took a similar value even after the 100 cycles. Accordingly, it was found that repetition of the oxidation reduction between an oxidation state and a neutral state had favorable characteristics.

Note that a measurement method is described below.
(Calculation of the Potential Energy of the Reference Electrode with Respect to the Vacuum Level)

First, the potential energy (eV) of the reference electrode (an Ag/Ag$^+$ electrode) used in Example 1 with respect to the vacuum level was calculated. In other words, the Fermi level of the Ag/Ag$^+$ electrode was calculated. It is known that the oxidation-reduction potential of ferrocene in methanol is +0.610 [V vs. SHE] with respect to the normal hydrogen electrode (Reference: Christian R. Goldsmith et al., J. Am. Chem. Soc., Vol. 124, No. 1, 83-96, 2002). On the other hand, using the reference electrode used in Example 1, the oxidation-reduction potential of ferrocene in methanol was calculated to be +0.11 [V vs. Ag/Ag$^+$]. Therefore, it was found that the potential energy of the reference electrode used in Example 1 was lower than that of the standard hydrogen electrode by 0.50 [eV].

Note that it is known that the potential energy of the normal hydrogen electrode from the vacuum level is −4.44 eV (Reference: Toshihiro Ohnishi and Tamami Koyama, High molecular EL material, Kyoritsu shuppan, pp. 64-67). Accordingly, the potential energy of the reference electrode used in Example 1 with respect to the vacuum level could be calculated to be −4.44−0.50=−4.94 [eV].
(CV Measurement Conditions of the Object)

As for a solution used for the CV measurement, dehydrated dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. It is to be noted that the measurement was conducted at room temperature (20° C. to 25° C.). In addition, the scan rate at the CV measurement was set to 0.1 V/sec in all the measurement.

Figure 13:
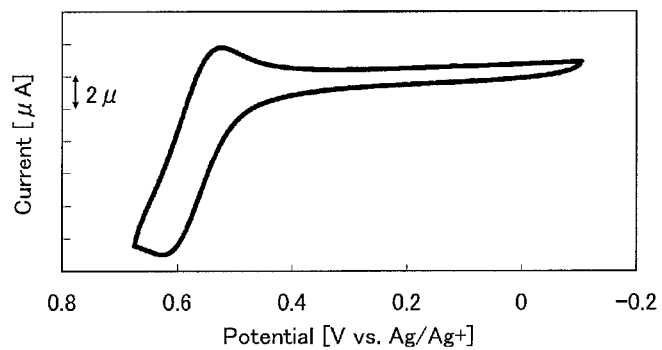
FIG. 13 is a graph showing a result of CV measurement of 4-phenyl-4'-(9-phenylfluoren-9-yl)triphenylamine.

Next, the HOMO level was calculated from the CV measurement. FIG. 13 shows the CV measurement results of the oxidation reaction characteristics. As shown in FIG. 13, an oxidation peak potential (from the neutral state to the oxidation state) $E_{pa}$ was 0.62 V. In addition, a reduction peak potential (from the oxidation side to the neutral state) $E_{pc}$ was 0.52 V. Therefore, a half-wave potential (an intermediate potential between $E_{pa}$ and $E_{pc}$, $(E_{pa+Epc})/2$[V] can be calculated to be 0.57 V. This shows that oxidization occurs by an electrical energy of +0.57[V vs. Ag/Ag$^+$. Here, as described above, the potential energy of the reference electrode, which was used in Example 1, with respect to the vacuum level is −4.94 [eV]; therefore, it was understood that the HOMO level of BPAFLP (abbreviation) was calculated as follows: −4.94−0.57=−5.51 [eV].

The glass transition temperature was measured with a differential scanning calorimetry (Pyris 1 DSC, manufactured by Perkin Elmer Co., Ltd.). According to the measurement results, it was found that the glass transition temperature was 107° C. In this manner, BPAFLP (abbreviation) had a high glass transition temperature and favorable heat resistance. In addition, the crystallization peak did not exist; thus, it was found that BPAFLP (abbreviation) was a substance which is hard to be crystallized.

Example 2

Synthesis Example 2

In Example 2, a synthesis example of the fluorene derivative which is represented as General Formula (G1) in Embodiment 1 and an embodiment of the present invention is described. Specifically, a synthesis method of 4-phenyl-4'-[4-(9-phenylfluoren-9-yl)phenyl]triphenylamine (abbreviation: BPAFLBi), which is represented in Structural Formula (151) in Embodiment 1, is described. A structure of BPAFLBi is shown below.

[Chemical Formula 33]

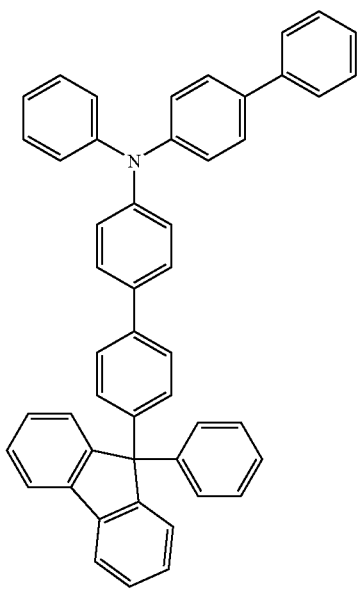

(151)

washed with water. After the washing, magnesium sulfate was added thereto to remove moisture. This suspension was filtrated, and the obtained filtrate was concentrated and purified by silica gel column chromatography (developing solvent, hexane). The obtained fraction was concentrated, methanol was added thereto, ultrasonic waves were applied thereto, and then recrystallization thereof was performed to obtain an objective white powder.

Then, in a 200-mL recovery flask, this white powder, 50 mL of glacial acetic acid, and 1.0 mL of hydrochloric acid were put, and the mixture was heated and stirred under a nitrogen atmosphere at 130° C. for 2.5 hours to be reacted.

After the reaction, this reaction mixture solution was filtrated to obtain filtrate. The obtained filtrate was dissolved in 100 mL of toluene and washed with water, a sodium hydroxide aqueous solution, water in this order, and magnesium sulfate was added thereto to remove moisture. This suspension was filtrated, the obtained filtrate was concentrated, and acetone and methanol were added thereto. The mixture was irradiated with ultrasonic wave and then recrystallized to obtain 6.3 g of an objective white powder at a yield of 67%. A reaction scheme of the above synthesis method is shown in the following (J-3).

[Chemical Formula 34]

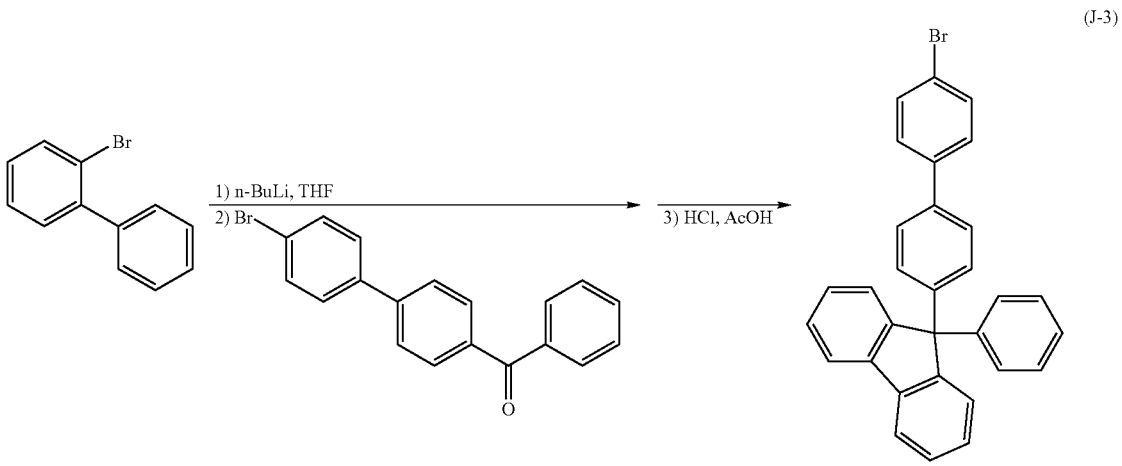

(J-3)

Step 1: synthesis method of
9-(4'-bromo-4-biphenyl)-9-phenylfluorene

In a 500-mL three-neck flask, 5.1 g (22 mmol) of 2-bromobiphenyl was put, and the atmosphere in the flask was substituted by nitrogen. Then, 200 mL of dehydrated tetrahydrofuran (abbreviation: THF) was added thereto and the mixture solution was cooled to −78° C. 14 mL (22 mmol) of an n-butyllithium hexane solution was dropped into this mixture solution, and the mixture was stirred for 2.5 hours. After that, 6.7 g (20 mmol) of 4-benzoyl-4'-bromobiphenyl was added to this mixture, and the mixture was stirred at −78° C. for 2 hours and at room temperature for 85 hours.

After the reaction, 1N-diluted hydrochloric acid was added to this reaction solution until the mixed solution became acid, and the mixture was stirred for 4 hours. This solution was Step 2: synthesis method of 4-phenyl-4'-[4-(9-phenylfluoren-9-yl)phenyl]triphenylamine (abbreviation: BPAFLBi)

3.8 g (8.0 mmol) of 9-(4'-bromo-4-biphenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0) were added to a 100-mL three-neck flask, and the atmosphere in the flask was substituted by nitrogen. Then, 20 mL of dehydrated xylene was added to this mixture. After the mixture was deaerated while being stirred under reduced pressure, 0.2 mL (0.1 mmol) of tri(tert-butyl)phosphine (10 wt % hexane solution) was added thereto. This mixture was heated and stirred under a nitrogen atmosphere at 110° C. for 2 hours to be reacted.

After the reaction, 200 mL of toluene was added to the reaction mixture solution, and the resulting suspension was filtrated through Florisil and Celite. The obtained filtrate was concentrated and purified by silica gel column chromatography (developing solvent, toluene: hexane=1:4). The obtained fraction was concentrated, and acetone and methanol were added thereto. The mixture was irradiated with ultrasonic wave and then recrystallized to obtain 4.4 g of an objective white powder at a yield of 86%. A reaction scheme of the above synthesis method is shown in the following (J-4).

[Chemical Formula 35]

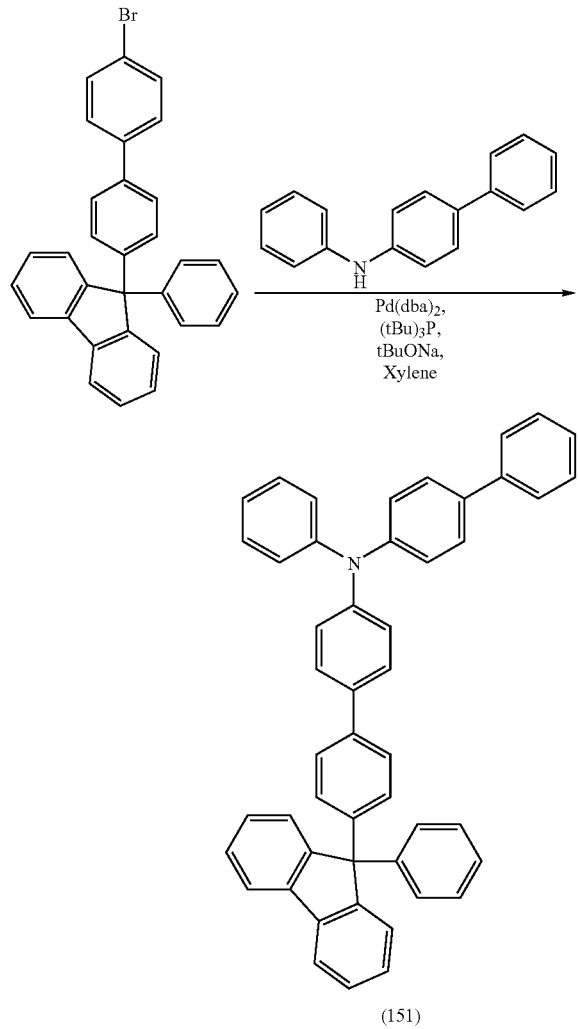

(151)

An Rf value of the object by a silica gel thin layer chromatography (TLC) (developing solvent, ethyl acetate:hexane=1: 10) was 0.51, that of 9-(4'-bromo-4-biphenyl)-9-phenylfluorene was 0.56, and that of 4-phenyl-diphenylamine was 0.28.

Figure 14A:
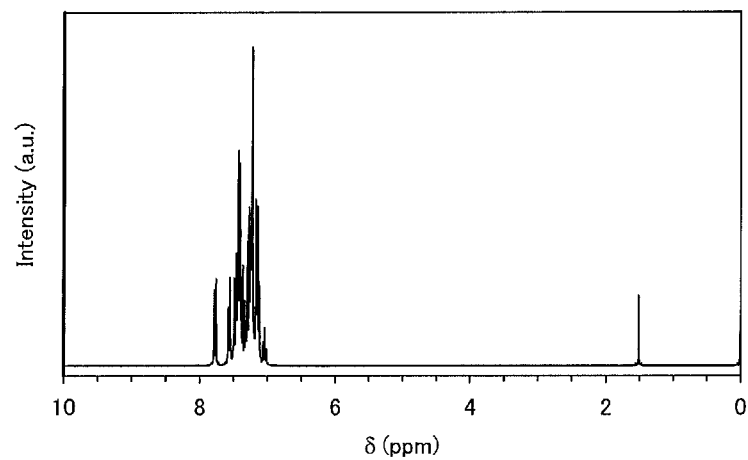
FIGS. 14A and 14B are $^1$H-NMR charts of 4-phenyl-4'-[4-(9-phenylfluoren-9-yl)phenyl]triphenylamine.
Figure 14B:
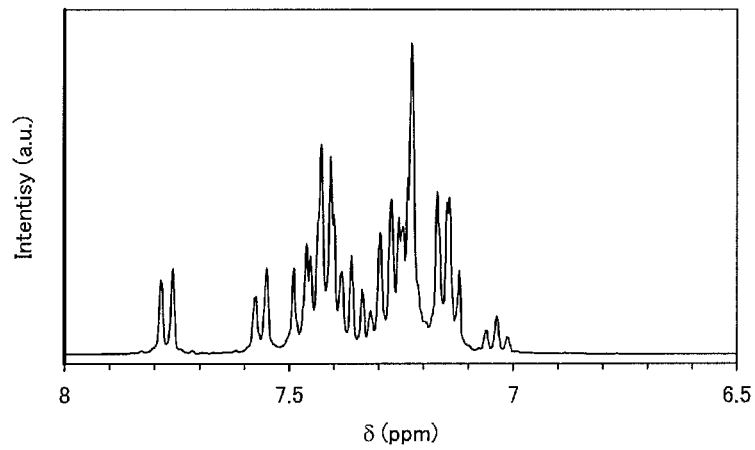

A compound that was obtained through Step 2 was subjected to a nuclear magnetic resonance ($^1$H-NMR) measurement. The measurement data are shown below. The $^1$H NMR chart is shown in FIGS. 14A and 14B. The measurement results show that the fluorene derivative BPAFLBi (abbreviation) of the present invention, represented by Structural Formula (151) was obtained.

$^1$H-NMR (CDCl$_3$, 300 MHz): δ (ppm)=7.04 (t, J=6.6, 1H), 7.12-7.49 (m, 30H), 7.55-7.58 (m, 2H), and 7.77 (d, J=7.8, 2H).

A variety of physical properties of BPAFLBi (abbreviation) of the obtained object were measured as described below.

Figure 15:
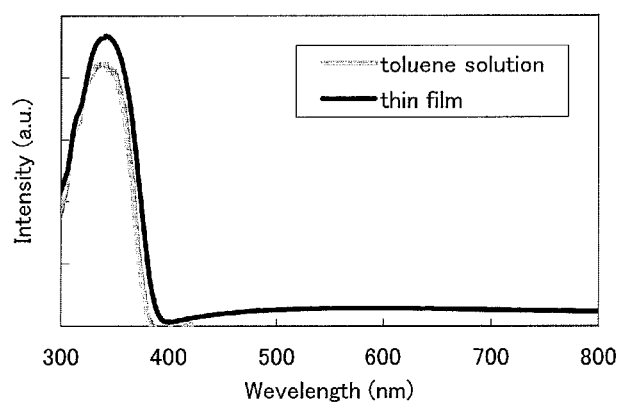
FIG. 15 is a graph showing absorption spectra of 4-phenyl-4'-[4-(9-phenylfluoren-9-yl)phenyl]triphenylamine.

The absorption spectrum (measurement range: 200 nm to 800 nm) was measured using an ultraviolet-visible spectrophotometer (V-550, manufactured by JASCO Corporation). FIG. 15 shows absorption spectra of a toluene solution and a thin film. The horizontal axis indicates the wavelength (nm) and the vertical axis indicates the absorption intensity (arbitrary unit). The toluene solution put into a quartz cell was measured, and the spectrum in which the absorption spectra of the quartz and toluene were subtracted from the absorption spectrum of the sample is shown. As the thin film, a sample evaporated on a quartz substrate was measured, and the spectrum in which the absorption spectrum of the quartz was subtracted from the absorption spectrum of the sample is shown. From these spectra, in the case of the toluene solution, an absorption peak on a long wavelength side was observed at around 340 nm, and in the case of the thin film, an absorption peak on a long wavelength side was observed at around 341 nm.

Figure 16:
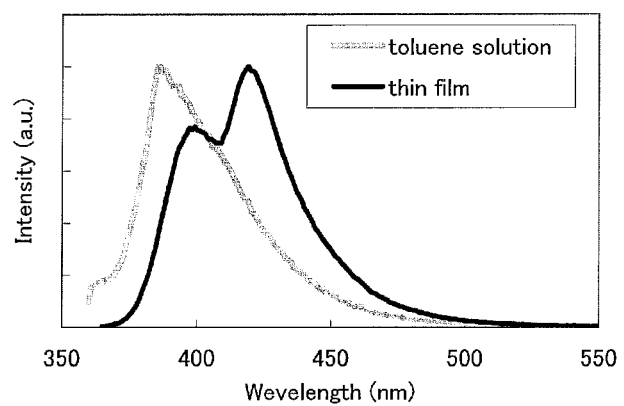
FIG. 16 is a graph showing emission spectra of 4-phenyl-4'-[4-(9-phenylfluoren-9-yl)phenyl]triphenylamine.

The emission spectrum was measured using a fluorescence spectrophotometer (FS920, manufactured by Hamamatsu Photonics Corporation). FIG. 16 shows emission spectra of a toluene solution and a thin film. The horizontal axis indicates the wavelength (nm) and the vertical axis indicates the emission intensity (arbitrary unit). The toluene put into a quartz cell was measured, and as the thin film, a sample evaporated on a quartz substrate was measured. From these spectra, in the case of the toluene solution, the maximum emission wavelength was observed at 386 nm (excitation wavelength: 345 nm), and in the case of the thin film, the maximum emission wavelengths were observed at 399, 419 nm (excitation wavelength: 348 nm).

The result of measuring the thin film using a photoelectron spectrometer (AC-2, manufactured by Riken Keiki Co., Ltd.) under the atmosphere indicated that the HOMO level of the thin film was −5.64 eV. The Tauc plot of the absorption spectrum of the thin film revealed that the absorption edge was 3.28 eV. Thus, the energy gap in the solid state was estimated to be 3.28 eV, which means that the LUMO level of the thin film is −2.36 eV. This indicates that BPAFLBi (abbreviation) has a relatively deep HOMO level and a wide band gap (Bg).

The characteristics of oxidation-reduction reaction of BPAFLBi (abbreviation) were examined by a cyclic voltammetry (CV) measurement. Note that an electrochemical analyzer (ALS model 600A or 600C, manufactured by BAS Inc.) was used for the measurement. Since the measurement method is similar to that of Example 1, the description is omitted.

Note that for the measurement of the oxidation characteristic, the potential of the working electrode with respect to the reference electrode was scanned from −0.10 V to 1.50 V and then from 1.50 V to −0.10 V. As a result, the HOMO level was found to be −5.49 [eV]. In addition, the oxidation peak took a similar value even after the 100 cycles. Accordingly, it was found that repetition of the oxidation reduction between an oxidation state and a neutral state had favorable characteristics.

Figure 17:
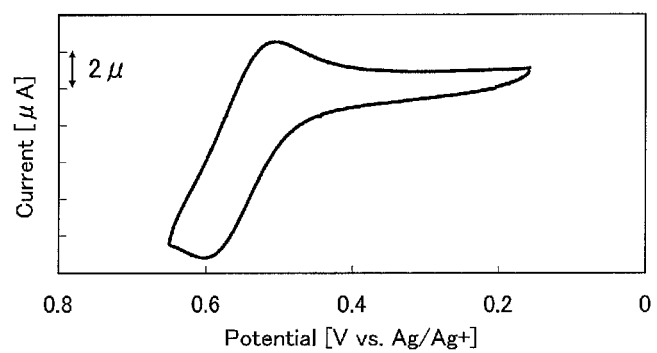
FIG. 17 is a graph showing a result of CV measurement of 4-phenyl-4'-[4-(9-phenylfluoren-9-yl)phenyl]triphenylamine.

FIG. 17 shows CV measurement results of the oxidation reaction characteristics of BPAFLBi (abbreviation).

The glass transition temperature was measured with a differential scanning calorimetry (Pyris 1 DSC, manufactured by Perkin Elmer Co., Ltd.). According to the measurement results, it was found that the glass transition temperature was 126° C. In this manner, BPAFLBi (abbreviation) had a high glass transition temperature and favorable heat resistance. In addition, the crystallization peak did not exist; thus, it was found that BPAFLBi (abbreviation) was a substance which was hard to be crystallized.

Example 3

In Example 3, a method for manufacturing a light-emitting element formed using 4-phenyl-4'-(9-phenylfluoren-9-yl)triphenylamine (abbreviation: BPAFLP), which is the fluorene derivative synthesized in Example 1 and measurement results of element characteristics are described.

Figure 18:
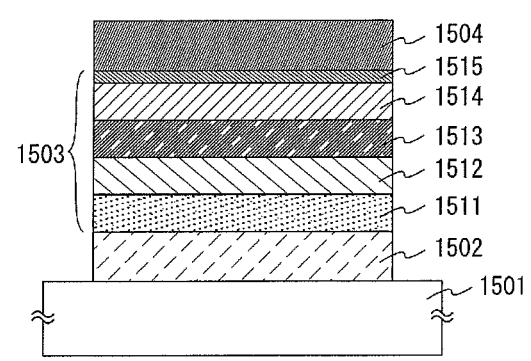
FIG. 18 is a view illustrating a light-emitting element of Examples.

The light-emitting element of Example 3 has an element structure illustrated in FIG. 18. Light-Emitting Element 2 is formed using the fluorene derivative (abbreviation: BPAFLP) of the present invention for a hole-transport layer 1512. In addition, Light-Emitting Element 1 which is a comparative light-emitting element is formed using 4,4'-bis[N-(1-naphthyl)-N-phenylamino]biphenyl (abbreviation: NPB) for the hole-transport layer 1512. In order to make the same comparative conditions between Light-Emitting Element 1 and Light-Emitting Element 2, Comparative Light-Emitting Element 1 was formed over the same substrate as that of Light-Emitting Element 2, and Light-Emitting Element 1 was compared to Light-Emitting Element 2. Structural Formulae of an organic compound used in Example 3 are shown below.

[Chemical Formula 36]

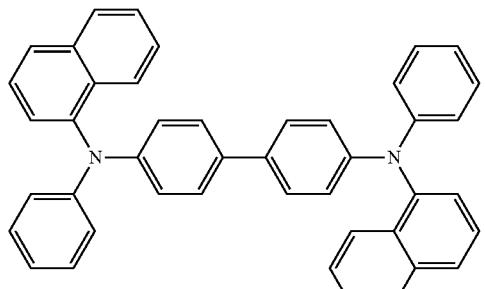

NPB

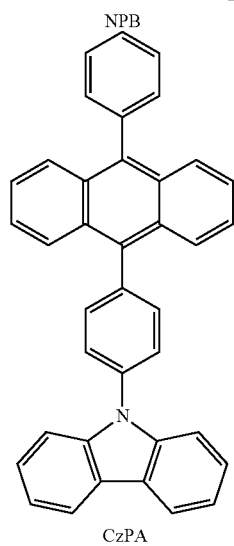

CzPA

-continued

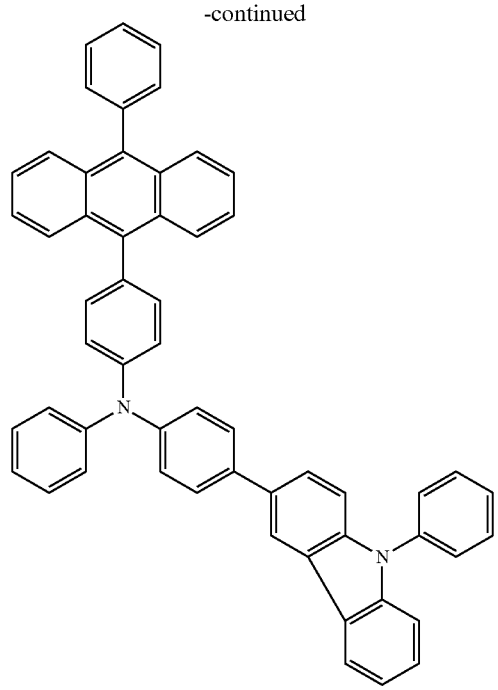

PCBAPA

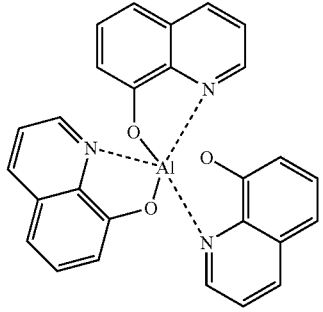

Alq

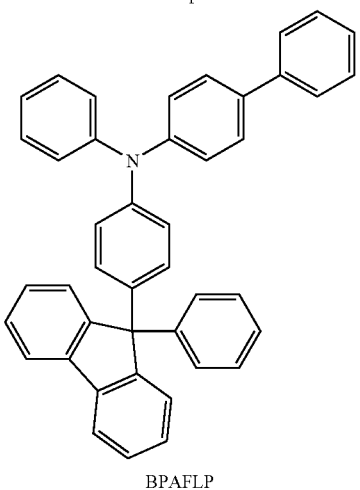

BPAFLP

First, indium oxide-tin oxide containing silicon oxide was deposited on a substrate 1501 which was a glass substrate by a sputtering method to form a first electrode 1502. Note that the thickness of the first electrode 1502 was 110 nm and the electrode area was 2 mm×2 mm.

Next, an EL layer 1503 including a stack of a plurality of layers is formed over the first electrode 1502. In Example 5, the EL layer 1503 has a structure in which a first layer 1511 which is a hole-injection layer, a second layer 1512 which is a hole-transport layer, a third layer 1513 which is a light-emitting layer, a fourth layer 1514 which is an electron-transport layer, and a fifth layer 1515 which is an electron-injection layer are sequentially stacked.

The substrate provided with the first electrode 1502 was fixed to a substrate holder which was provided in a vacuum evaporation apparatus so that a surface provided with the first electrode 1502 faced downward. The pressure in the vacuum evaporation apparatus was reduced to approximately $10^{-4}$ Pa. Then, over the first electrode 1502, 4,4'-bis[N-(1-naphthyl)-N-phenylamino]biphenyl (NPB) and molybdenum(VI) oxide were co-evaporated to form the first layer 1511 which is a hole-injection layer. The thickness was 50 nm, and the evaporation rate was controlled so that the weight ratio of NPB to molybdenum (VI) oxide could be 4:1=(NPB: molybdenum oxide). Note that the co-evaporation method is an evaporation method in which evaporation of a plurality of materials is performed from a plurality of evaporation sources at the same time in one treatment chamber.

Next, a hole-transport material was deposited on the first layer 1511 to a thickness of 10 nm by an evaporation method using resistance heating, and the second layer 1512 which was a hole-transport layer was formed. Note that Comparative Light-Emitting Element 1 was formed using 4,4'-bis[N-(1-naphthyl)-N-phenylamino]biphenyl (abbreviation: NPB) and Light-Emitting Element 2 was formed using 4-phenyl-4'-(9-phenylfluoren-9-yl)triphenylamine (abbreviation: BPAFLP).

Next, the third layer 1513 which was a light-emitting layer was formed on the second layer 1512 by an evaporation method using resistance heating. The third layer 1513 was formed by co-evaporating 9-[4-(10-phenyl-9-anthryl)phenyl]-9H-carbazole (abbreviation: CzPA) and 4-(10-phenyl-9-anthryl)-4'-(9-phenyl-9H-carbazol-3-yl)triphenylamine (abbreviation: PCBAPA) to a thickness of 30 nm. Here, the evaporation rate was controlled so that the weight ratio of CzPA to PCBAPA could be 1:0.10=(CzPA: PCBAPA).

Furthermore, on the third layer 1513, a 10-nm-thick film of tris(8-quinolinolato)aluminum(III) (abbreviation: Alq) and, thereon, a 20-nm-thick film of bathophenanthroline (abbreviation: BPhen) were formed by an evaporation method using resistance heating to form the fourth layer 1514 which was an electron-transport layer.

On the fourth layer 1514, a 1-nm-thick film of lithium fluoride (LiF) was formed as the fifth layer 1515 which was an electron-inject layer.

Lastly, a 200-nm-thick film of aluminum was formed by an evaporation method using resistance heating to form the second electrode 1504. Thus, Comparative Light-Emitting Element 1 and Light-Emitting Element 2 were formed.

Note that Comparative Light-Emitting Element 1 and Light-Emitting Element 2 were formed in the same steps, except for the second layer 1512.

Comparative Light-Emitting Element 1 and Light-Emitting Element 2 thus obtained were sealed in a glove box having a nitrogen atmosphere without being exposed to the air. Then, the operating characteristics thereof were measured. Note that the measurement was carried out at room temperature (in an atmosphere kept at 25° C.).

Figure 19:
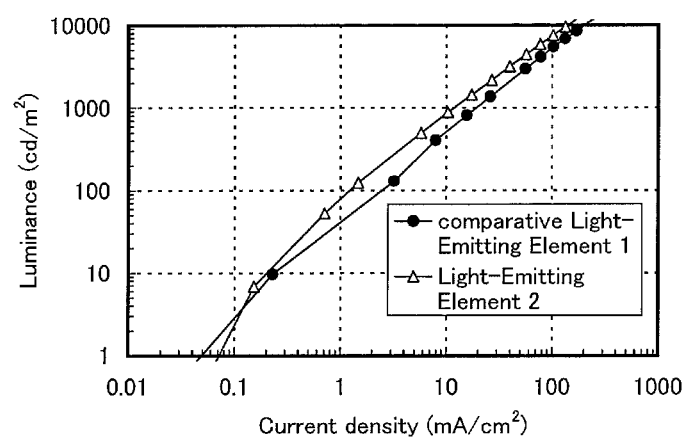
FIG. 19 is a graph showing current density vs. luminance characteristics of Comparative Light-Emitting Element 1 and Light-Emitting Element 2.
Figure 20:
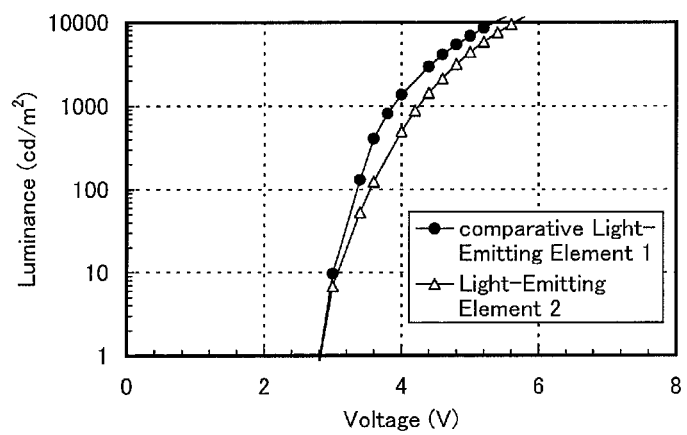
FIG. 20 is a graph showing voltage vs. luminance characteristics of Comparative Light-Emitting Element 1 and Light-Emitting Element 2.
Figure 21:
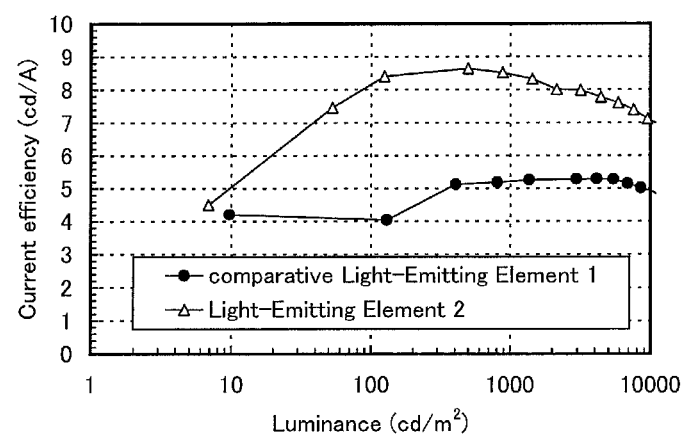
FIG. 21 is a graph showing luminance vs. current efficiency characteristics of Comparative Light-Emitting Element 1 and Light-Emitting Element 2.

FIG. 19 shows the current density vs. luminance characteristics of Comparative Light-Emitting Element 1 and Light-Emitting Element 2. FIG. 20 shows the voltage vs. luminance characteristics of Comparative Light-Emitting Element 1 and Light-Emitting Element 2. FIG. 21 shows the luminance vs. current efficiency characteristics of Comparative Light-Emitting Element 1 and Light-Emitting Element 2. In FIG. 19, the vertical axis represents luminance ($cd/m^2$) and the horizontal axis represents current density ($mA/cm^2$). In FIG. 20, the vertical axis represents luminance ($cd/m^2$) and the horizontal axis represents voltage (V). In FIG. 21, the vertical axis represents current efficiency (cd/A) and the horizontal axis represents luminance ($cd/m^2$). In addition, Table 1 shows the voltage, chromaticity, and current efficiency of each of Comparative Light-Emitting Element 1 and Light-Emitting Element 2 around 1000 $cd/m^2$.

TABLE 1

| | Voltage (V) | Chromaticity x | Chromaticity y | Current efficiency (cd/A) |
|---|---|---|---|---|
| Comparative Light-Emitting Element 1 | 3.8 | 0.16 | 0.19 | 5.2 |
| Light-Emitting Element 2 | 4.2 | 0.15 | 0.21 | 8.5 |

When the drive voltage of Light-Emitting Element 2 was 4.2 V, the luminance and the current value were 880 $cd/m^2$ and 0.41 mA, respectively. It was found that in comparison with Comparative Light-Emitting Element 1 using NPB (abbreviation) for the second layer 1512, Light-Emitting Element 2 using BPAFLP (abbreviation) for the second layer 1512 has higher current efficiency. This is because the carrier balance of Light-Emitting Element 2 is considered to be improved as compared to Light-Emitting Element 1. That is considered that the hole-injection property from the hole-transport layer to the light-emitting layer was improved because the HOMO level of BPAFLP (abbreviation) was closer to the HOMO level of CzPA (abbreviation) which is the host material of the light-emitting layer than the HOMO level of NPB. Further, it is considered that the electron blocking property from the light-emitting layer to the hole-transport layer was improved because the LUMO level of BPAFLP (abbreviation) was higher than the LUMO level of NPB. Furthermore, it is considered that excitons generated in the third layer (light-emitting layer) 1513 were not transferred to the second layer 1512 which was an adjacent layer (that is to say, not quenched) and were confined because BPAFLP (abbreviation) has a wide band gap (Bg) (in comparison with NPB).

Example 4

In Example 4, a method for manufacturing a light-emitting element formed using 4-phenyl-4'-(9-phenylfluoren-9-yl)triphenylamine (abbreviation: BPAFLP), which is the fluorene derivative synthesized in Example 1 and measurement results of element characteristics are described.

The light-emitting element of Example 4 has an element structure illustrated in FIG. 18. Light-Emitting Element 3 is formed using the above-described fluorene derivative (abbreviation: BPAFLP) of the present invention for a hole-transport layer 1512. Structural Formulae of an organic compound used in Example 4 are shown below.

[Chemical Formula 37]

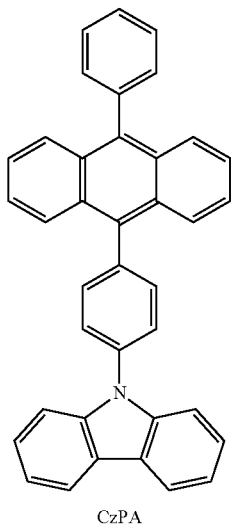

CzPA

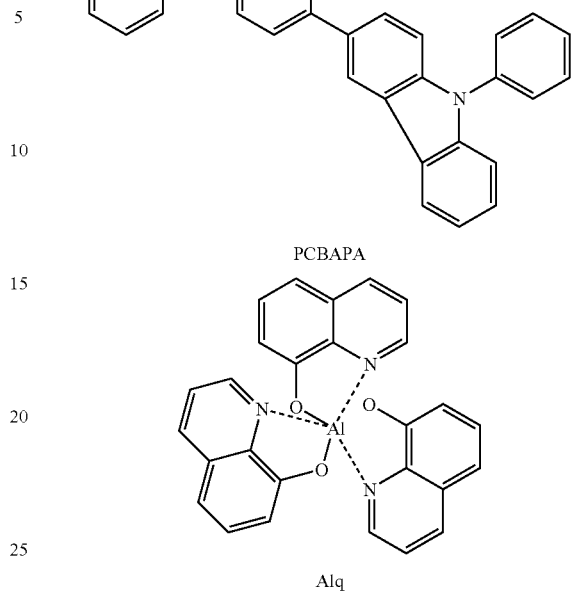

PCBAPA

Alq

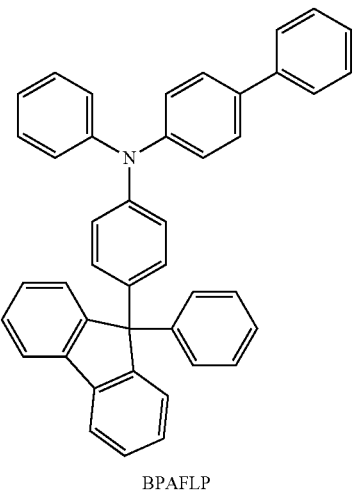

BPAFLP

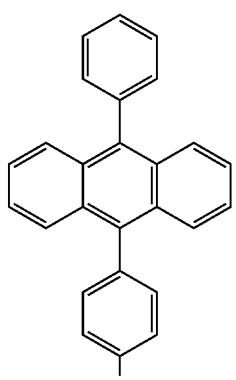

First, indium oxide-tin oxide containing silicon oxide was deposited on a substrate 1501 which was a glass substrate by a sputtering method to form a first electrode 1502. Note that the thickness of the first electrode 1502 was 110 nm and the electrode area was 2 mm×2 mm.

Next, an EL layer 1503 including a stack of a plurality of layers is formed over the first electrode 1502. In Example 4, the EL layer 1503 has a structure in which a first layer 1511 which is a hole-injection layer, a second layer 1512 which is a hole-transport layer, a third layer 1513 which is a light-emitting layer, a fourth layer 1514 which is an electron-transport layer, and a fifth layer 1515 which is an electron-injection layer are sequentially stacked.

The substrate provided with the first electrode 1502 was fixed to a substrate holder which was provided in a vacuum evaporation apparatus so that a surface provided with the first electrode 1502 faced downward. The pressure in the vacuum evaporation apparatus was reduced to approximately $10^{-4}$ Pa. Then, over the first electrode 1502, 9-[4-(10-phenyl-9-anthryl)phenyl]-9H-carbazole (abbreviation: CzPA) and molybdenum(VI) oxide were co-evaporated to form the first layer 1511 which is a hole-injection layer. The thickness was 50 nm, and the evaporation rate was controlled so that the weight ratio of CzPA to molybdenum (VI) oxide could be 4:1=(CzPA: molybdenum oxide).

Next, a hole-transport material was deposited on the first layer 1511 to a thickness of 10 nm by an evaporation method using resistance heating, and the second layer 1512 which was a hole-transport layer was formed. Note that Light-Emitting Element 3 was formed using 4-phenyl-4'-(9-phenylfluoren-9-yl)triphenylamine (abbreviation: BPAFLP).

Next, the third layer 1513 which was a light-emitting layer was formed on the second layer 1512 by an evaporation method using resistance heating. The third layer 1513 was formed by co-evaporating 9-[4-(10-phenyl-9-anthryl)phenyl]-9H-carbazole (abbreviation: CzPA) and 4-(10-phenyl-9-anthryl)-4'-(9-phenyl-9H-carbazol-3-yl)triphenylamine (abbreviation: PCBAPA) to a thickness of 30 nm. Here, the evaporation rate was controlled so that the weight ratio of CzPA to PCBAPA could be 1:0.10=(CzPA: PCBAPA).

After that, in a manner similar to Comparative Light-Emitting Element 1, the fourth layer which was an electron-transport layer, the fifth layer which was an electron-injection layer, and a second electrode were formed. Thus, Light-Emitting Element 3 was formed.

Light-Emitting Element 3 thus obtained was sealed in a glove box having a nitrogen atmosphere without being exposed to the air. Then, the operating characteristics of Light-Emitting Element 3 were measured. Note that the measurement was carried out at room temperature (in an atmosphere kept at 25° C.).

Figure 22:
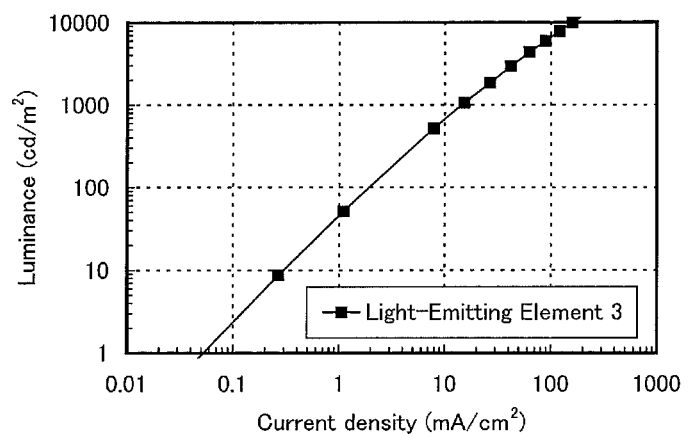
FIG. 22 is a graph showing current density vs. luminance characteristics of Light-Emitting Element 3.
Figure 23:
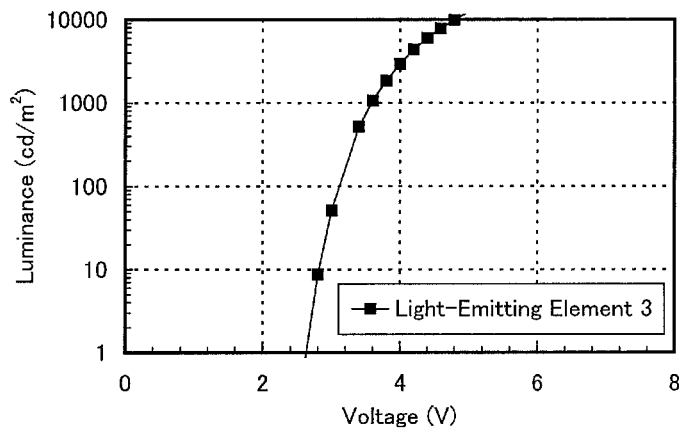
FIG. 23 is a graph showing voltage vs. luminance characteristics of Light-Emitting Element 3.
Figure 24:
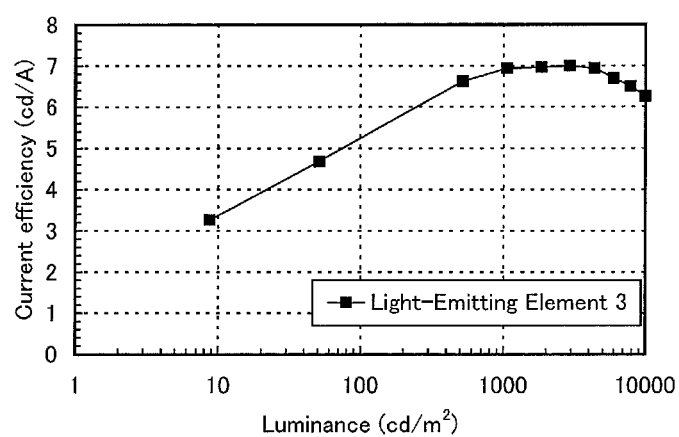
FIG. 24 is a graph showing luminance vs. current efficiency characteristics of Light-Emitting Element 3.

FIG. 22 shows the current density vs. luminance characteristics of Light-Emitting Element 3. FIG. 23 shows the voltage vs. luminance characteristics of Light-Emitting Element 3. FIG. 24 shows the luminance vs. current efficiency characteristics of Light-Emitting Element 3. In FIG. 22, the vertical axis represents luminance ($cd/m^2$) and the horizontal axis represents current density ($mA/cm^2$). In FIG. 23, the vertical axis represents luminance ($cd/m^2$) and the horizontal axis represents voltage (V). In FIG. 24, the vertical axis represents current efficiency (cd/A) and the horizontal axis represents luminance ($cd/m^2$). In addition, Table 2 shows the voltage, chromaticity, and current efficiency of Light-Emitting Element 3 at around 1000 $cd/m^2$.

TABLE 2

| | Voltage (V) | Chromaticity x | Chromaticity y | Current efficiency (cd/A) |
|---|---|---|---|---|
| Light-Emitting Element 3 | 3.6 | 0.16 | 0.22 | 6.9 |

According to Example 4, it was confirmed that the light-emitting element using the fluorene derivative (abbreviation: BPAFLP) of the present invention had the characteristics as a light-emitting element and fully functions. Further, from the results of the reliability test, it was found that a highly reliable light-emitting element was obtained in which a short circuit due to defects of the film or the like is not caused even if the light-emitting element is made to emit light continuously.

Figure 25:
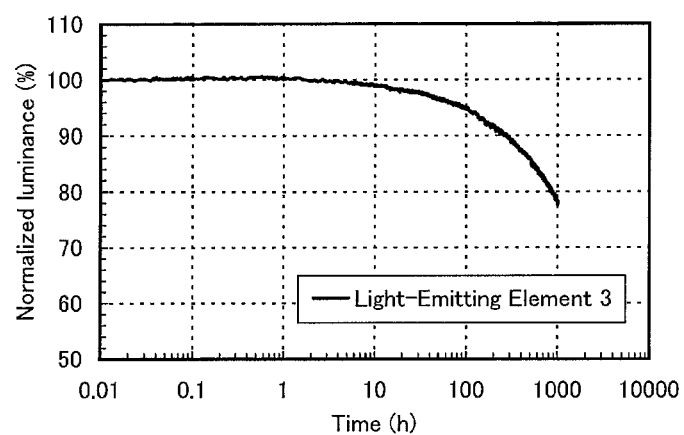
FIG. 25 is a graph showing results of a reliability test of Light-Emitting Element 3.

FIG. 25 shows results of a continuous lighting test in which Light-Emitting Element 3 was continuously lit by constant current driving with the initial luminance set at 1000 $cd/m^2$ (the vertical axis indicates the relative luminance on the assumption that 1000 $cd/m^2$ is 100%). From the results of FIG. 25, Light-Emitting Element 3 exhibits 78% of the initial luminance even after 1000 hours, which leads to that Light-Emitting Element 3 has a long lifetime. Therefore, it was found that a long-life light-emitting element can be obtained by application of BPAFLP (abbreviation) of the present invention.

Example 5

In Example 5, methods for manufacturing a light-emitting element formed using 4-phenyl-4'-[4-(9-phenylfluoren-9-yl)phenyl]triphenylamine (abbreviation: BPAFLBi) which is the fluorene derivative synthesized in Example 1 and Example 2, and a light-emitting element formed using 4-phenyl-4'-(9-phenylfluoren-9-yl)triphenylamine (abbreviation: BPAFLP) and measurement results of element characteristics are described.

The light-emitting elements of Example 5 have an element structure illustrated in FIG. 18. The light-emitting elements are formed using the above-described fluorene derivative of the present invention for a hole-injection layer and a hole-transport layer. Structural Formulae of an organic compound used in Example 5 are shown below.

[Chemical Formula 38]

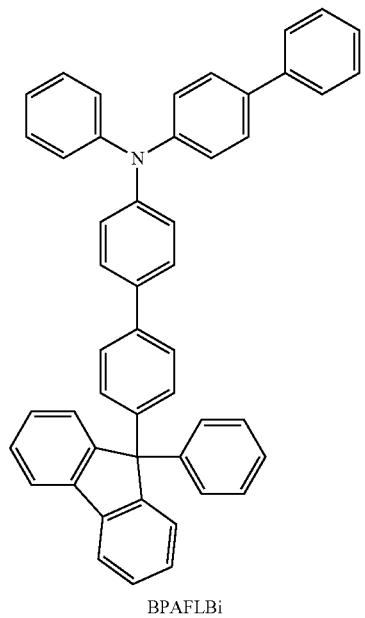

BPAFLBi

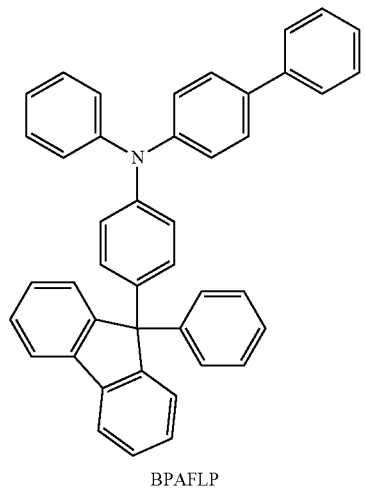

BPAFLP

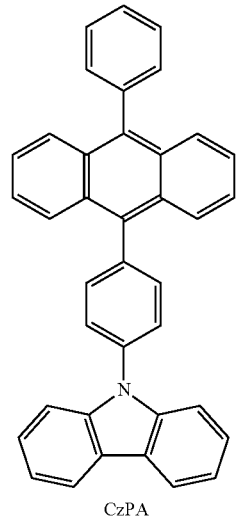

CzPA

-continued

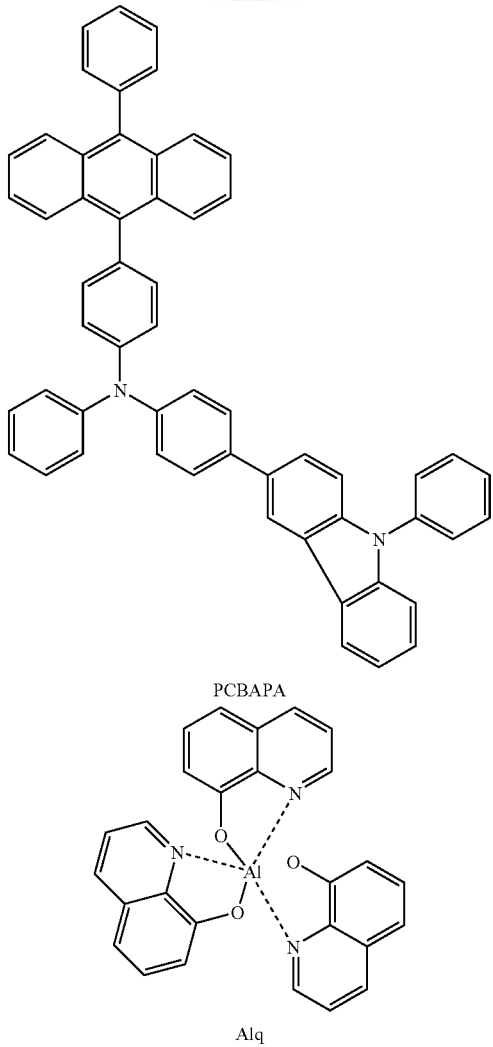

PCBAPA

Alq

First, indium oxide-tin oxide containing silicon oxide was deposited on a substrate 1501 which was a glass substrate by a sputtering method to form a first electrode 1502. Note that the thickness of the first electrode 1502 was 110 nm and the electrode area was 2 mm×2 mm.

Next, an EL layer 1503 including a stack of a plurality of layers is formed over the first electrode 1502. In Example 5, the EL layer 1503 has a structure in which a first layer 1511 which is a hole-injection layer, a second layer 1512 which is a hole-transport layer, a third layer 1513 which is a light-emitting layer, a fourth layer 1514 which is an electron-transport layer, and a fifth layer 1515 which is an electron-injection layer are sequentially stacked.

The substrate provided with the first electrode 1502 was fixed to a substrate holder which was provided in a vacuum evaporation apparatus so that a surface provided with the first electrode 1502 faced downward. The pressure in the vacuum evaporation apparatus was reduced to approximately $10^{-4}$ Pa. Then, over the first electrode 1502, the fluorene derivative of an embodiment of the present invention and molybdenum (VI) oxide were co-evaporated to form the first layer 1511 which is a hole-injection layer. The thickness was 50 nm, and the evaporation rate was controlled so that the weight ratio of the fluorene derivative to molybdenum (VI) oxide could be 4:1=(the fluorene derivative: molybdenum oxide). Note that Light-Emitting Element 4 is formed using 4-phenyl-4'-[4-(9-phenylfluoren-9-yl)phenyl]triphenylamine (abbreviation: BPAFLBi) as the fluorene derivative and Light-Emitting Element 5 is formed using 4-phenyl-4'-(9-phenylfluoren-9-yl)triphenylamine (abbreviation: BPAFLP) as the fluorene derivative.

Next, a hole-transport material was deposited on the first layer 1511 to a thickness of 10 nm by an evaporation method using resistance heating, and the second layer 1512 which was a hole-transport layer was formed. Note that Light-Emitting Element 4 was formed using BPAFLBi and Light-Emitting Element 5 was formed using BPAFLP.

Next, the third layer 1513 which was a light-emitting layer was formed on the second layer 1512 by an evaporation method using resistance heating. Note that in Example 5, the light-emitting layer has two layers (a first light-emitting layer and a second light-emitting layer). The first light-emitting layer was formed over the second layer 1512 by co-evaporating 9-[4-(10-phenyl-9-anthryl)phenyl]-9H-carbazole (abbreviation: CzPA) and 4-(10-phenyl-9-anthryl)-4'-(9-phenyl-9H-carbazol-3-yl)triphenylamine (abbreviation: PCBAPA) to a thickness of 15 nm. Here, the evaporation rate was controlled so that the weight ratio of CzPA to PCBAPA could be 1:0.10=(CzPA: PCBAPA).

Next, the second light-emitting layer was formed on the first light-emitting layer by an evaporation method using resistance heating. The second layer was formed over the first light-emitting layer by co-evaporating 9-[4-(10-phenyl-9-anthryl)phenyl]-9H-carbazole (abbreviation: CzPA) and 4-(10-phenyl-9-anthryl)-4'-(9-phenyl-9H-carbazol-3-yl)triphenylamine (abbreviation: PCBAPA) to a thickness of 15 nm. Here, the evaporation rate was controlled so that the weight ratio of CzPA to PCBAPA could be 1:0.05=(CzPA: PCBAPA).

After that, in a manner similar to Comparative Light-Emitting Element 1, the fourth layer which was an electron-transport layer, the fifth layer which was an electron-injection layer, and a second electrode were formed. Thus, Light-Emitting Element 4 and Light-Emitting Element 5 were formed.

Note that Light-Emitting Element 4 and Light-Emitting Element 5 were formed in the same steps, except for the first layer 1511 and the second layer 1512.

Light-Emitting Element 4 and Light-Emitting Element 5 thus obtained were sealed in a glove box having a nitrogen atmosphere without being exposed to the air. Then, the operating characteristics thereof were measured. Note that the measurement was carried out at room temperature (in an atmosphere kept at 25° C.).

Figure 26:
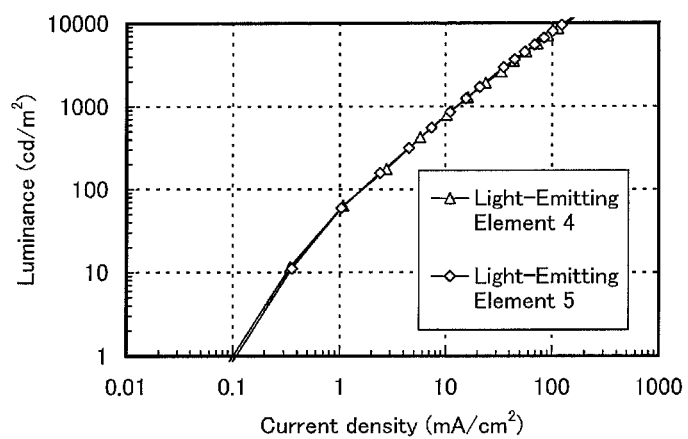
FIG. 26 is a graph showing current density vs. luminance characteristics of Light-Emitting Element 4 and Light-Emitting Element 5.
Figure 27:
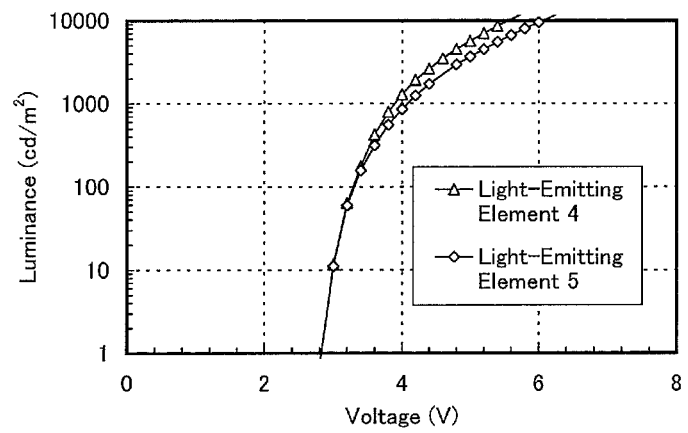
FIG. 27 is a graph showing voltage vs. luminance characteristics of Light-Emitting Element 4 and Light-Emitting Element 5.
Figure 28:
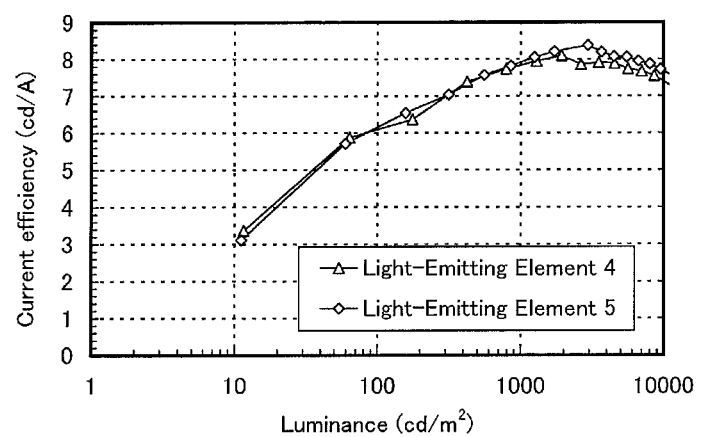
FIG. 28 is a graph showing luminance vs. current efficiency characteristics of Light-Emitting Element 4 and Light-Emitting Element 5.

FIG. 26 shows the current density vs. luminance characteristics of Light-Emitting Element 4 and Light-Emitting Element 5. FIG. 27 shows the voltage vs. luminance characteristics of Light-Emitting Element 4 and Light-Emitting Element 5. FIG. 28 shows the luminance vs. current efficiency characteristics of Light-Emitting Element 4 and Light-Emitting Element 5. In FIG. 26, the vertical axis represents luminance (cd/m$^2$) and the horizontal axis represents current density (mA/cm$^2$). In FIG. 27, the vertical axis represents luminance (cd/m$^2$) and the horizontal axis represents voltage (V). In FIG. 28, the vertical axis represents current efficiency (cd/A) and the horizontal axis represents luminance (cd/m$^2$). In addition, Table 3 shows the voltage, chromaticity, current efficiency, and external quantum efficiency of Light-Emitting Element 4 and Light-Emitting Element 5 at around 1000 cd/m$^2$.

TABLE 3

|  | Voltage (V) | Chromaticity x | Chromaticity y | Current efficiency (cd/A) | Quantum efficiency (%) |
|---|---|---|---|---|---|
| Light-Emitting Element 4 | 3.8 | 0.16 | 0.22 | 7.7 | 5.0 |
| Light-Emitting Element 5 | 4.0 | 0.16 | 0.21 | 7.8 | 5.2 |

According to Example 5, it was confirmed that the light-emitting elements each using BPAFLBi (abbreviation) and BPAFLP (abbreviation) had the characteristics as a light-emitting element and fully functions. Further, from the results of the reliability test, it was found that a highly reliable light-emitting element was obtained in which a short circuit due to defects of the film or the like was not caused even if the light-emitting element was made to emit light continuously.

Figure 29:
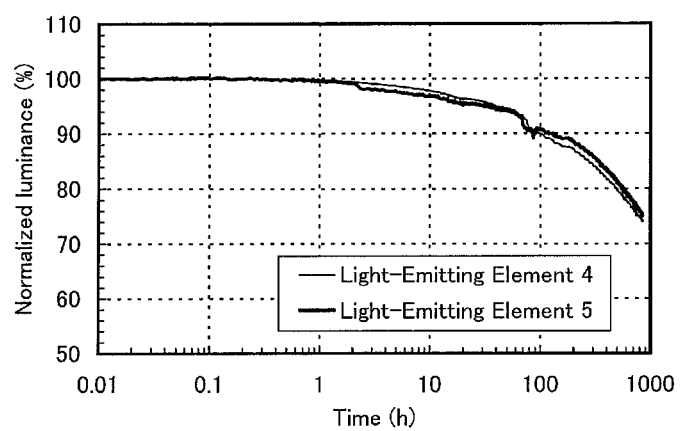
FIG. 29 is a graph showing results of a reliability test of Light-Emitting Element 4 and Light-Emitting Element 5.

FIG. 29 shows results of a continuous lighting test in which Light-Emitting Element 4 and Light-Emitting Element 5 were continuously lit by constant current driving with the initial luminance set at 1000 cd/m² (the vertical axis indicates the relative luminance on the assumption that 1000 cd/m² is 100%). From the results of FIG. 29, Light-Emitting Element 4 exhibits 74% of the initial luminance even after 850 hours and Light-Emitting Element 5 exhibits 75% of the initial luminance even after 850 hours, which leads to that Light-Emitting Element 4 and Light-Emitting Element 5 have a long lifetime. Therefore, it was found that a long-life light-emitting element can be obtained by application of BPAFLBi (abbreviation) and BPAFLP (abbreviation) of the present invention.

Example 6

In Example 6, a method for manufacturing Light-Emitting Element formed using 4-phenyl-4'-(9-phenylfluoren-9-yl)triphenylamine (abbreviation: BPAFLP), which is the fluorene derivative synthesized in Example 1 and measurement results of element characteristics are described.

The light-emitting element of Example 6 has an element structure illustrated in FIG. 18. The light-emitting element 6 is formed using the above-described fluorene derivative of the present invention for a hole-transport layer. Structural Formulae of an organic compound used in Example 6 are shown below.

[Chemical Formula 39]

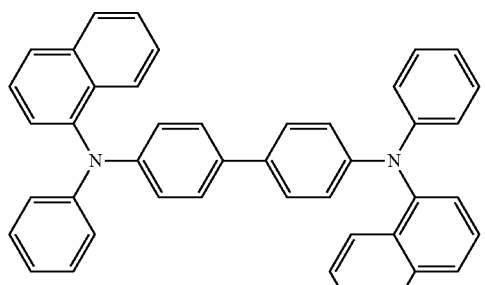

NPB

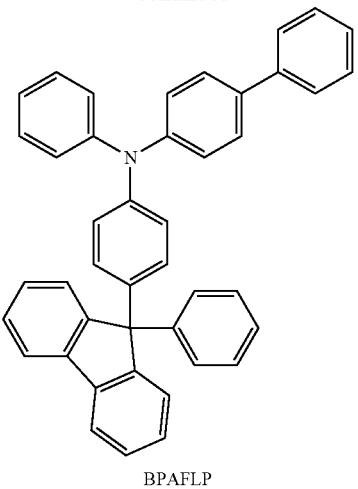

BPAFLP

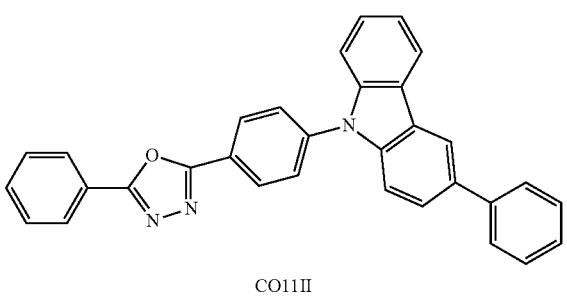

CO11II

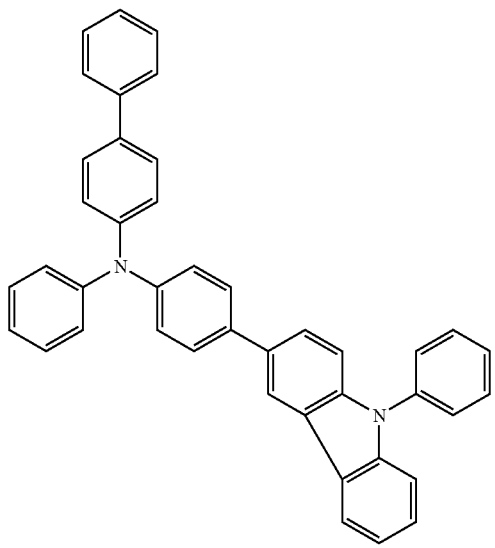

PCBA1BP

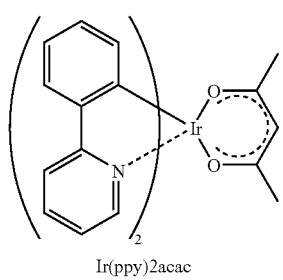

Ir(ppy)2acac

-continued

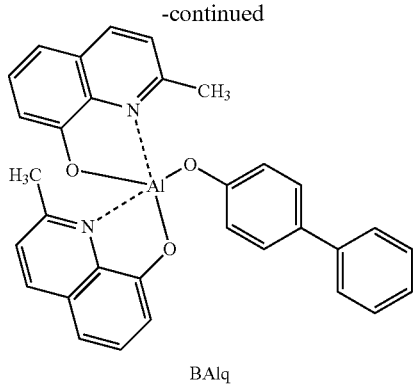

BAlq

First, indium oxide-tin oxide containing silicon oxide was deposited on a substrate 1501 which was a glass substrate by a sputtering method to form a first electrode 1502. Note that the thickness of the first electrode 1502 was 110 nm and the electrode area was 2 mm×2 mm.

Next, an EL layer 1503 including a stack of a plurality of layers is formed over the first electrode 1502. In Example 6, the EL layer 1503 has a structure in which a first layer 1511 which is a hole-injection layer, a second layer 1512 which is a hole-transport layer, a third layer 1513 which is a light-emitting layer, a fourth layer 1514 which is an electron-transport layer, and a fifth layer 1515 which is an electron-injection layer are sequentially stacked.

The substrate provided with the first electrode 1502 was fixed to a substrate holder which was provided in a vacuum evaporation apparatus so that a surface provided with the first electrode 1502 faced downward. The pressure in the vacuum evaporation apparatus was reduced to approximately $10^{-4}$ Pa. Then, over the first electrode 1502, 4,4'-bis[N-(1-naphthyl)-N-phenylamino]biphenyl (NPB) and molybdenum(VI) oxide were co-evaporated to form the first layer 1511 which was a hole-injection layer. The thickness was 50 nm, and the evaporation rate was controlled so that the weight ratio of NPB to molybdenum (VI) oxide could be 4:2=(NPB: molybdenum oxide). Note that the co-evaporation method is an evaporation method in which evaporation of a plurality of materials is performed from a plurality of evaporation sources at the same time in one treatment chamber.

Next, a hole-transport material was deposited on the first layer 1511 to a thickness of 10 nm by an evaporation method using resistance heating, and the second layer 1512 which was a hole-transport layer was formed. Note that Light-Emitting Element 6 was formed using 4-phenyl-4'-(9-phenylfluoren-9-yl)triphenylamine (abbreviation: BPAFLP) and Comparative Light-Emitting Element 7 was formed using 4,4'-bis [N-(1-naphthyl)-N-phenylamino]biphenyl (abbreviation: NPB).

Next, the third layer 1513 which was a light-emitting layer was formed on the second layer 1512 by an evaporation method using resistance heating. As the third layer 1513, 3-phenyl-9-[4-(5-phenyl-1,3,4-oxadiazol-2-yl)phenyl]-9H-carbazole (abbreviation: CO11II) and (2-phenylpyridinato-N,$C^{2'}$)iridium(III) acetylacetonato (abbreviation: Ir(ppy)$_2$ acac) were co-evaporated to form a 40-nm-thick film. Here, the evaporation rate was controlled so that the weight ratio of CO11II to Ir(ppy)$_2$acac was 1:0.08=(CO01II:Ir(ppy)$_2$acac).

Furthermore, on the third layer 1513, a 10-nm-thick film of bis(2-methyl-8-quinolinolato)(4-phenylphenolato)aluminum(III) (abbreviation: BAlq) and, thereon, a 20-nm-thick film of bathophenanthroline (abbreviation: BPhen) were formed by an evaporation method using resistance heating to form the fourth layer 1514 which was an electron-transport layer.

After that, in a manner similar to Comparative Light-Emitting Element 1, the fourth layer which was an electron-transport layer, the fifth layer which was an electron-injection layer, and a second electrode were formed. Thus, Light-Emitting Element 6 and Comparative Light-Emitting Element 7 were formed.

Note that Light-Emitting Element 6 and Comparative Light-Emitting Element 7 were formed in the same steps, except that of the second layer 1512.

Light-Emitting Element 6 and Comparative Light-Emitting Element 7 thus obtained were sealed in a glove box having a nitrogen atmosphere without being exposed to the air. Then, the operating characteristics thereof were measured. Note that the measurement was carried out at room temperature (in an atmosphere kept at 25° C.).

Figure 30:
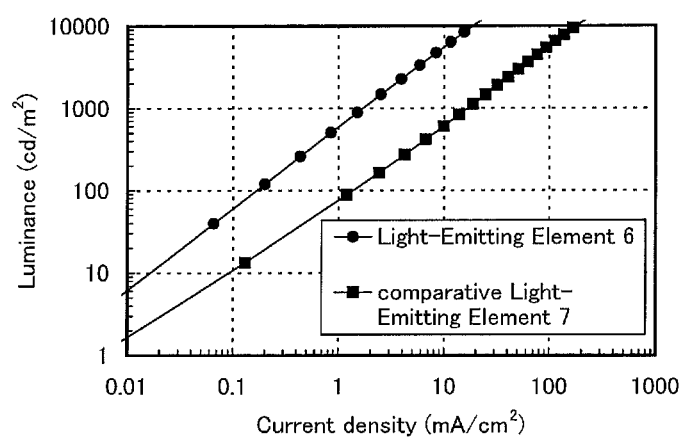
FIG. 30 is a graph showing current density vs. luminance characteristics of Light-Emitting Element 6 and Comparative Light-Emitting Element 7.
Figure 31:
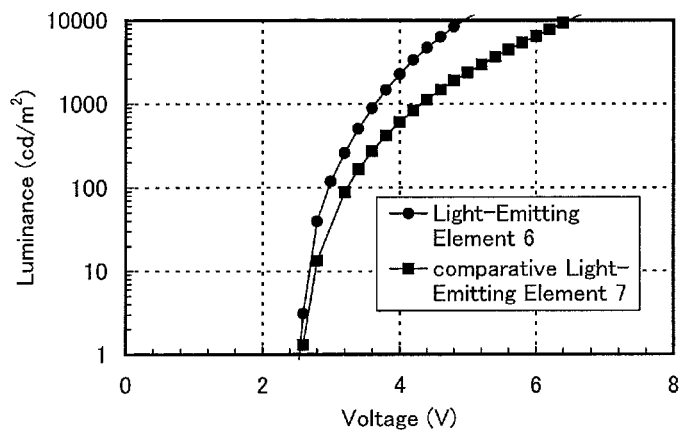
FIG. 31 is a graph showing voltage vs. luminance characteristics of Light-Emitting Element 6 and Comparative Light-Emitting Element 7.
Figure 32:
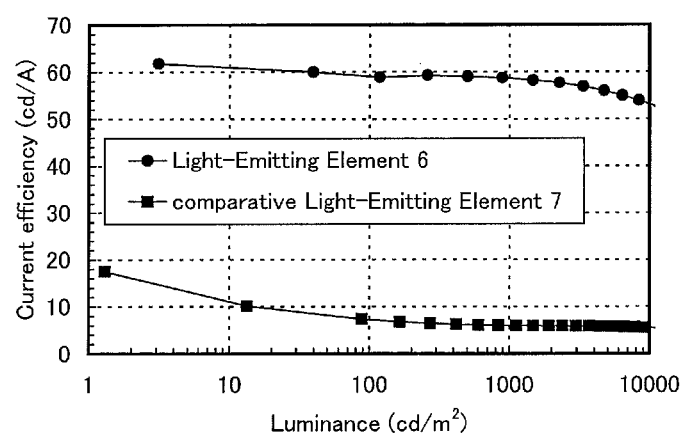
FIG. 32 is a graph showing luminance vs. current efficiency characteristics of Light-Emitting Element 6 and Comparative Light-Emitting Element 7.

FIG. 30 shows the current density vs. luminance characteristics of Light-Emitting Element 6 and Comparative Light-Emitting Element 7. FIG. 31 shows the voltage vs. luminance characteristics of Light-Emitting Element 6 and Comparative Light-Emitting Element 7. FIG. 32 shows the luminance vs. current efficiency characteristics of Light-Emitting Element 6 and Comparative Light-Emitting Element 7. In FIG. 30, the vertical axis represents luminance (cd/m$^2$) and the horizontal axis represents current density (mA/cm$^2$). In FIG. 31, the vertical axis represents luminance (cd/m$^2$) and the horizontal axis represents voltage (V). In FIG. 32, the vertical axis represents current efficiency (cd/A) and the horizontal axis represents luminance (cd/m$^2$). In addition, Table 4 shows the voltage, chromaticity, current efficiency, and external quantum efficiency of Light-Emitting Element 6 and Comparative Light-Emitting Element 7 at around 1000 cd/m$^2$.

TABLE 4

|  | Voltage (V) | Chromaticity x | Chromaticity y | Current efficiency (cd/A) | Quantum efficiency (%) |
|---|---|---|---|---|---|
| Light-Emitting Element 6 | 3.6 | 0.36 | 0.61 | 59 | 16 |
| Comparative Light-Emitting Element 7 | 4.4 | 0.34 | 0.57 | 6.0 | 1.7 |

Figure 33:
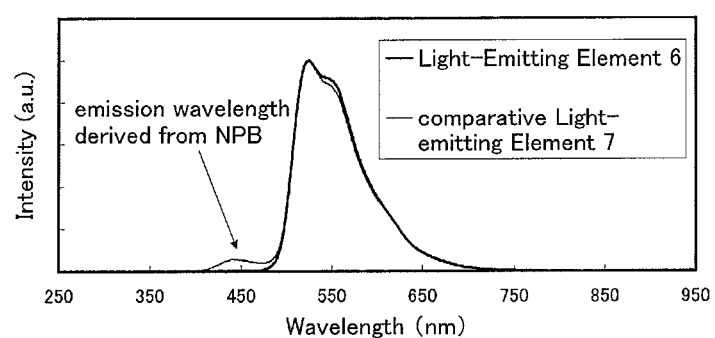
FIG. 33 is a graph showing emission spectra of Light-Emitting Element 6 and Comparative Light-Emitting Element 7.

FIG. 33 shows emission spectra of Light-Emitting Element 6 and Comparative Light-Emitting Element 7.

As shown in FIG. 33, in Comparative Light-Emitting Element 7, an emission wavelength derived from NPB of a hole-transport layer in addition to an emission wavelength derived from a dopant was observed. This indicates that NPB has low ability to block electrons, whereby recombination partly occurs even in NPB which has low internal quantum efficiency. As a result, it is considered that the current efficiency and external quantum efficiency were decreased. Further, it is thought that since NPB has low triplet excitation energy, triplet excitation energy is likely to transfer from the light-emitting layer to NPB, which causes decrease in the current efficiency and external quantum efficiency. On the other hand, in Light-Emitting Element 6, only an emission derived from a dopant in the light-emitting layer was observed and an emission derived from BPAFLP (abbreviation) in the hole-transport layer was not observed. Accordingly, it is indicated that BPAFLP has high ability to block electrons and also has large triplet excitation energy. As a result, generated excitation energy was consumed mainly by a dopant which was a phosphorescent material in the light-emitting layer to form light, whereby high current efficiency can be obtained. Thus, it was confirmed that an element having high efficiency can be obtained with use of BPAFLP (abbreviation) of an embodiment of the present invention for the hole-transport layer.

Example 7

In Example 7, a method for manufacturing Light-Emitting Element formed each using 4-phenyl-4'-(9-phenylfluoren-9-yl)triphenylamine (abbreviation: BPAFLP), which is the fluorene derivative synthesized in Example 1 and measurement results of element characteristics is described.

Each of Light-Emitting Element 8 to Light-Emitting Element 10 of Example 7 has an element structure illustrated in FIG. 18. Light-Emitting Element 9 was formed using the above-described fluorine derivative of the present invention for a transporting layer, and Light-Emitting Element 10 was formed using the above-described fluorine derivative of the present invention for a hole-injection layer and a hole-transport layer, respectively. Structural Formulae of an organic compound used in Example 7 are shown below.

[Chemical Formula 40]

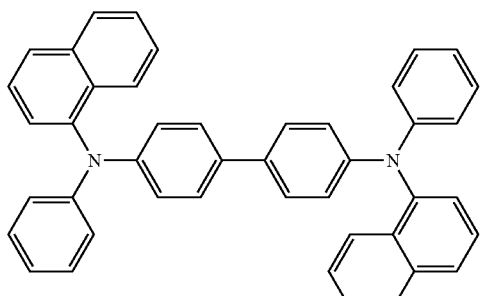

NPB

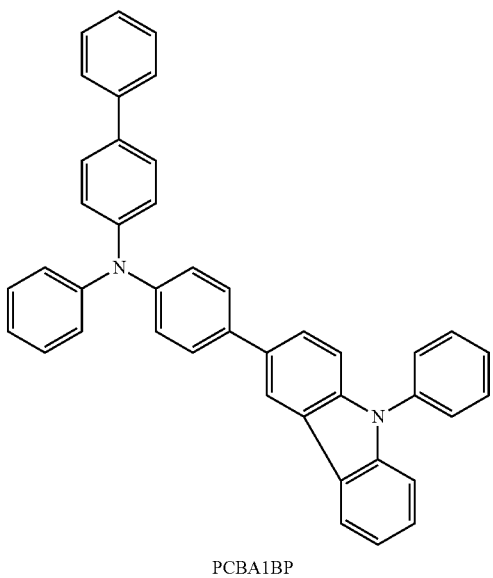

PCBA1BP

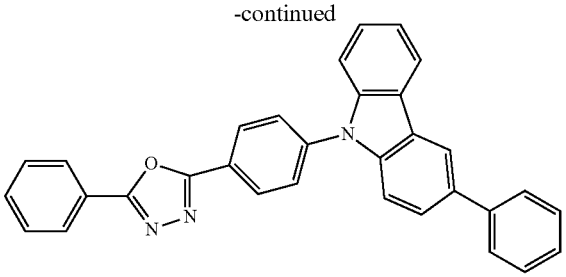

CO11II

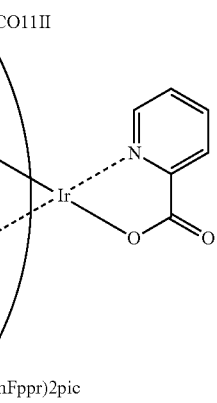

Ir(dmFppr)2pic

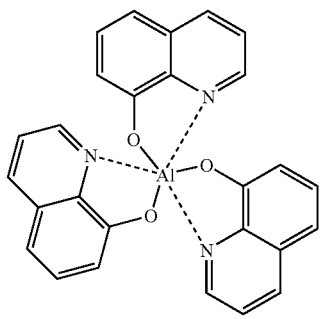

Alq

First, indium oxide-tin oxide containing silicon oxide was deposited on a substrate 1501 which was a glass substrate by a sputtering method to form a first electrode 1502. Note that the thickness of the first electrode 1502 was 110 nm and the electrode area was 2 mm×2 mm.

Next, an EL layer 1503 including a stack of a plurality of layers is formed over the first electrode 1502. In Example 7, the EL layer 1503 has a structure in which a first layer 1511 which is a hole-injection layer, a second layer 1512 which is a hole-transport layer, a third layer 1513 which is a light-emitting layer, a fourth layer 1514 which is an electron-transport layer, and a fifth layer 1515 which is an electron-injection layer are sequentially stacked.

The substrate provided with the first electrode 1502 was fixed to a substrate holder which was provided in a vacuum evaporation apparatus so that a surface provided with the first electrode 1502 faced downward. The pressure in the vacuum evaporation apparatus was reduced to approximately $10^{-4}$ Pa. Then, over the first electrode 1502, a hole-injection material was deposited to a thickness of 50 nm to form the first layer 1511 which was a hole-injection layer. Note that when Light-Emitting Element 8 and Light-Emitting Element 9 were formed, 4,4'-bis[N-(1-naphthyl)-N-phenylamino]biphenyl (abbreviation: NPB) and molybdenum(VI) oxide were co-evaporated to form the first layer 1511 which was a hole-injection layer 1511. The thickness was 50 nm, and the evaporation rate was controlled so that the weight ratio of NPB to molybdenum (VI) oxide could be 4:2=(NPB: molybdenum oxide). Further, when Light-Emitting Element 10 was formed, 4-phenyl-4'-(9-phenylfluoren-9-yl)triphenylamine (abbreviation: BPAFLP) and molybdenum(VI) oxide were co-evaporated to form the first layer 1511 which was a hole-injection layer. The thickness was 50 nm, and the evaporation rate was controlled so that the weight ratio of BPAFLP to molybdenum (VI) oxide could be 4:2=(BPAFLP: molybdenum oxide).

Next, a hole-transport material was deposited on the first layer 1511 to a thickness of 10 nm by an evaporation method using resistance heating, and the second layer 1512 which was a hole-transport layer was formed. Note that Light-Emitting Element 8 was formed using 4-phenyl-4'-(9-phenyl-9H-carbazol-3-yl)triphenylamine (abbreviation: PCBA1BP)] and Light-Emitting Element 9 and Light-Emitting Element 10 were formed using 4-phenyl-4'-(9-phenylfluoren-9-yl) triphenylamine (abbreviation: BPAFLP).

Next, the third layer 1513 which was a light-emitting layer was formed on the second layer 1512 by an evaporation method using resistance heating. As the third layer 1513, 3-phenyl-9-[4-(5-phenyl-1,3,4-oxadiazol-2-yl)phenyl]-9H-carbazole (abbreviation: CO11II), 4-phenyl-4'-(9-phenyl-9H-carbazol-3-yl)triphenylamine (abbreviation: PCBA1BP), and bis{2-(4-fluorophenyl)-3,5-dimethylpyridinato}(picolinate)iridium(III) (abbreviation: Ir(dmFppr)$_2$pic) were co-evaporated to form a 40-nm-thick film. Here, the evaporation rate was controlled so that the weight ratio of CO11II to PCBA1BP and Ir(dmFppr)$_2$pic) was 1:0.15:0.1= (CO11II:PCBA1BP:Ir(dmFppr)$_2$pic)).

After that, in a manner similar to Comparative Light-Emitting Element 1, the fourth layer which was an electron-transport layer, the fifth layer which was an electron-injection layer, and a second electrode were formed. Thus, Light-Emitting Element 8 to Light-Emitting Element 10 were formed.

Note that Light-Emitting Element 8 to Light-Emitting Element 10 were formed in the same steps, except those of the first layer 1511 and the second layer 1512.

Light-Emitting Element 8 to Light-Emitting Element 10 thus obtained were sealed in a glove box having a nitrogen atmosphere without being exposed to the air. Then, the operating characteristics thereof were measured. Note that the measurement was carried out at room temperature (in an atmosphere kept at 25° C.).

Figure 34:
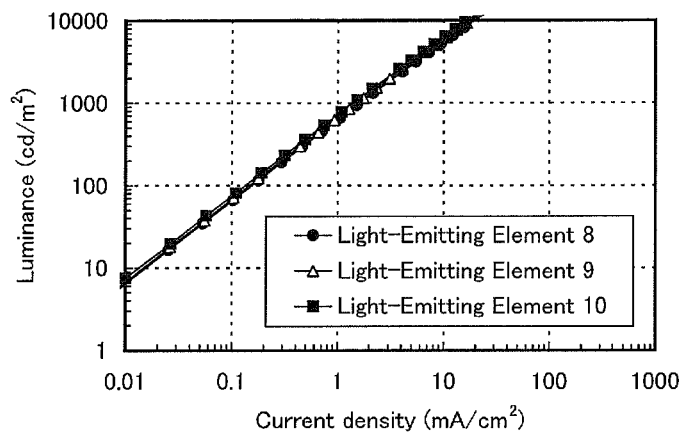
FIG. 34 is a graph showing current density vs. luminance characteristics of Light-Emitting Element 8 to Light-Emitting Element 10.
Figure 35:
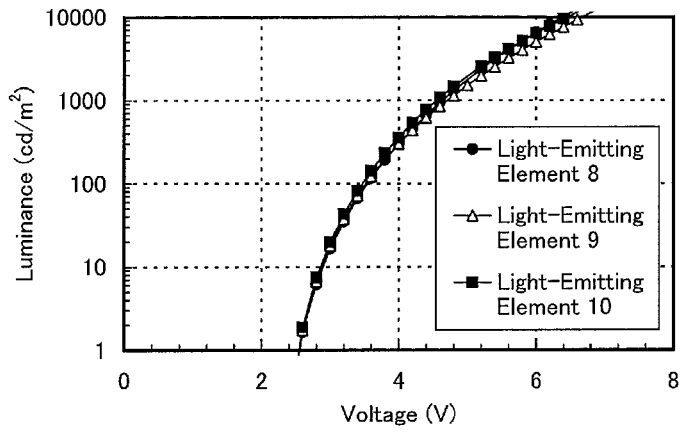
FIG. 35 is a graph showing voltage vs. luminance characteristics of Light-Emitting Element 8 to Light-Emitting Element 10.
Figure 36:
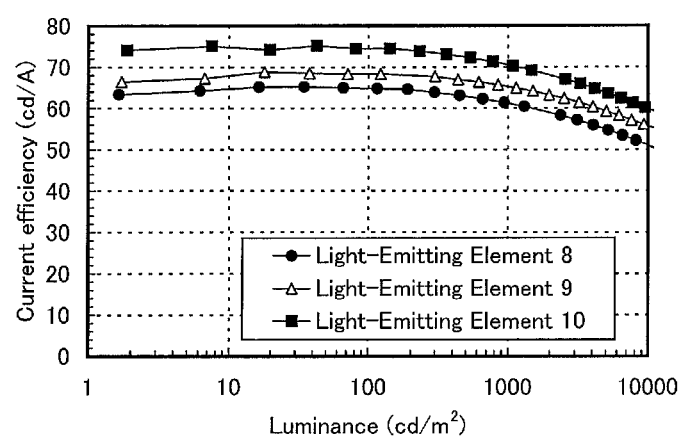
FIG. 36 is a graph showing luminance vs. current efficiency characteristics of Light-Emitting Element 8 to Light-Emitting Element 10.

FIG. 34 shows the current density vs. luminance characteristics of Light-Emitting Element 8 to Light-Emitting Element 10. FIG. 35 shows the voltage vs. luminance characteristics of Light-Emitting Element 8 to Light-Emitting Element 10. FIG. 36 shows the luminance vs. current efficiency characteristics of Light-Emitting Element 8 to Light-Emitting Element 10. In FIG. 34, the vertical axis represents luminance (cd/m$^2$) and the horizontal axis represents current density (mA/cm$^2$). In FIG. 35, the vertical axis represents luminance (cd/m$^2$) and the horizontal axis represents voltage (V). In FIG. 36, the vertical axis represents current efficiency (cd/A) and the horizontal axis represents luminance (cd/m$^2$). In addition, Table 5 shows the voltage, chromaticity, current efficiency, and external quantum efficiency of Light-Emitting Element 8 to Light-Emitting Element 10 at around 1000 cd/m$^2$.

TABLE 5

|  | Voltage (V) | Chromaticity x | Chromaticity y | Current efficiency (cd/A) | Quantum efficiency (%) |
|---|---|---|---|---|---|
| Light-Emitting Element 8 | 4.6 | 0.41 | 0.58 | 61 | 17 |
| Light-Emitting Element 9 | 4.8 | 0.41 | 0.58 | 65 | 18 |
| Light-Emitting Element 10 | 4.6 | 0.40 | 0.58 | 70 | 19 |

High luminous efficiency can be obtained in each of Light-Emitting Element 8 to Light-Emitting Element 10; however, it was found that Light-Emitting Element 9 using BPAFLP for the hole-transport layer had higher current efficiency than Light-Emitting Element 8. Further, it was found that Light-Emitting Element 10 using BPAFLP for both the hole-injection layer and the hole-transport layer had higher current efficiency than Light-Emitting Element 9.

Figure 37:
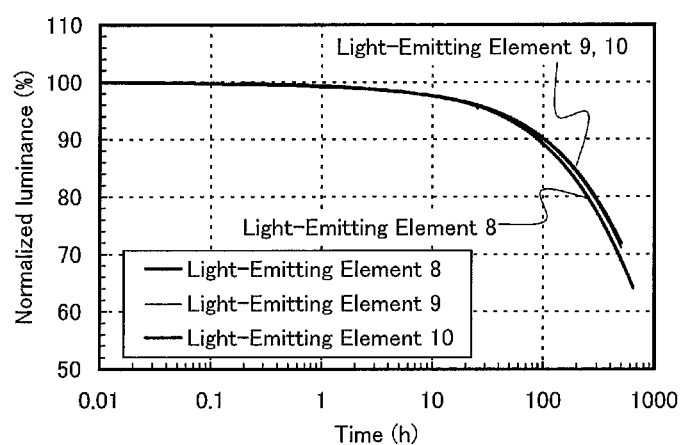
FIG. 37 is a graph showing results of a reliability test of Light-Emitting Element 8 to Light-Emitting Element 10.

FIG. 37 shows results of a continuous lighting test in which Light-Emitting Element 8 to Light-Emitting Element 10 were continuously lit by constant current driving with the initial luminance set at 1000 cd/m$^2$ (the vertical axis indicates the relative luminance on the assumption that 1000 cd/m$^2$ is 100%). From the results of FIG. 37, Light-Emitting Element 8 exhibits 64% of the initial luminance even after 650 hours. Light-Emitting Element 9 exhibits 71% of the initial luminance even after 500 hours and Light-Emitting Element 10 exhibits 72% of the initial luminance even after 500 hours. Therefore, it was found that a long-life light-emitting element can be obtained by application of BPAFLP (abbreviation) of an embodiment of the present invention.

Example 8

Here, simulation results which indicate the fluorene derivative of an embodiment of the present invention is suitable for a hole-transport material are shown.

Structural Formulae used in the simulation are shown below.

[Chemical Formula 41]

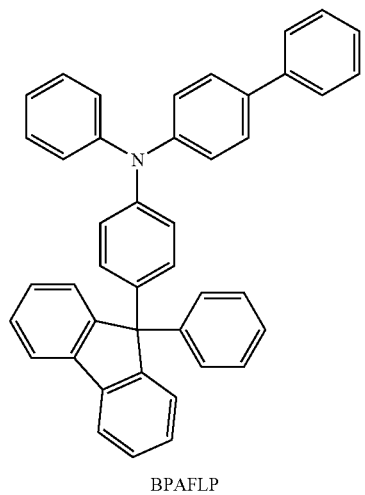

BPAFLP

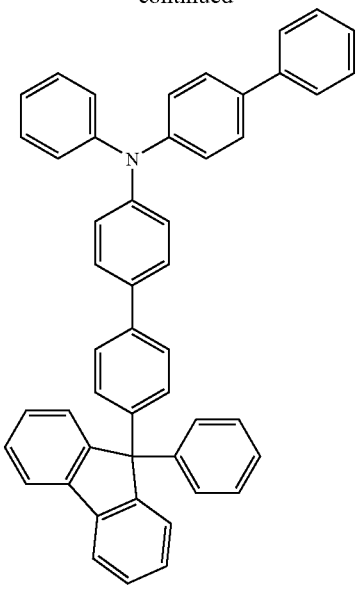

BPAFLBi

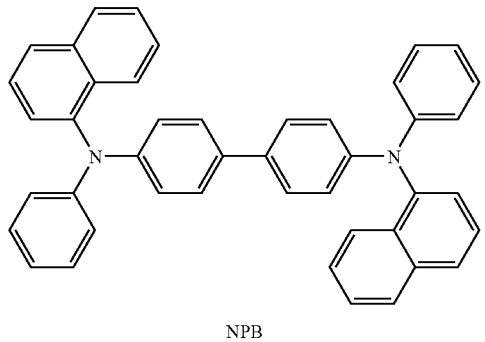

NPB

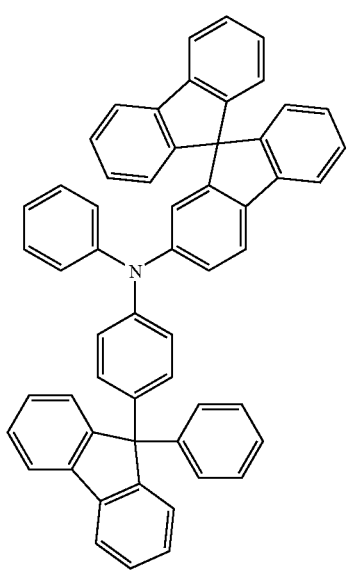

(109)

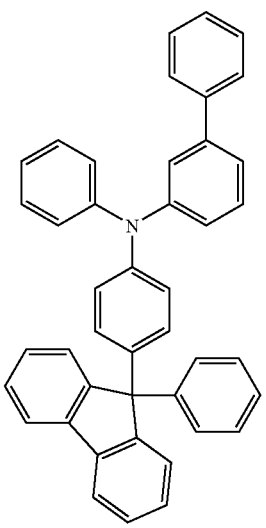

(114)

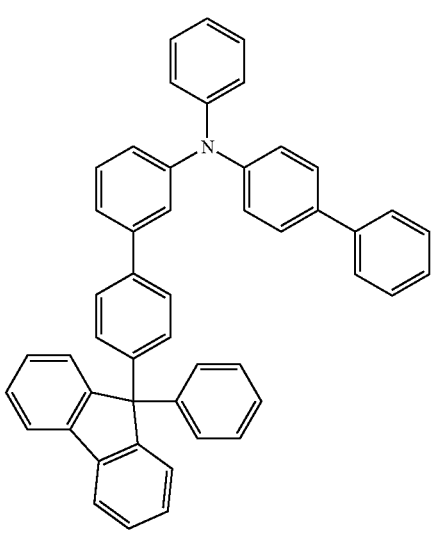

(164)

First, the most stable structures of Structural Formula (101) (abbreviation: BPAFLP), Structural Formula (109), Structural Formula (114), Structural Formula (151) (abbreviation: BPAFLBi), Structural Formula (164), and NPB in the singlet state and the triplet state were calculated using a density functional theory (TDDFT). Gaussian 03 was used as a quantum chemistry computational program. As a basis function, 6-311G (d, p) was used for H, C, and N atoms. As a functional, B3LYP was used.

Next, excitation energy of Structural Formula (101) (abbreviation: BPAFLP), Structural Formula (109), Structural Formula (114), Structural Formula (151) (abbreviation: BPAFLBi), Structural Formula (164), and NPB was each calculated with use of the most stable structures in the singlet state and the triplet state which were obtained by the above calculation, by time-dependent density functional theory. The basis function and functional used for this calculation were the same as those described above.

Table 6 shows the results of energy levels of the highest occupied molecular orbital (HOMO) level of the most stable structures in the singlet state obtained by the above calculation.

TABLE 6

| Singlet state | Structural Formula (101) BPAFLP | Structural Formula (109) | Structural Formula (114) | Structural Formula (151) BPAFLBi | Structural Formula (164) | NPB |
|---|---|---|---|---|---|---|
| Energy levels of HOMO | −5.13 eV | −5.04 eV | −5.18 eV | −5.13 eV | −5.18 eV | −4.97 eV |

From the results of Table 6, it was found that the above fluorene derivative had the lower HOMO energy level than NPB. Thus, it was proved that in the case where any of the above fluorene derivatives was used as a hole-transport material, the fluoren derivatives have excellent hole-injection property into a light-emitting layer having a deeper HOMO level in comparison with NPB.

Table 7 shows the results of the first excitation energy (singlet) of the most stable structures in the singlet state obtained by calculation using TDDFT

TABLE 7

| The most stable structures in the singlet state | Structural Formula (101) BPAFLP | Structural Formula (109) | Structural Formula (114) | Structural Formula (151) BPAFLBi | Structural Formula (164) | NPB |
|---|---|---|---|---|---|---|
| The first excitation energy (singlet) | 2.85 eV | 2.67 eV | 3.01 eV | 2.76 eV | 2.84 eV | 2.50 eV |

From the results of Table 7, it was found that in the case where any of the above fluorene derivatives was used as a hole-transport material, the fluorene derivatives hardly released singlet excitons at the boundary between the light-emitting layer and the hole-transport layer to the hole-transport layer side in comparison with NPB.

Table 8 shows the results of the first excitation energy (triplet) of the most stable structures in the triplet state obtained by calculation using TDDFT

TABLE 8

| The most stable structures in the triplet state | Structural Formula (101) BPAFLP | Structural Formula (109) | Structural Formula (114) | Structural Formula (151) BPAFLBi | Structural Formula (164) | NPB |
|---|---|---|---|---|---|---|
| The first excitation energy (triplet) | 1.98 eV | 2.03 eV | 2.15 eV | 1.98 eV | 1.98 eV | 1.74 eV |

From the results of Table 8, it was found that in a case where any of the above fluorene derivatives was used as a hole-transport material, the fluorene derivatives hardly released triplet excitons at the boundary between the light-emitting layer and the hole-transport layer from the light-emitting layer to the hole-transport layer side, in comparison with NPB. Further, it was found that in a case where any of the fluorene derivatives was used as a phosphorescent host material, a guest material was easily excited.

Example 9

In Example 9, a method for manufacturing Light-Emitting Element formed using 4-phenyl-4'-(9-phenylfluoren-9-yl) triphenylamine (abbreviation: BPAFLP), which is the fluorene derivative synthesized in Example 1 and measurement results of element characteristics is described.

An element structure of each of Light-Emitting Element 11 and Comparative Light-Emitting Element 12 in Example 9 is illustrated in FIG. 18. Light-Emitting Element 11 was formed using the above-described fluorene derivative of the present invention for a hole-injection layer and a hole-transport layer.

First, indium oxide-tin oxide containing silicon oxide was deposited on a substrate 1501 which was a glass substrate by a sputtering method to form a first electrode 1502. Note that the thickness of the first electrode 1502 was 110 nm and the electrode area was 2 mm×2 mm.

Next, an EL layer 1503 including a stack of a plurality of layers is formed over the first electrode 1502. In Example 9, the EL layer 1503 has a structure in which a first layer 1511 which is a hole-injection layer, a second layer 1512 which is a hole-transport layer, a third layer 1513 which is a light-emitting layer, a fourth layer 1514 which is an electron-transport layer, and a fifth layer 1515 which is an electron-injection layer are sequentially stacked.

The substrate provided with the first electrode 1502 was fixed to a substrate holder which was provided in a vacuum evaporation apparatus so that a surface provided with the first electrode 1502 faced downward. The pressure in the vacuum evaporation apparatus was reduced to approximately $10^{-4}$ Pa. Then, over the first electrode 1502, a hole-injection material was deposited to a thickness of 50 nm to form the first layer 1511 which was a hole-injection layer. When Light-Emitting Element 11 was formed, 4-phenyl-4'-(9-phenylfluoren-9-yl)triphenylamine (abbreviation: BPAFLP) and molybdenum (VI) oxide were co-evaporated to form the first layer 1511 which was a hole-injection layer 1511. The thickness was 50 nm, and the evaporation rate was controlled so that the weight ratio of BPAFLP to molybdenum (VI) oxide could be 4:2= (BPAFLP: molybdenum oxide). Further, when Comparative Light-Emitting Element 12 was formed, 4,4',4"-tris(carbazol-9-yl)triphenylamine (abbreviation: TCTA) and molybdenum(VI) oxide were co-evaporated to form the first layer 1511 which was a hole-injection layer. The thickness was 50 nm, and the evaporation rate was controlled so that the weight ratio of TCTA to molybdenum (VI) oxide could be 4:2= (TCTA: molybdenum oxide).

Next, a hole-transport material was deposited on the first layer 1511 to a thickness of 10 nm by an evaporation method using resistance heating, and the second layer 1512 which was a hole-transport layer was formed. Note that Light-Emitting Element 11 was formed using 4-phenyl-4'-(9-phenylfluoren-9-yl)triphenylamine (abbreviation: BPAFLP) and Comparative Light-Emitting Element 12 was formed using 4,4',4"-tris(carbazol-9-yl)triphenylamine (abbreviation: TCTA).

Next, the third layer 1513 which was a light-emitting layer was formed on the second layer 1512 by an evaporation method using resistance heating. As the third layer, 9-[4-(4,5-diphenyl-4H-1,2,4-triazol-3-yl)phenyl]-9H-carbazole (abbreviation: CzTAZ1) and bis[2-(4',6'-difluorophenyl)pyridinato-N,$C^{2'}$]iridium(III)picolinate (abbreviation: FIrpic) were co-evaporated to form a 30-nm-thick film. Here, the evaporation rate was controlled so that the weight ratio of CzTAZ1 to FIrpic was 1:0.06=(CzTAZ1: FIrpic).

Furthermore, on the third layer 1513, a 10-nm-thick film of 3-(4-biphenylyl)-4-phenyl-5-(4-tert-butylphenyl)-1,2,4-triazole (abbreviated designation: TAZ01) and, thereon, a 20-nm-thick film of bathophenanthroline (abbreviation: BPhen) were formed by an evaporation method using resistance heating to form the fourth layer 1514 which was an electron-transport layer.

After that, in a manner similar to Comparative Light-Emitting Element 1, the fifth layer which was an electron-injection layer and a second electrode were formed. Thus, Light-Emitting Element 11 and Comparative Light-Emitting Element 12 were formed.

Note that Light-Emitting Element 11 and Comparative Light-Emitting Element 12 were formed in the same steps, except those of the first layer 1511 and the second layer 1512.

Light-Emitting Element 11 and Comparative Light-Emitting Element 12 thus obtained were sealed in a glove box having a nitrogen atmosphere without being exposed to the air. Then, the operating characteristics thereof were measured. Note that the measurement was carried out at room temperature (in an atmosphere kept at 25° C.).

Figure 38:
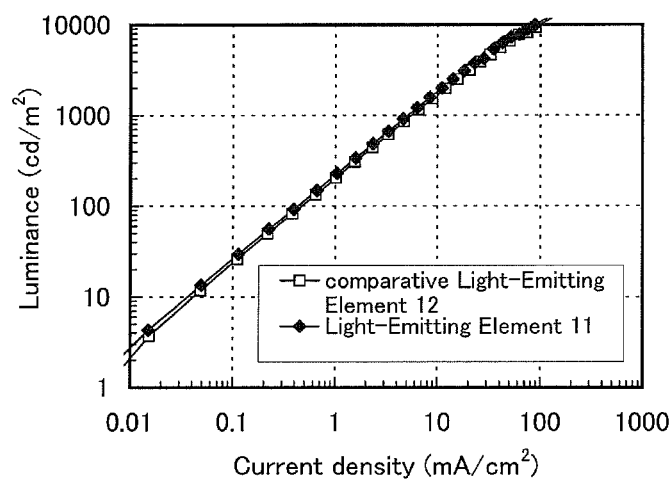
FIG. 38 is a graph showing current density vs. luminance characteristics of Light-Emitting Element 11 and comparative Light-Emitting Element 12.
Figure 39:
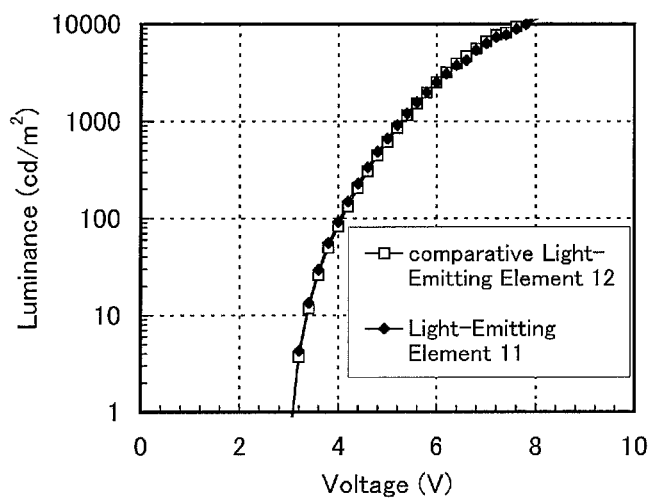
FIG. 39 is a graph showing voltage vs. luminance characteristics of Light-Emitting Element 11 and comparative Light-Emitting Element 12.
Figure 40:
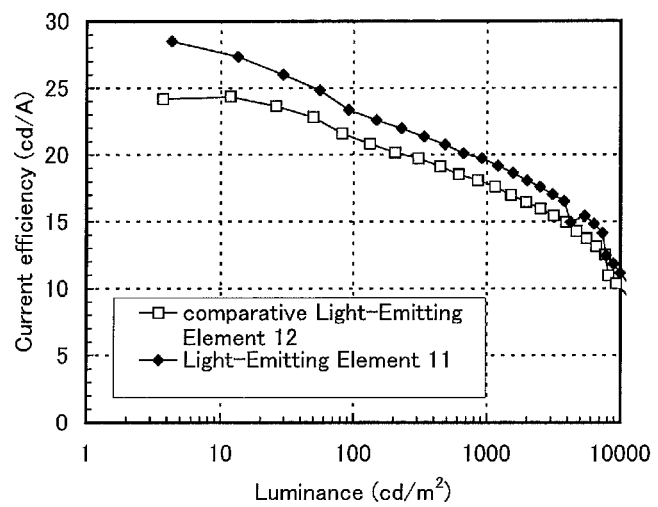
FIG. 40 is a graph showing luminance vs. current efficiency characteristics of Light-Emitting Element 11 and comparative Light-Emitting Element 12.

FIG. 38 shows the current density vs. luminance characteristics of Light-Emitting Element 11 and Comparative Light-Emitting Element 12. FIG. 39 shows the voltage vs. luminance characteristics of Light-Emitting Element 11 and Comparative Light-Emitting Element 12. FIG. 40 shows the luminance vs. current efficiency characteristics of Light-Emitting Element 11 and Comparative Light-Emitting Element 12. In FIG. 38, the vertical axis represents luminance (cd/m$^2$) and the horizontal axis represents current density (mA/cm$^2$). In FIG. 39, the vertical axis represents luminance (cd/m$^2$) and the horizontal axis represents voltage (V). In FIG. 40, the vertical axis represents current efficiency (cd/A) and the horizontal axis represents luminance (cd/m$^2$). In addition, Table 9 shows the voltage, chromaticity, current efficiency, and external quantum efficiency of Light-Emitting Element 11 and Comparative Light-Emitting Element 12 around 1000 cd/m$^2$.

TABLE 9

|  | Voltage (V) | Chromaticity x | Chromaticity y | Current efficiency (cd/A) | Quantum efficiency (%) |
|---|---|---|---|---|---|
| Light-Emitting Element 11 | 5.2 | 0.19 | 0.37 | 20 | 9.2 |
| Comparative Light-Emitting Element 12 | 5.2 | 0.19 | 0.37 | 18 | 8.4 |

When the drive voltage of Light-Emitting Element 11 in which the fluorene derivative BPAFLP (abbreviation) of the present invention was used for the first layer 1511 and the second layer 1512, was 5.2 V, the luminance was 910 cd/m$^2$ and the current value was 0.18 mA. When the drive voltage of Comparative Light-Emitting Element 12 in which TCTA (abbreviation) was used instead of BPAFLP (abbreviation) was 5.2 V, the luminance was 850 cd/m$^2$ and the current value was 0.19 mA. Thus, it was confirmed that Light-Emitting Element 11 in which BPAFLP (abbreviation) was used for the first layer 1511 and the second layer 1512 has higher current efficiency than Comparative Light-Emitting Element 12. It was found that by application of BPAFLP (abbreviation) of an embodiment of the present invention to the hole-injection layer and the hole-transport layer, a light-emitting element with high efficiency can be obtained.

Figure 41:
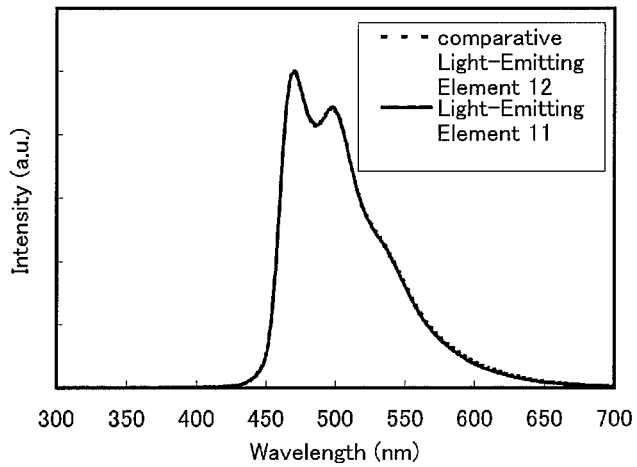
FIG. 41 is a graph showing emission spectra of Light-Emitting Element 11 and comparative Light-Emitting Element 12.

FIG. 41 shows emission spectra of Light-Emitting Element 11 and Comparative Light-Emitting Element 12.

In both Light-Emitting Element 11 and Comparative Light-Emitting Element 12, an emission spectrum derived from FIrpic (abbreviation) which was a phosphorescent dopant material was observed, and an emission derived from a layer adjacent to the third layer 1513 was not observed. This shows that in both of the elements, carriers were preferably recombined in the third layer 1513, and light could be emitted in favorable carrier balance. It was indicated that since Light-Emitting Element 11 showed higher current efficiency than Comparative Light-Emitting Element 12 at this time, BPAFLP (abbreviation) had more favorable carrier balance (blocked electrons from the third layer 1513 and made more holes flow to the third layer 1513) and the triplet excitation energy was also high. At this time, the LUMO level of BPAFLP (abbreviation) of an embodiment of the present invention was almost the same as that of TCTA (abbreviation) (−2.30 eV) and band gap (Bg) of BPAFLP (abbreviation) was narrower than that of TCTA (abbreviation) (3.40 eV); therefore, BPAFLP (abbreviation) of an embodiment of the present invention was a material having higher hole-transport property. Accordingly, it was thought that carrier recombination can be efficiently performed in the light-emitting layer, so that higher efficiency can be obtained.

Example 10

In Example 10, a method for manufacturing a light-emitting element formed using 4-phenyl-4'-(9-phenylfluoren-9-yl)triphenylamine (abbreviation: BPAFLP), which is the fluorene derivative synthesized in Example 1 and measurement results of element characteristics are described.

An element structure of Light-Emitting Element 13 in Example 10 is illustrated in FIG. 18. Light-Emitting Element 13 was formed using the above-described fluorene derivative (abbreviation: BPAFLP) of the present invention for the hole-injection layer and the hole-transport layer. A structural formula of an organic compound which was used in Example 10 is shown below.

First, indium oxide-tin oxide containing silicon oxide was deposited on a substrate 1501 which was a glass substrate by a sputtering method to form a first electrode 1502. Note that the thickness of the first electrode 1502 was 110 nm and the electrode area was 2 mm×2 mm.

Next, an EL layer 1503 including a stack of a plurality of layers is formed over the first electrode 1502. In Example 9, the EL layer 1503 has a structure in which a first layer 1511 which is a hole-injection layer, a second layer 1512 which is a hole-transport layer, a third layer 1513 which is a light-emitting layer, a fourth layer 1514 which is an electron-transport layer, and a fifth layer 1515 which is an electron-injection layer are sequentially stacked.

The substrate provided with the first electrode 1502 was fixed to a substrate holder which was provided in a vacuum evaporation apparatus so that a surface provided with the first electrode 1502 faced downward. The pressure in the vacuum evaporation apparatus was reduced to approximately $10^{-4}$ Pa. Then, over the first electrode 1502, a hole-injection material was deposited to a thickness of 50 nm to form the first layer 1511 which was a hole-injection layer. When Light-Emitting Element 13 was formed, 4-phenyl-4'-(9-phenylfluoren-9-yl)triphenylamine (abbreviation: BPAFLP) and molybdenum (VI) oxide were co-evaporated to form the first layer 1511 which was a hole-injection layer 1511. The thickness was 50 nm, and the evaporation rate was controlled so that the weight ratio of BPAFLP to molybdenum (VI) oxide could be 4:2= (BPAFLP: molybdenum oxide).

Next, a hole-transport material was deposited on the first layer 1511 to a thickness of 10 nm by an evaporation method using resistance heating, and the second layer 1512 which was a hole-transport layer was formed. Note that Light-Emitting Element 13 was formed using 4-phenyl-4'-(9-phenylfluoren-9-yl)triphenylamine (abbreviation: BPAFLP).

Next, the third layer 1513 which was a light-emitting layer was formed on the second layer 1512 by an evaporation method using resistance heating. As the third layer 1513, 4-[3-(triphenylen-2-yl)phenyl]dibenzothiophene (abbreviation: mDBTPTp-II) and tris(2-phenylpyridinato-N,$C^{2'}$)iridium(III) (abbreviation: Ir(ppy)$_3$) were co-evaporated to form a 40-nm-thick film. Here, the evaporation rate was controlled so that the weight ratio of mDBTPTp-II to Ir(ppy)$_3$ was 1:0.08=(mDBTPTp-II:Ir(ppy)$_3$).

Furthermore, on the third layer 1513, a 10-nm-thick film of mDBTPTp-II and, thereon, a 20-nm-thick film of bathophenanthroline (abbreviation: BPhen) were formed by an evaporation method using resistance heating to form the fourth layer 1514 which was an electron-transport layer.

After that, in a manner similar to Comparative Light-Emitting Element 1, the fifth layer which was an electron-injection layer and a second electrode were formed. Thus, Light-Emitting Element 13 was formed.

Light-Emitting Element 13 thus obtained was sealed in a glove box having a nitrogen atmosphere without being exposed to the air. Then, the operating characteristics of Light-Emitting Element 13 were measured. Note that the measurement was carried out at room temperature (in an atmosphere kept at 25° C.).

Figure 42:
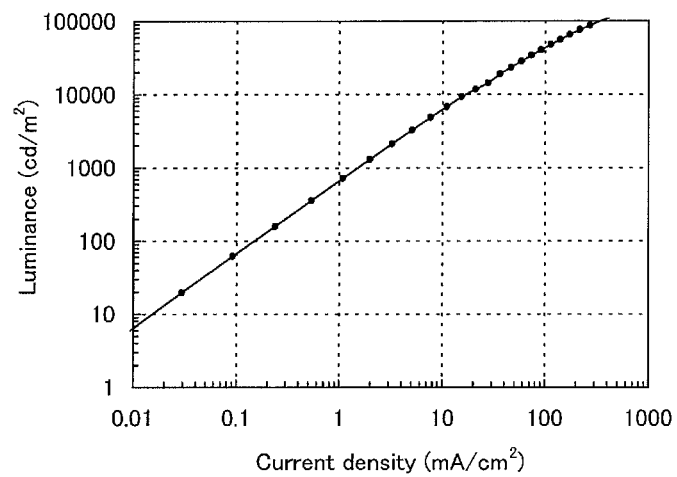
FIG. 42 is a graph showing current density vs. luminance characteristics of Light-Emitting Element 13.
Figure 43:
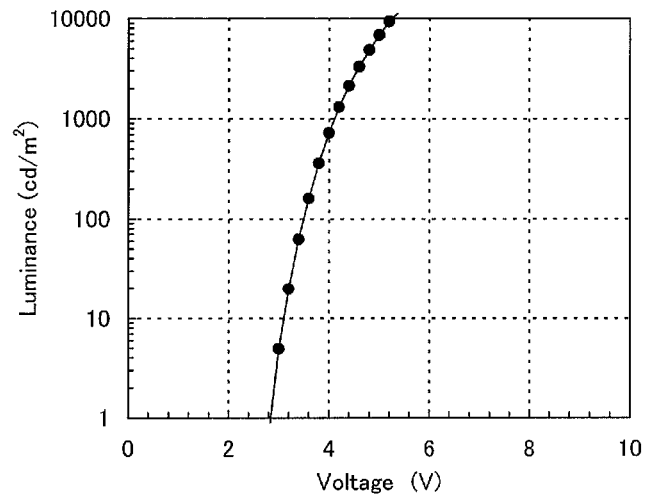
FIG. 43 is a graph showing voltage vs. luminance characteristics of Light-Emitting Element 13.
Figure 44:
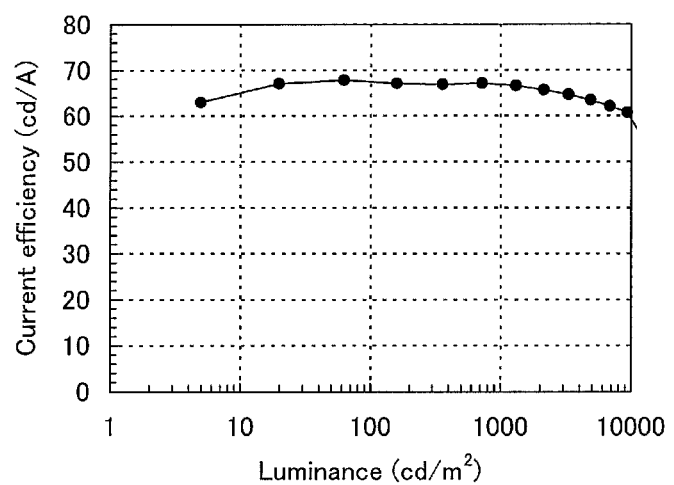
FIG. 44 is a graph showing luminance vs. current efficiency characteristics of Light-Emitting Element 13.

FIG. 42 shows the current density vs. luminance characteristics of Light-Emitting Element 13. FIG. 43 shows the voltage vs. luminance characteristics of Light-Emitting Element 13. FIG. 44 shows the luminance vs. current efficiency characteristics of Light-Emitting Element 13. In FIG. 42, the vertical axis represents luminance (cd/m$^2$) and the horizontal axis represents current density (mA/cm$^2$). In FIG. 43, the vertical axis represents luminance (cd/m$^2$) and the horizontal axis represents voltage (V). In FIG. 44, the vertical axis represents current efficiency (cd/A) and the horizontal axis represents luminance (cd/m$^2$). In addition, Table 10 shows the voltage, chromaticity, current efficiency, and external quantum efficiency of Light-Emitting Element 13 around 1000 cd/m$^2$.

TABLE 10

|  | Voltage (V) | Chromaticity x | Chromaticity y | Current efficiency (cd/A) | Quantum efficiency (%) |
| --- | --- | --- | --- | --- | --- |
| Light-Emitting Element 13 | 4.0 | 0.33 | 0.62 | 67 | 19 |

According to Example 10, it was confirmed that the light-emitting element 13 formed using the fluorene derivative (abbreviation: BPAFLP) of the present invention had sufficient characteristics to function as a light-emitting element. Further, from the results of the reliability test, it was found that a highly reliable light-emitting element was obtained in which a short circuit due to defects of the film or the like was not caused even if the light-emitting element was made to emit light continuously.

Furthermore, when a continuous lighting test was conducted in which Light-Emitting Element 13 was continuously lit by constant current driving with the initial luminance set at 1000 cd/m$^2$, 86% of the initial luminance was maintained even after 1900 hours. Thus, Light-Emitting Element 13 was found to have a long lifetime. Accordingly, it was confirmed that by application of BPAFLP (abbreviation) of an embodiment of the present invention to the hole-injection layer, a light-emitting element having a long lifetime can be obtained.

Example 11

Synthesis Example 3

In Example 11, a synthesis example of the fluorene derivative which is represented as General Formula (G1) in Embodiment 1 and an embodiment of the present invention is described. Specifically, a synthesis method of 4-phenyl-3'-(9-phenylfluoren-9-yl)triphenylamine (abbreviation: mBPAFLP), which is shown in Structural Formula (118) in Embodiment 1, is described. A structure of mBPAFLP is shown below.

[Chemical Formula 42]

(118)

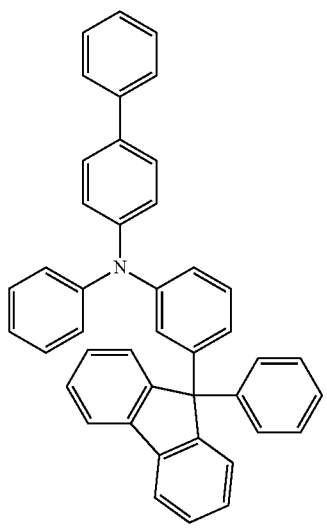

Step 1: synthesis method of
9-(3-bromophenyl)-9-phenylfluorene

In a 200-mL three-neck flask, 30 mL of a dehydrated THF solution of 4.2 g (18 mmol) of 2-bromobiphenyl was added thereto, and then the mixture solution was stirred at −78° C. 11 mL (18 mmol) of an n-BuLi hexane solution (1.57 M) was dropped into this mixture solution, and the mixture was stirred for 2.5 hours. After that, 40 mL of dehydrated THF solution of 3.9 g (15 mmol) of 3-bromobenzophenone was dropped to this mixture, and the mixture was stirred for 2 hours and at room temperature for 16 hours.

After the reaction, 1N-diluted hydrochloric acid was added to this mixture solution, and the mixture was stirred for 1 hour. This mixture was washed with water. The obtained organic phase was concentrated to obtain a candy-like substance.

Then, in a 200-mL recovery flask, this candy-like substance, 20 mL of glacial acetic acid, and 1.0 mL of hydrochloric acid were put, and the mixture was heated and stirred under a nitrogen atmosphere at 130° C. for 2 hours to be reacted.

After the reaction, this reaction mixture solution was dropped into 150 mL of ice-cooled water, so that a caramel-like solid was precipitated. An insoluble component of this was removed by decantation. This caramel-like solid was dissolved in 100 mL of toluene, and a saturated sodium hydrogen carbonate aqueous solution was added thereto with stirring the toluene solution until no more bubble comes out. An organic layer of this was washed with water, and then silica gel was added to adsorb moisture. The filtrate which was obtained by filtration of the mixture was concentrated, and methanol was added thereto. The mixture was irradiated with ultrasonic wave while being cooled with ice and then the produced solid was filtrated. 4.9 g of an objective white powder was obtained at a yield of 83%. A reaction scheme of the above synthesis method is shown in the following (J-5).

[Chemical Formula 43]

(J-5)

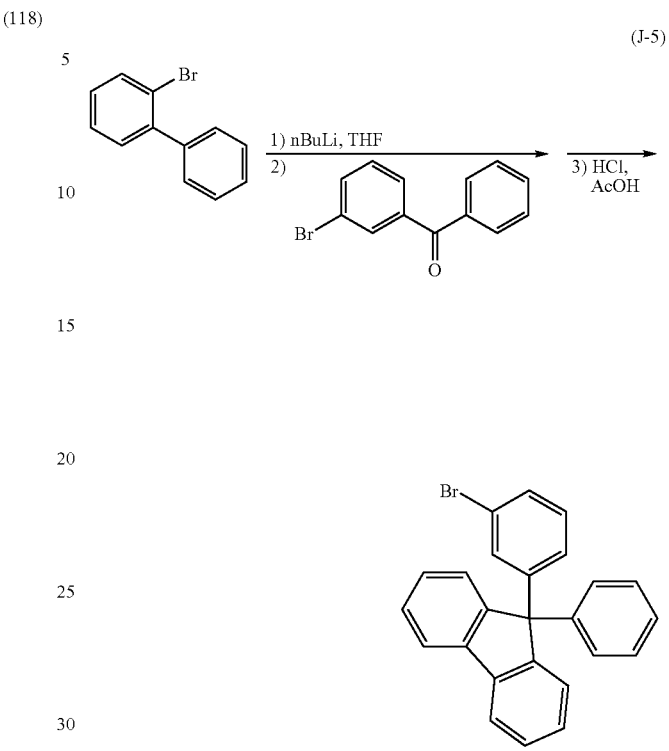

Step 2: synthesis method of 4-phenyl-3'-(9-phenylfluoren-9-yl)triphenylamine (abbreviation: mBPAFLP)

2.4 g (6.0 mmol) of 9-(3-bromophenyl)-9-phenylfluorene, 1.5 g (6.0 mmol) of 4-phenyl-diphenylamine, 1.0 g (10 mmol) of sodium tert-butoxide, and 3.0 mg (0.005 mmol) of bis (dibenzylideneacetone)palladium(0) were added to a 200-mL three-neck flask, and the atmosphere in the flask was substituted by nitrogen. Then, 25 mL of dehydrated xylene was added to this mixture. After the mixture was deaerated while being stirred under reduced pressure, 0.2 mL (0.1 mmol) of tri(tert-butyl)phosphine (10 wt % hexane solution) was added thereto. This mixture was heated and stirred under a nitrogen atmosphere at 130° C. for 2.5 hours to be reacted.

After the reaction, 200 mL of toluene was added to the reaction mixture solution, and the resulting suspension was filtrated through Florisil (produced by Wako Pure Chemical Industries, Ltd., Catalog No. 540-00135), alumina, and Celite (produced by Wako Pure Chemical Industries, Ltd., Catalog No. 531-16855). The obtained filtrate was concentrated and purified by silica gel column chromatography (developing solvent, toluene: hexane=1:4). The obtained fraction was concentrated, and acetone and methanol were added thereto. The mixture was irradiated with supersonic and then recrystallized to obtain 3.2 g of an objective white powder at a yield of 97%. A reaction scheme of the above synthesis method is shown in the following (J-6).

[Chemical Formula 44]

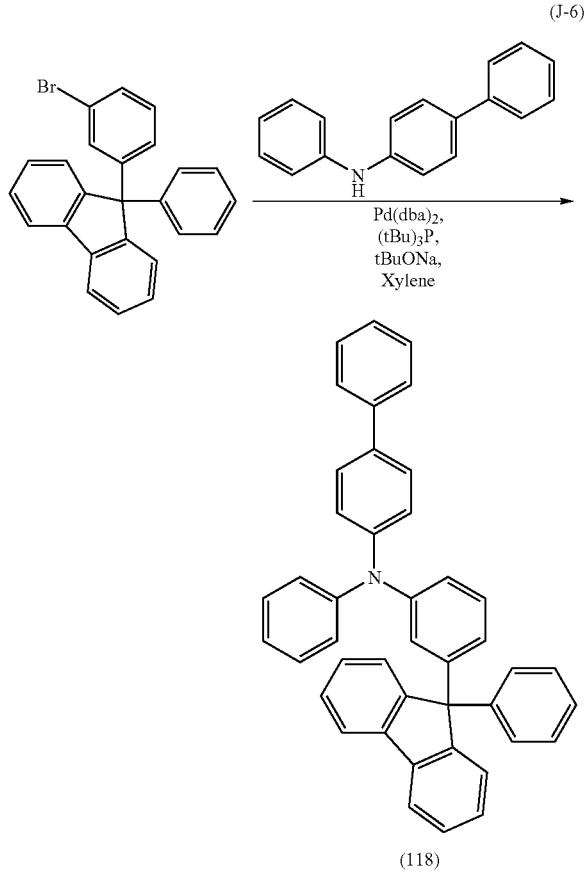

An Rf value of the object by a silica gel thin layer chromatography (TLC) (developing solvent, ethyl acetate:hexane=1:10) was 0.51, that of 9-(3-bromophenyl)-9-phenylfluorene was 0.62, and that of 4-phenyl-diphenylamine was 0.39.

Figure 45A:
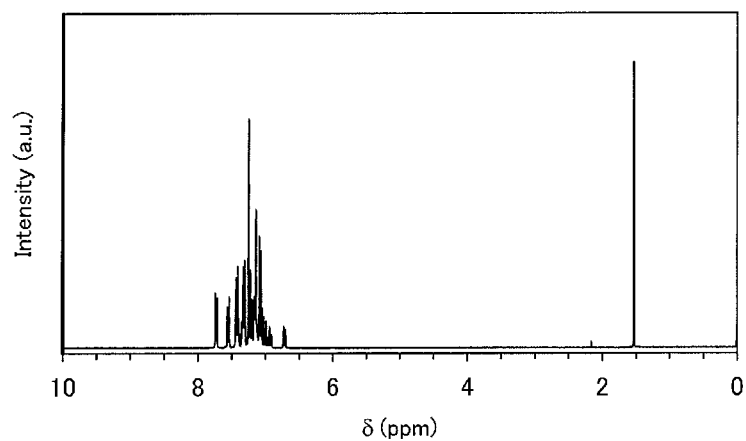
FIGS. 45A and 45B are $^1$H-NMR charts of 4-phenyl-3'-(9-phenylfluoren-9-yl)triphenylamine.
Figure 45B:
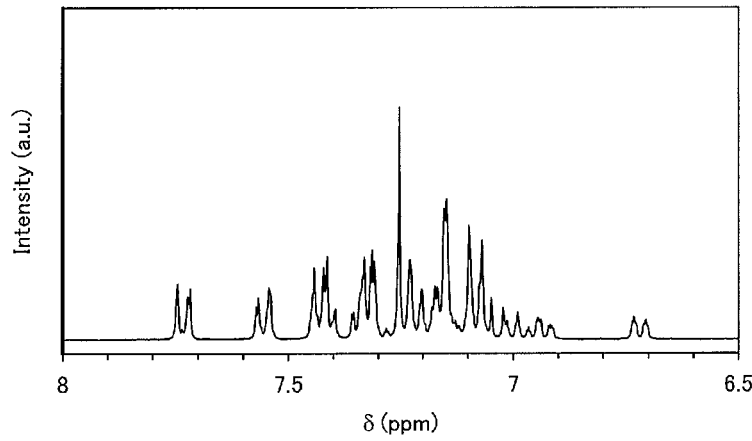

A compound that was obtained through Step 2 was subjected to a nuclear magnetic resonance ($^1$H-NMR) measurement. The measurement data are shown below. The $^1$H-NMR chart is shown in FIGS. 45A and 45B. The measurement results show that the fluorene derivative mBPAFLP (abbreviation) of the present invention, represented by Structural Formula (118) was obtained.

$^1$H-NMR (CDCl$_3$, 300 MHz): δ (ppm)=6.72 (d, J=8.4, 1H), 6.92-7.36 (m, 22H), 7.40-7.44 (m, 4H), 7.54-7.57 (m, 2H), and 7.72-7.75 (m, 2H).

Molecular weight of the compound obtained in Step 2 was measured by a GC-MS detector (ITQ1100 ion trap GCMS system, manufactured by Thermo Fisher). Accordingly, a main peak with a molecular weight of 561.3 (mode is EI+) was detected, and it was confirmed that an objective mBPAFLP (abbreviation) was obtained.

A variety of physical properties of mBPAFLP (abbreviation) of the obtained object were measured as described below.

Figure 46:
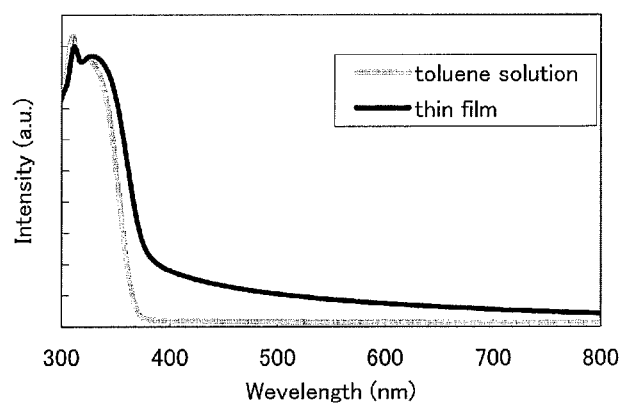
FIG. 46 is a graph showing absorption spectra of 4-phenyl-3'-(9-phenylfluoren-9-yl)triphenylamine.

The absorption spectrum (measurement range: 200 nm to 800 nm) was measured using an ultraviolet-visible spectrophotometer (V-550, manufactured by JASCO Corporation). FIG. 46 shows absorption spectra of a toluene solution and a thin film. The horizontal axis indicates the wavelength (nm) and the vertical axis indicates the absorption intensity (arbitrary unit). The toluene solution put into a quartz cell was measured. The spectrum in which the absorption spectra of the quartz and toluene were subtracted from the absorption spectrum of the sample is shown. Samples in which a thin film was evaporated on a quartz substrate were measured, and the spectrum in which the absorption spectrum of the quartz was subtracted from the absorption spectrum of the sample is shown. From these spectra, in the case of the toluene solution, absorption peaks on a long wavelength side were observed at around 310 nm and 325 nm, and in the case of the thin film, absorption peaks on a long wavelength side were observed at around 312 nm and 329 nm.

Figure 47:
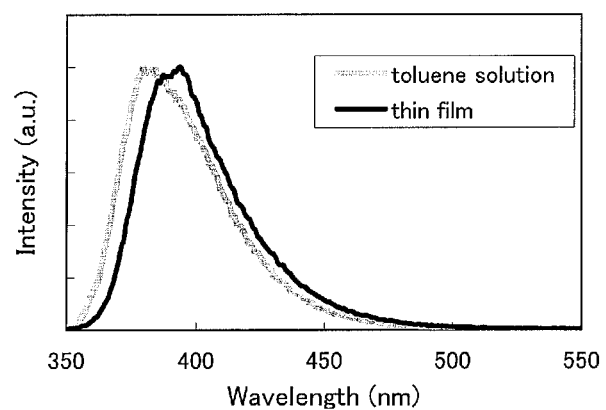
FIG. 47 is a graph showing emission spectra of 4-phenyl-3'-(9-phenylfluoren-9-yl)triphenylamine.

The emission spectrum was measured using a fluorescence spectrophotometer (FS920, manufactured by Hamamatsu Photonics Corporation). FIG. 47 shows emission spectra of a toluene solution and a thin film. The horizontal axis indicates the wavelength (nm) and the vertical axis indicates the emission intensity (arbitrary unit). The toluene solution put into a quartz cell was measured, and as the thin film, a sample evaporated on a quartz substrate was measured. From these spectra, in the case of the toluene solution, the maximum emission wavelength was observed at 382 nm (excitation wavelength: 340 nm), and in the case of the thin film, the maximum emission wavelengths was observed at 393 nm (excitation wavelength: 343 nm).

The result of measuring the thin film using a photoelectron spectrometer (AC-2, manufactured by Riken Keiki Co., Ltd.) under the atmosphere indicated that the HOMO level of the thin film was −5.73 eV. The Tauc plot of the absorption spectrum of the thin film revealed that the absorption edge was 3.34 eV. Thus, the energy gap in the solid state was estimated to be 3.34 eV, which means that the LUMO level of the thin film is −2.39 eV. This indicates that mBPAFLP (abbreviation) has a relatively deep HOMO level and a wide band gap (Bg).

The characteristics of oxidation-reduction reaction of mBPAFLP (abbreviation) were examined by a cyclic voltammetry (CV) measurement. Note that an electrochemical analyzer (ALS model 600A or 600C, manufactured by BAS Inc.) was used for the measurement.

Note that for the measurement of the oxidation reaction characteristic, the potential of the working electrode with respect to the reference electrode was scanned from −0.38 V to 0.69 V and then from 0.69 V to 0.38 V. As a result, the HOMO level was found to be −5.53 [eV]. In addition, the oxidation peak took a similar value even after the 100 cycles. Accordingly, it was found that repetition of the oxidation reduction between an oxidation state and a neutral state had favorable characteristics.

A melting point was measured. The melting point was 211° C. to 212° C.

Example 12

In Example 12, a method for manufacturing a light-emitting element formed using 4-phenyl-3'-(9-phenylfluoren-9-yl)triphenylamine (abbreviation: mBPAFLP), which is the fluorene derivative synthesized in Example 1 and measurement results of element characteristics are described.

An element structure of a light-emitting element in Example 12 is illustrated in FIG. 18. Light-Emitting Element 14 was formed using the above-described fluorene derivative (abbreviation: mBPAFLP) of an embodiment of the present invention for a hole-injection layer and a hole-transport layer.

First, indium oxide-tin oxide containing silicon oxide was deposited on a substrate 1501 which was a glass substrate by a sputtering method to form a first electrode 1502. Note that the thickness of the first electrode 1502 was 110 nm and the electrode area was 2 mm×2 mm.

Next, an EL layer 1503 including a stack of a plurality of layers is formed over the first electrode 1502. In Example 9, the EL layer 1503 has a structure in which a first layer 1511 which is a hole-injection layer, a second layer 1512 which is a hole-transport layer, a third layer 1513 which is a light-emitting layer, a fourth layer 1514 which is an electron-transport layer, and a fifth layer 1515 which is an electron-injection layer are sequentially stacked.

The substrate provided with the first electrode 1502 was fixed to a substrate holder which was provided in a vacuum evaporation apparatus so that a surface provided with the first electrode 1502 faced downward. The pressure in the vacuum evaporation apparatus was reduced to approximately $10^{-4}$ Pa. Then, over the first electrode 1502, a hole-injection material was deposited to a thickness of 50 nm to form the first layer 1511 which was a hole-injection layer. When Light-Emitting Element 14 was formed, 4-phenyl-3'-(9-phenylfluoren-9-yl)triphenylamine (abbreviation: mBPAFLP) and molybdenum (VI) oxide were co-evaporated to form the first layer 1511 which was a hole-injection layer 1511. The thickness was 50 nm, and the evaporation rate was controlled so that the weight ratio of mBPAFLP (abbreviation) to molybdenum (VI) oxide could be 4:2=(mBPAFLP: molybdenum oxide). Further, when Comparative Light-Emitting Element 15 was formed, 4,4'-bis[N-(1-naphthyl)-N-phenylamino]biphenyl (abbreviation: NPB) and molybdenum(VI) oxide were co-evaporated to form the first layer 1511 which was a hole-injection layer. The thickness was 50 nm, and the evaporation rate was controlled so that the weight ratio of NPB to molybdenum (VI) oxide could be 4:2=(NPB: molybdenum oxide).

Next, a hole-transport material was deposited on the first layer 1511 to a thickness of 10 nm by an evaporation method using resistance heating, and the second layer 1512 which was a hole-transport layer was formed. Note that Light-Emitting Element 14 was formed using 4-phenyl-3'-(9-phenylfluoren-9-yl)triphenylamine (abbreviation: mBPAFLP) and Comparative Light-Emitting Element 15 was formed using 4,4'-bis[N-(1-naphthyl)-N-phenylamino]biphenyl (abbreviation: NPB).

Next, the third layer 1513 which was a light-emitting layer was formed on the second layer 1512 by an evaporation method using resistance heating. As the third layer 1513, 9-[4-(10-phenyl-9-anthryl)phenyl]-9H-carbazole (abbreviation: CzPA) and 4-(10-phenyl-9-anthryl)-4'-(9-phenyl-91–/–carbazol-3-yl)triphenylamine (abbreviation: PCBAPA) were co-evaporated to form a 30-nm-thick film. Here, the evaporation rate was controlled so that the weight ratio of CzPA to PCBAPA was 1:0.075=(CzPA:PCBAPA).

Furthermore, on the third layer 1513, a 10-nm-thick film of tris(8-quinolinolato)aluminum(III) (abbreviation: Alq) and, thereon, a 20-nm-thick film of bathophenanthroline (abbreviation: BPhen) were formed by an evaporation method using resistance heating to form the fourth layer 1514 which was an electron-transport layer.

On the fourth layer 1514, a 1-nm-thick film of lithium fluoride (LiF) was formed as the fifth layer 1515 which was an electron-injection layer.

Finally, a film of aluminum was formed to have a thickness of 200 nm by an evaporation method using resistance heating, whereby a second electrode 1504 was formed. In this manner, Light-Emitting Element 14 and Comparative Light-Emitting Element 15 were formed.

Note that Light-Emitting Element 14 and Comparative Light-Emitting Element 15 were formed in the same steps, except those of the first layer 1511 and the second layer 1512.

Light-Emitting Element 14 and Comparative Light-Emitting Element 15 thus obtained were sealed in a glove box having a nitrogen atmosphere without being exposed to the air. Then, the operating characteristics thereof were measured. Note that the measurement was carried out at room temperature (in an atmosphere kept at 25° C.).

Figure 48:
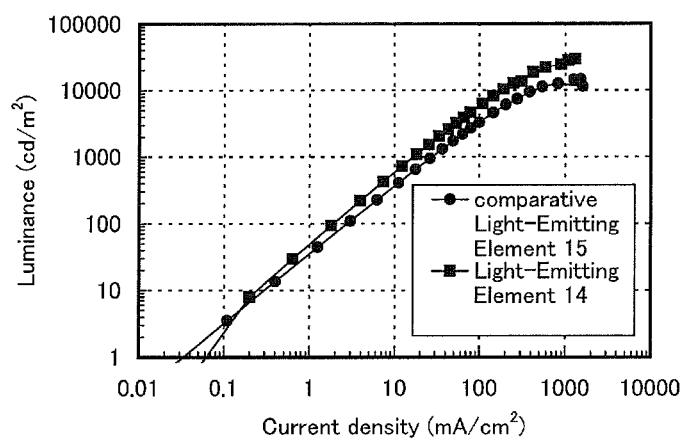
FIG. 48 is a graph showing current density vs. luminance characteristics of Light-Emitting Element 14 and Comparative Light-Emitting Element 15.
Figure 49:
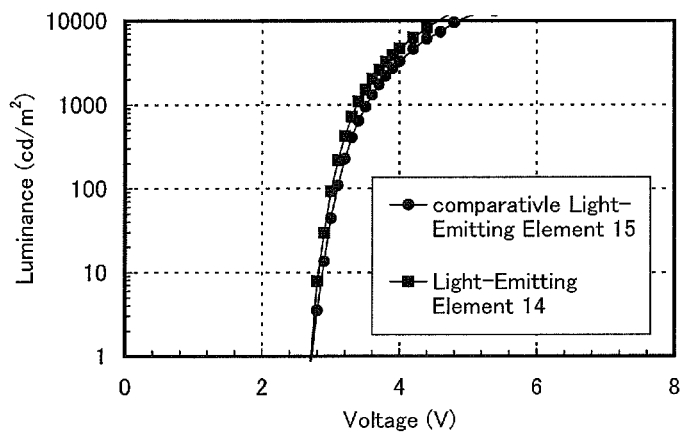
FIG. 49 is a graph showing voltage vs. luminance characteristics of Light-Emitting Element 14 and Comparative Light-Emitting Element 15.
Figure 50:
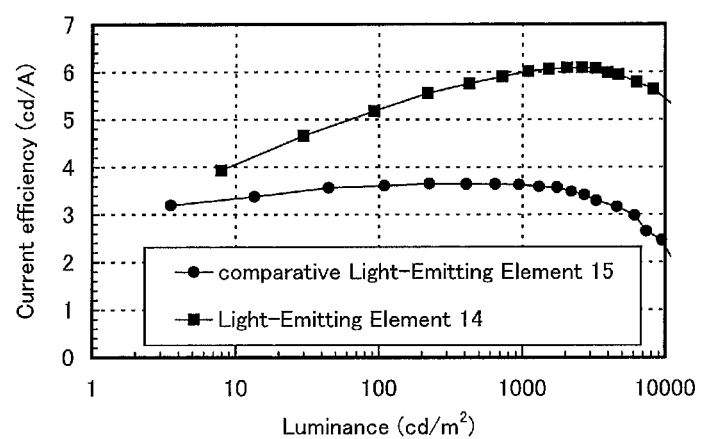
FIG. 50 is a graph showing luminance vs. current efficiency characteristics of Light-Emitting Element 14 and Comparative Light-Emitting Element 15.

FIG. 48 shows the current density vs. luminance characteristics of Light-Emitting Element 14 and Comparative Light-Emitting Element 15. FIG. 49 shows the voltage vs. luminance characteristics of Light-Emitting Element 14 and Comparative Light-Emitting Element 15. FIG. 50 shows the luminance vs. current efficiency characteristics of Light-Emitting Element 14 and Comparative Light-Emitting Element 15. In FIG. 48, the vertical axis represents luminance ($cd/m^2$) and the horizontal axis represents current density ($mA/cm^2$). In FIG. 49, the vertical axis represents luminance ($cd/m^2$) and the horizontal axis represents voltage (V). In FIG. 50, the vertical axis represents current efficiency (cd/A) and the horizontal axis represents luminance ($cd/m^2$). In addition, Table 11 shows the voltage, chromaticity, and current efficiency of Light-Emitting Element 14 and Comparative Light-Emitting Element 15 around 1000 $cd/m^2$.

TABLE 11

| | Voltage (V) | Chromaticity x | Chromaticity y | Current efficiency (cd/A) |
|---|---|---|---|---|
| Light-Emitting Element 14 | 3.50 | 0.16 | 0.20 | 3.63 |
| Comparative Light-Emitting Element 15 | 3.40 | 0.16 | 0.22 | 6.01 |

When the drive voltage of Light-Emitting Element 14 was 3.4 V, the luminance was 1100 $cd/m^2$ and the current value was 0.72 mA. It was found that Light-Emitting Element 14 using mBPAFLP (abbreviation) for the second layer 1512 had higher current efficiency than Comparative Light-Emitting Element 15 using NPB for the second layer 1512. It was understood that this was because carrier balance of Light-Emitting Element 14 was improved as compared with Comparative Light-Emitting Element 15. It was thought that since the HOMO level of mBPAFLP (abbreviation) was close to the HOMO level of CzPA (abbreviation) which was a host material of the light-emitting layer (in comparison with NPB), the hole-injection property of mBPAFLP (abbreviation), from the hole-transport layer to the light-emitting layer, was improved. Further, it was thought that since mBPAFLP (abbreviation) had a high LUMO level (in comparison with NPB), the electron-blocking property of mBPAFLP (abbreviation), from the light-emitting layer to the hole-transport layer, was improved. Furthermore, it was thought that since mBPAFLP (abbreviation) had a wide band gap (Bg) (in comparison with NPB), excitons generated in the third layer (light-emitting layer) 1513 were not transferred to the second layer 1512 which was an adjacent layer (that is to say, not quenched) and were confined.

In addition, when a continuous lighting test was conducted in which Light-Emitting Element 14 and Comparative Light-Emitting Element 15 were continuously lit by constant current driving with the initial luminance set at 1000 $cd/m^2$, after 280 hours, Light-Emitting Element 14 exhibits 80% of the initial luminance and Comparative Light-Emitting Element 15 exhibits 72% of the initial luminance, which leads to that Light-Emitting Element 14 and Comparative Light-Emitting Element 15 have a long lifetime. Thus, it was found that by application of mBPAFLP (abbreviation) of the present invention, a light-emitting element having a long lifetime can be obtained.

Reference Example 1

A synthesis method of 4-(10-phenyl-9-anthryl)-4'-(9-phenyl-9H-carbazol-3-yl)triphenylamine (abbreviation: PCBAPA) which is used in Example 3 to Example 5 is described in detail.

[Chemical Formula 45]

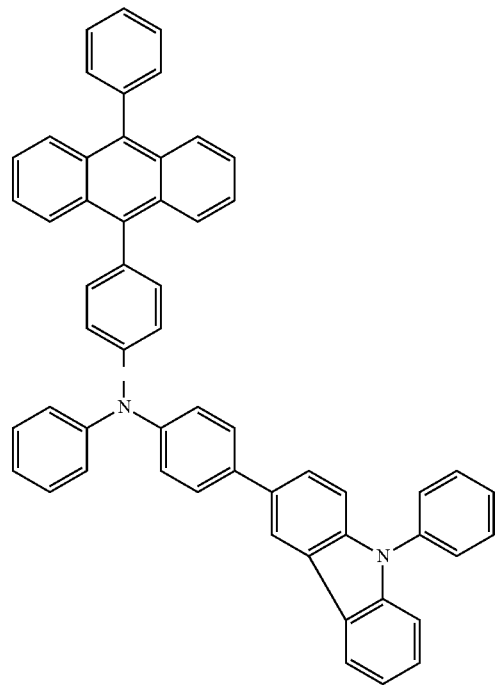

The synthesis scheme of 4-(10-phenyl-9-anthryl)-4'-(9-phenyl-9H-carbazol-3-yl)triphenylamine (abbreviation: PCBAPA) is shown in the following (X-1).

[Chemical Formula 46]

(X-1)

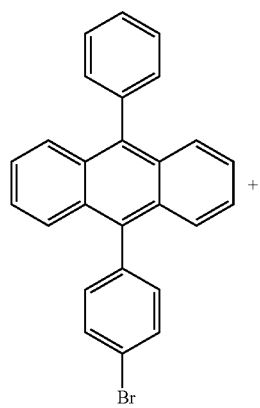

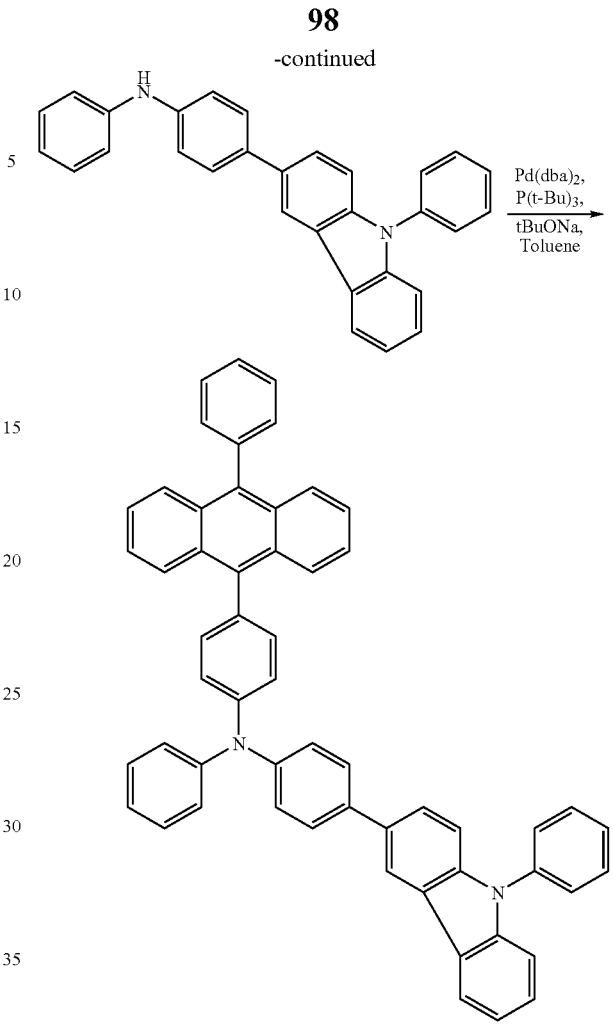

7.8 g (12 mmol) of 9-(4-bromophenyl)-10-phenylanthracene, 4.8 g (12 mmol) of 4-(9-phenyl-9H-carbazol-3-yl)diphenylamine (abbreviation: PCBA), and 5.2 g (52 mmol) of sodium tert-butoxide were added to a 300-mL three-neck flask, and the atmosphere in the flask was substituted by nitrogen. Then, 60 mL of toluene and 0.30 mL of tri(tert-butyl)phosphine (10 wt % hexane solution) were added to this mixture. After the mixture was deaerated while being stirred under reduced pressure, 136 mg (0.24 mmol) of bis(dibenzylideneacetone)palladium(0) was added thereto. This mixture was stirred at 100° C. for 3 hours. After the stirring, about 50 mL of toluene was added to this mixture. The mixture was subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135). The obtained filtrate was concentrated to give a yellow solid. This solid was recrystallized with toluene/hexane to give 6.6 g of a light yellow powdered solid PCBAPA, which was the object of the synthesis, at a yield of 75%.

Then, 3.0 g of the obtained light yellow powdered solid was sublimated and purified by a train sublimation method. For sublimation purification conditions, PCBAPA was heated at 350° C. under a pressure of 8.7 Pa with a flow rate of argon gas of 3.0 mL/min. After the sublimation purification, 2.7 g of a light yellow solid of PCBAPA was obtained at a yield of 90%.

The obtained compound was subjected to a nuclear magnetic resonance ($^1$H-NMR) measurement. The measurement data are shown below.

$^1$H-NMR (CDCl$_3$, 300 MHz): δ (ppm)=7.09-7.14 (m, 1H), 7.28-7.72 (m, 33H), 7.88 (d, J=8.4 Hz, 2H), 8.19 (d, J=7.2 Hz, 1H), and 8.37 (d, J=1.5 Hz, 1H).

The measurement results show that 4-(10-phenyl-9-anthryl)-4'-(9-phenyl-9H-carbazol-3-yl)triphenylamine (abbreviation: PCBAPA) was obtained.

Light-Emitting Element 1 to Light-Emitting Element 5 described in the above examples can be formed with use of 4-(10-phenyl-9-anthryl)-4'-(9-phenyl-9H-carbazol-3-yl) triphenylamine (abbreviation: PCBAPA).

Reference Example 2

A synthesis method of 3-phenyl-9-[4-(5-phenyl-1,3,4-oxadiazol-2-yl)phenyl]-9H-carbazole (abbreviation: CO11II) which is used in Example 6 and Example 7 is described in detail.

[Chemical Formula 47]

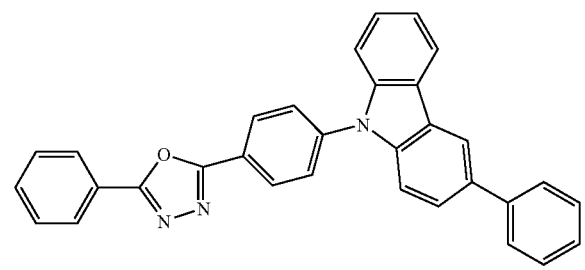

The synthesis scheme of 3-phenyl-9-[4-(5-phenyl-1,3,4-oxadiazol-2-yl)phenyl]-9H-carbazole (abbreviation: CO11II) is shown in (Y-1).

[Chemical Formula 48]

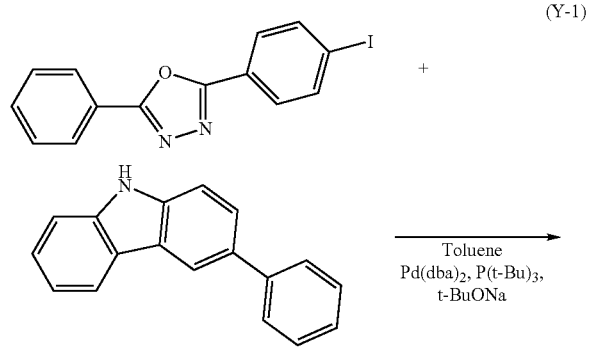

(Y-1)

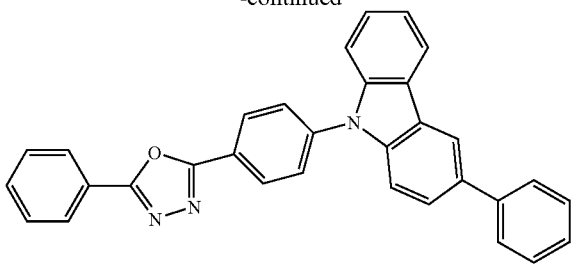

2.3 g (6.6 mmol) of 2-(4-iodophenyl)-5-phenyl-1,3,4-oxadiazole, 1.6 g (6.6 mmol) of 3-phenyl-9H-carbazole, and 1.4 g (15 mmol) of sodium tert-butoxide were added to a 100 mL three-necked flask, and the atmosphere in the flask was replaced with nitrogen. To this mixture were added 30 mL of toluene and 0.2 mL of a 10 wt % hexane solution of tri(tert-butyl)phosphine, and the mixture was degassed by reducing the pressure of the flask with an aspirator, and then, the atmosphere in the flask was replaced with nitrogen. To the mixture was added 0.058 g (0.10 mmol) of bis(dibenzylideneacetone)palladium(0), followed by stirring under a nitrogen stream at 80° C. for 15 hours. After the stirring, toluene was added to the mixture, and this suspension was washed with a saturated sodium carbonate aqueous solution and saturated saline in this order. Then, magnesium sulfate was added to the organic layer to adsorb moisture. After that, suction filtration was performed on this mixture to obtain filtrate. Suction filtration was performed with Cellite (Wako Pure Chemical Industries. Ltd., catalog number: 540-16855) on the obtained filtrate, and thus a filtrate was obtained. A compound obtained by concentrating the obtained filtrate was purified by silica gel column chromatography. The column chromatography was performed first using toluene as a developing solvent and then using a mixed solvent of toluene:ethyl acetate=4:1 as a developing solvent. Acetone was added to a solid obtained by concentrating the obtained fraction, and washed with ultrasonic wave irradiation. This mixture was subjected to suction filtration to collect a solid. The collected solid was recrystallized with a mixed solvent of chloroform and hexane, so that 2.0 g of a powder white solid was obtained at a yield of 64%.

1.1 g of the obtained white solid was sublimated and purified by a train sublimation method. The sublimation purification was carried out under reduced pressure of 3.0 Pa, with a flow rate of argon at 5 mL/min, at 240° C. for 16 hours. Thus, 0.98 g of the white solid was obtained at a yield of 89%.

The obtained compound was subjected to a nuclear magnetic resonance ($^1$H-NMR) measurement. The measurement data are shown below.

$^1$H-NMR (CDCl$_3$, 300 MHz): δ (ppm)=7.30-7.76 (m, 13H), 7.79 (d, J=8.3 Hz, 2H), 8.14-8.24 (m, 3H), 8.35 (sd, J=1.5 Hz, 1H), and 8.39 (d, J=8.8 Hz, 2H).

The measurement results show that 3-phenyl-9-[4-(5-phenyl-1,3,4-oxadiazol-2-yl)phenyl]-9H-carbazole (abbreviation: CO11II) was obtained.

Light-Emitting Element 6 to Light-Emitting Element 10 described in the above examples can be formed with use of 3-phenyl-9-[4-(5-phenyl-1,3,4-oxadiazol-2-yl)phenyl]-9H-carbazole (abbreviation: CO11II).

Reference Example 3

A synthesis method of 4-phenyl-4'-(9-phenyl-9H-carbazol-3-yl)triphenylamine (abbreviation: PCBA1BP) which is used in Example 7 is described in detail.

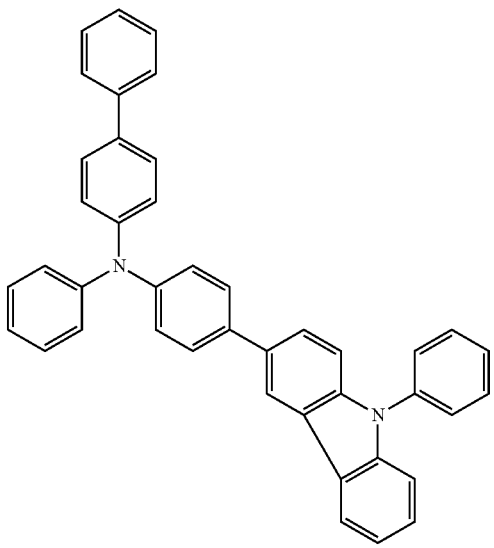

The synthesis scheme of 4-phenyl-4'(9-phenyl-9H-carbazol-3-yl)triphenylamine (abbreviation: PCBA1BP) is shown in (Z-1).

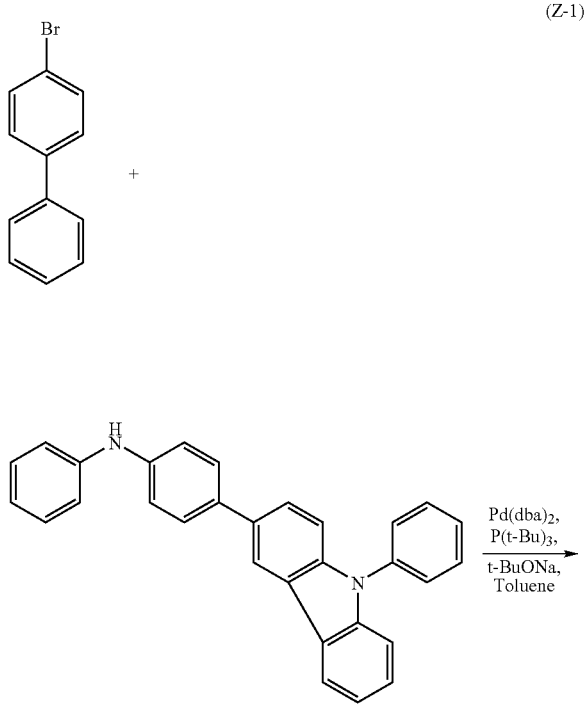

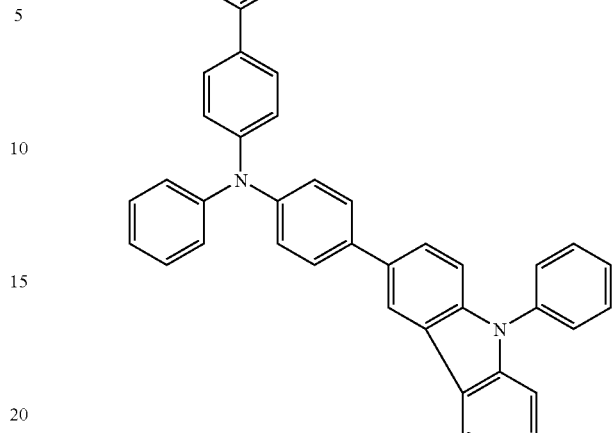

In a 100-mL three-neck flask, 2.0 g (4.9 mmol) of 4-(9-phenyl-9H-carbazol-3-yl)diphenylamine, 1.1 g (4.9 mmol) of 4-bromobiphenyl, and 2.0 g (20 mmol) of sodium tert-butoxide were put, and the atmosphere in the flask was substituted by nitrogen. Then, 50 mL of toluene and 0.30 mL of tri(tert-butyl)phosphine (10 wt % hexane solution) were added to this mixture.

After the mixture was deaerated while being stirred under reduced pressure, 0.10 g of bis(dibenzylideneacetone)palladium(0) was added thereto. This mixture was heated and stirred at 80° C. for 5 hours to be reacted. After the reaction, toluene was added to this reaction mixture. This suspension was subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135), and thus a filtrate was obtained. The obtained filtrate was washed with a saturated sodium carbonate aqueous solution and saturated saline in this order. Then, magnesium sulfate was added to the organic layer to adsorb moisture. After the drying, suction filtration was performed on the mixture to remove the magnesium sulfate, and thus a filtrate was obtained.

The obtained filtrate was concentrated, and purified by silica gel column chromatography. The silica gel column chromatography was performed by, first, using a mixture solvent of toluene: hexane=1:9 as a developing solvent, and then using a mixture solvent of toluene: hexane=3:7 as another developing solvent. A solid which was obtained by concentrating the obtained fraction was recrystallized with a mixture solvent of chloroform and hexane to obtain 2.3 g of a white powder-like solid at a yield of 84%.

1.2 g of the obtained white solid was sublimated and purified by a train sublimation method. The sublimation purification was carried out under reduced pressure of 7.0 Pa, with a flow rate of argon at 3 mL/min, at 280° C. for 20 hours. Thus, 1.1 g of the white solid was obtained at a yield of 89%.

The obtained compound was subjected to a nuclear magnetic resonance ($^1$H-NMR) measurement. The measurement data are shown below.

$^1$H-NMR (DMSO-$d_6$, 300 MHz): δ (ppm)=7.05-7.20 (m, 7H), 7.28-7.78 (m, 21H), 8.34 (d, J=7.8 Hz, 1H), and 8.57 (s, 1H).

The measurement results show that 4-phenyl-4'-(9-phenyl-9H-carbazol-3-yl)triphenylamine (abbreviation: PCBA1BP) was obtained.

Light-Emitting Element 8 to Light-Emitting Element 10 described in the above examples can be formed with use of 4-phenyl-4'-(9-phenyl-9H-carbazol-3-yl)triphenylamine (abbreviation: PCBA1BP).

Reference Example 4

Another synthesis method of 4-phenyl-4'-(9-phenyl-9H-carbazol-3-yl)triphenylamine (abbreviation: PCBA1BP) which is different from the method described in Reference Example 3 is described in detail. This synthesis method is preferable because an object with higher purity can be easily obtained with high yield.

[Chemical Formula 51]

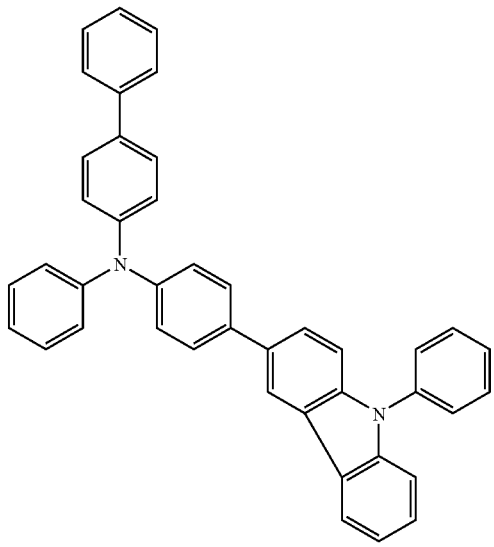

Step 1: synthesis method of 3-(4-bromophenyl)-9-phenyl-9H-carbazole

A synthesis scheme of 3-(4-bromophenyl)-9-phenyl-9H-carbazole is shown in (Z-2).

[Chemical Formula 52]

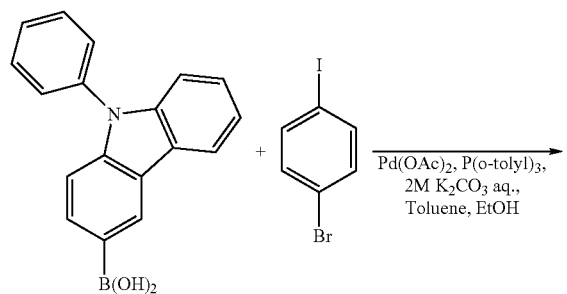

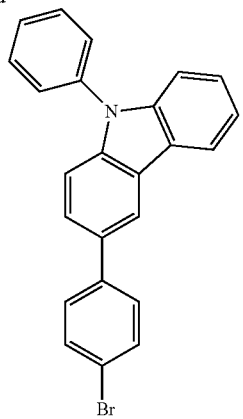

In a 300-mL three-neck flask, a mixture of 14 g (50 mmol) of 4-bromoiodobenzene, 14 g (50 mmol) of 9-phenyl-9H-carbazol-3-boronic acid, 110 mg (0.5 mmol) of palladium(II) acetate, 300 mg (1.0 mmol) of tri(o-tolyl)phosphine, 50 mL of toluene, 10 mL of ethanol, and 25 mL of a potassium carbonate aqueous solution (2 mol/L) was deaerated while being stirred under reduced pressure and was heated and stirred under a nitrogen atmosphere at 80° C. for 6 hours to be reacted.

After the reaction, 200 mL of toluene was added to the reaction mixture solution, and the resulting suspension was filtrated through Florisil (produced by Wako Pure Chemical Industries, Ltd., Catalog No. 540-00135) and Celite (produced by Wako Pure Chemical Industries, Ltd., Catalog No. 531-16855). The obtained filtrate was washed with water, and magnesium sulfate was added thereto to adsorb moisture. This suspension was filtrated to obtain a filtrate. The obtained filtrate was concentrated and purified by silica gel column chromatography. At this time, a mixed solvent of toluene and hexane (toluene: hexane=1:4) was used as a developing solvent for the chromatography. The obtained fraction was concentrated, and hexane was added thereto. The mixture was irradiated with ultrasonic wave and then recrystallized, so that 15 g of an objective white powder was obtained at a yield of 75%.

An Rf value of the object by a silica gel thin layer chromatography (TLC) (developing solvent, ethyl acetate:hexane=1:10) was 0.32 and that of 4-bromoiodobenzene was 0.74.

Further, an RF value of 1,4-bis(9-phenyl-9H-carbazol-3-yl)benzene, which was a by-product, (developing solvent, ethyl acetate:hexane=1:10) was 0.23; however, spots were slightly observed on TLC in this reaction suspension. As a result, it was understood that since part of iodine had higher reactivity than part of bromo in 4-bromoiodobenzene which was a dihalide and was used for the source material, it was selectively (preferentially) reacted with 9-phenyl-9H-carbazol-3-boronic acid which was a boron compound (that is, the dihalide and the boron compound was reacted almost at 1:1). Furthermore, since the RF value of the object is sufficiently far from the RF value of the by-product, the object and the by-product can be easily separated in the above-described chromatography.

The obtained compound in Step 1 was subjected to a nuclear magnetic resonance ($^1$H-NMR) measurement. The measurement data are shown below.

$^1$H-NMR (CDCl$_3$, 300 MHz): δ (ppm)=7.24-7.32 (m, 1H), 7.40-7.64 (m, 13H), 8.17 (d, J=7.2, 1H), and 8.29 (s, 1H).

The measurement results show that 3-(4-bromophenyl)-9-phenyl-9H-carbazole, which was the object, was obtained.

Molecular weight of the above compound was measured by a GC-MS detector (ITQ1100 ion trap GC/MS system, manufactured by Thermo Fisher Scientific K.K.). Accordingly, a main peak with molecular weight of 397.13 (mode is EI+) was detected, and it was confirmed that 3-(4-bromophenyl)-9-phenyl-9H-carbazole, which was the object, was obtained.

A peak derived from 1,4-bis(9-phenyl-9H-carbazol-3-yl)benzene (molecular weight, 560.2), which was a by-product, was not detected by this GC-MS detector. Thus, it was confirmed that by the reaction in Step 1, an object with higher purity can be easily obtained with extremely high yield.

Step 2: synthesis method of 4-phenyl-4'-(9-phenyl-9H-carbazol-3-yl)triphenylamine (abbreviation: PCBA1BP)

A synthesis scheme of 4-phenyl-4'-(9-phenyl-9H-carbazol-3-yl)triphenylamine (abbreviation: PCBA1BP) is shown in (Z-3).

[Chemical Formula 53]

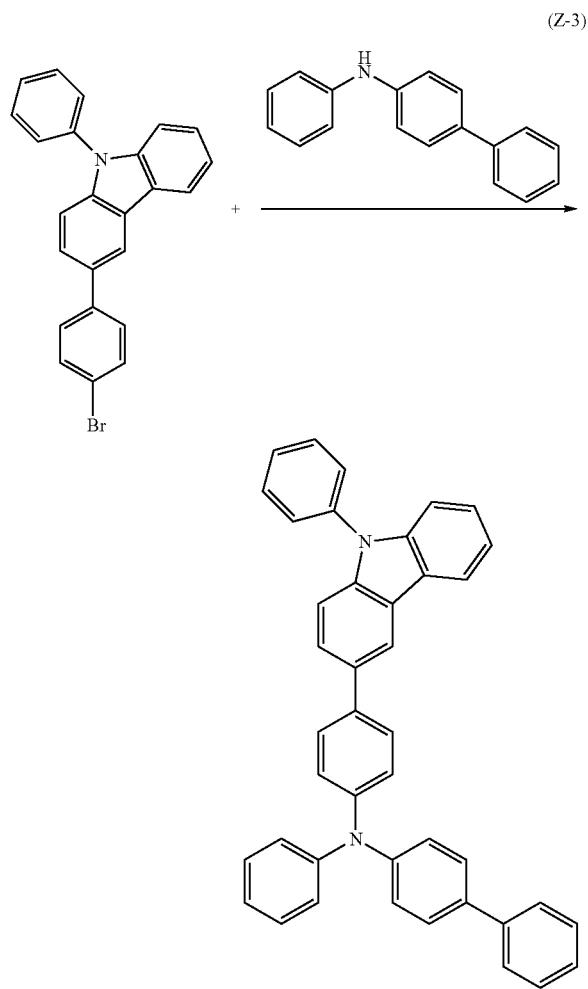

(Z-3)

4-phenyl-diphenylamine and 3-(4-bromophenyl)-9-phenyl-9H-carbazole were heated and stirred in an organic solvent using a palladium catalyst, a ligand of the palladium catalyst, and a base to be reacted.

After the reaction, this reaction mixture solution was purified to obtain an objective white powder.

The obtained compound was subjected to a nuclear magnetic resonance ($^1$H-NMR) measurement. From the measurement results, as in Reference Example 3, it was confirmed that 4-phenyl-4'-(9-phenyl-9H-carbazol-3-yl)triphenylamine (abbreviation: PCBA1BP), which is an object, can be obtained.

As described above, it was confirmed that by the synthesis method described in Reference Example 4, an object with higher purity can be easily obtained with extremely high yield.

This application is based on Japanese Patent Application Serial No. 2009-131504 filed with Japan Patent Office on May 29, 2009, the entire contents of which are hereby incorporated by reference.

REFERENCE NUMERALS

101: substrate, 102: first electrode, 103: EL layer, 104: second electrode, 111: layer, 112: layer, 113: layer, 114: layer, 115: layer, 301: electrode, 302: electrode, 303: EL layer, 304: EL layer, 305: charge-generation layer, 401: source side driver circuit, 402: pixel portion, 403: gate side driver circuit, 404: sealing substrate, 405: sealant, 407: space, 408: wiring, 409: flexible printed circuit (FPC), 410: element substrate, 411: switching TFT, 412: current control TFT, 413: first electrode, 414: insulator, 416: EL layer, 417: second electrode, 418: light-emitting element, 423: n-channel TFT, 424: p-channel TFT, 501: substrate, 502: first electrode, 503: second electrode, 504: EL layer, 505: insulating layer, 506: partition layer, 511: first light-emitting unit, 512: second light-emitting unit, 513: charge-generation layer, 521: first electrode, 522: second electrode, 611: housing, 612: supporting base, 613: display portion, 614: speaker portion, 615: video input terminal, 621: main body, 622: housing, 623: display portion, 624: keyboard, 625: external connection port, 626: pointing device, 631: main body, 632: housing, 633: display portion, 634: audio input portion, 635: audio output portion, 636: operation key, 637: external connection port, 638: antenna, 641: main body, 642: display portion, 643: housing, 644: external connection port, 645: remote control receiving portion, 646: image receiving portion, 647: battery, 648: audio input portion, 649: operation key, 650: eyepiece portion, 701: housing, 702: liquid crystal layer, 703: backlight, 704: housing, 705: driver IC, 706: terminal, 801: housing, 802: light source, 901: lighting device, 902: television set, 913: layer, 1501: substrate, 1502: first electrode, 1503: EL layer, 1504: second electrode, 1511: layer, 1512: layer, 1513: layer, 1514: layer, and 1515: layer.

The invention claimed is:
1. A fluorene derivative represented by Formula (101):

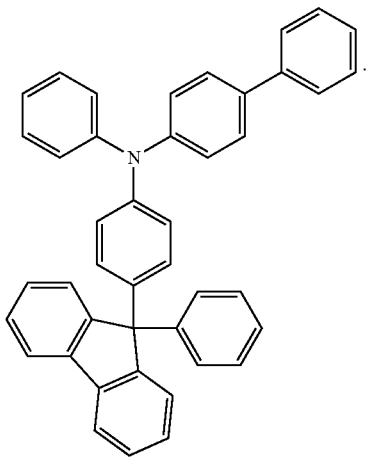

(101)

2. A light-emitting device comprising a light-emitting element, wherein the light-emitting element comprises:
   a pair of electrodes; and
   an electroluminescence layer including the fluorene derivative according to claim 1 between the pair of electrodes.
3. An electronic device comprising a light-emitting element, wherein the light-emitting element comprises:
   a pair of electrodes; and
   an electroluminescence layer including the fluorene derivative according to claim 1 between the pair of electrodes.
4. A fluorene derivative represented by Formula (151):

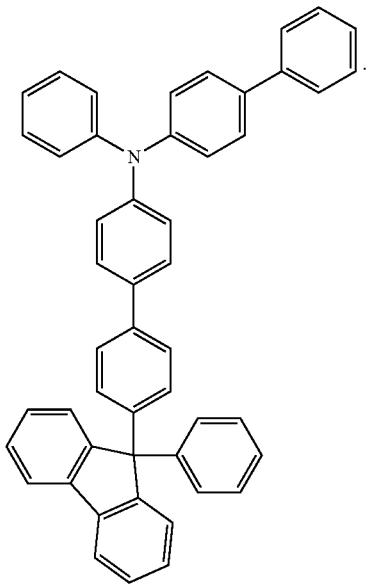

(151)

5. A light-emitting device comprising a light-emitting element, wherein the light-emitting element comprises:
   a pair of electrodes; and
   an electroluminescence layer including the fluorene derivative according to claim 4 between the pair of electrodes.
6. An electronic device comprising a light-emitting element, wherein the light-emitting element comprises:
   a pair of electrodes; and
   an electroluminescence layer including the fluorene derivative according to claim 4 between the pair of electrodes.
7. A fluorene derivative represented by Formula (118):

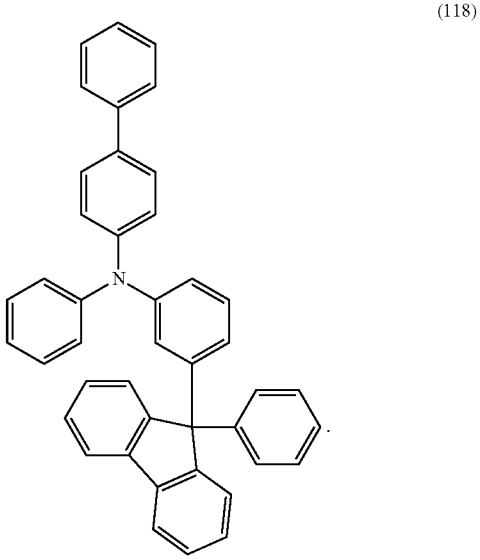 [SMILES: c1ccc(-c2ccc(N(c3ccccc3)c3cccc(C4(c5ccccc5)c5ccccc5-c5ccccc54)c3)cc2)cc1]

(118)

8. A light-emitting device comprising a light-emitting element, wherein the light-emitting element comprises:
   a pair of electrodes; and
   an electroluminescence layer including the fluorene derivative according to claim 7 between the pair of electrodes.
9. An electronic device comprising a light-emitting element, wherein the light-emitting element comprises:
   a pair of electrodes; and
   an electroluminescence layer including the fluorene derivative according to claim 7 between the pair of electrodes.

* * * * *